(12) United States Patent
Zhang et al.

(10) Patent No.: US 12,415,797 B2
(45) Date of Patent: Sep. 16, 2025

(54) HETEROCYCLIC COMPOUND AS CDK-HDAC DOUBLE-CHANNEL INHIBITOR

(71) Applicant: Hangzhou Innogate Pharma Co., Ltd., Zhejiang (CN)

(72) Inventors: Hancheng Zhang, Zhejiang (CN); Xiangyang Ye, Zhejiang (CN); Xin Cheng, Zhejiang (CN)

(73) Assignee: Hangzhou Innogate Pharma Co., Ltd., Zheijian (CN)

( * ) Notice: Subject to any disclaimer, the term of this patent is extended or adjusted under 35 U.S.C. 154(b) by 1112 days.

(21) Appl. No.: 17/309,494

(22) PCT Filed: Dec. 2, 2019

(86) PCT No.: PCT/CN2019/122503
§ 371 (c)(1),
(2) Date: Jun. 1, 2021

(87) PCT Pub. No.: WO2020/108661
PCT Pub. Date: Jun. 4, 2020

(65) Prior Publication Data
US 2022/0041577 A1    Feb. 10, 2022

(30) Foreign Application Priority Data
Nov. 30, 2018 (CN) .......................... 201811457309.8

(51) Int. Cl.
*C07D 401/14* (2006.01)
(52) U.S. Cl.
CPC .................. *C07D 401/14* (2013.01)
(58) Field of Classification Search
CPC .. C07D 401/14; C07D 403/04; C07D 487/04; A61K 31/519; A61P 35/00
See application file for complete search history.

(56) References Cited

FOREIGN PATENT DOCUMENTS

| CN | 105294655 A | 2/2016 | | |
|---|---|---|---|---|
| CN | 106831780 A | 6/2017 | | |
| CN | 107793399 A | 3/2018 | | |
| CN | 108929312 A | * 12/2018 | ........... | C07D 401/14 |
| WO | 2010075074 A1 | 7/2010 | | |

OTHER PUBLICATIONS

International Search Report (Form PCT/ISA/210) for International Patent Application No. PCT/CN2019/122503, issued from the International Searching Authority, date of mailing Mar. 9, 2020, with English-language translation, 7 pages.
Written Opinion of the International Searching Authority (Form PCT/ISA/237) for International Patent Application No. PCT/CN2019/122503, issued from the International Searching Authority, dated Mar. 9, 2020, with English-language translation, 10 pages.

* cited by examiner

*Primary Examiner* — Joseph K McKane
*Assistant Examiner* — Meghan C Heasley
(74) *Attorney, Agent, or Firm* — Ice Miller LLP

(57) ABSTRACT

The invention provides compounds of formula (I) as shown below, including their possible enantiomers and diastereomers, as well as pharmaceutically acceptable salts, hydrates or solvates thereof. The invention also provides pharmaceutical compositions of these compounds, methods for their preparation, and their use in the treatment of diseases and disorders (including cancers).

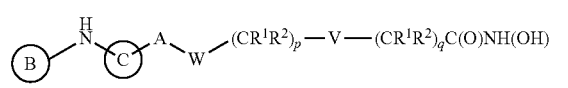

10 Claims, No Drawings

HETEROCYCLIC COMPOUND AS CDK-HDAC DOUBLE-CHANNEL INHIBITOR

CROSS-REFERENCE TO RELATED APPLICATIONS

This application is a section 371 of International Application No. PCT/CN2019/122503 filed Dec. 2, 2019, which was published in the Chinese language Apr. 6, 2020, under International Publication No. WO 2020/108661A1, the disclosure of which is incorporated herein by reference in its entirety.

BACKGROUND OF THE INVENTION

Cyclin-dependent kinases (CDKs) are protein kinases involved in important cellular processes, such as cell cycle or transcription regulation. There are 13 CDKs and different CDKs responsible for the activation of the cell cycle of quiescent cells, as well as for the progression of the cell cycle from G1 to mitosis. Each of the CDKs controls a specific checkpoint of the cell cycle. CDKs are activated by the binding to the cyclins and thus form specific complexes. In many human cancers, CDKs are overactive or CDK-inhibiting proteins are not functional. Therefore, it is rational to target CDK function to prevent unregulated proliferation of cancer cells (*Nature Reviews,* 2009, 9, 153-166). For example, CDK4 is the key regulator of the G1-S transition. In complex with Cyclin D, CDK4 phosphorylates Rb and drives cell cycle progression, a process inhibited by p16. The p16-CDK4-cyclin D-Rb is aberrant in the majority of cancers and thus is an attractive target for anti-cancer therapy.

At present, US FDA has approved two CDK4/6 selective inhibitors Palbociclib (Pfizer) and Ribocicilib (Novatis) for the first line treatment of HR+/HER2− advanced breast cancer. Besides strongly inhibiting CDK4 and CDK6, Abemaciclib developed by Lilly also inhibits other CDKs like CDK2. In September 2017, FDA approved Abemaciclib for the treatment of some breast cancers in America. There are many cell cycling modulators entering into clinical studies now.

Histone deacetylases (HDACs) are a class of enzymes that remove the acetyl group from the ε-amino groups of lysine residues located in the $NH_2$ terminal tails of core histones. There are 18 known human histone deacetylases, grouped into four classes based on the structure of their accessory domains. Class I includes HDAC1, HDAC2, HDAC3 and HDAC8 and have homology to yeast RPD3. HDAC4, HDAC5, HDAC7 and HDAC9 belong to class II, and have homology to yeast HDA1. HDAC6 and HDAC10 contain two catalytic sites and are classified as class IIa, whereas HDAC11 has conserved residues in its catalytic center that are shared by both class I and class II deacetylases and is sometimes placed in class IV. Histone deacetylase inhibitors (HDACIs) are emerging as a new class of potential anticancer agents and have been shown to induce differentiation, cell-cycle arrest and apoptosis, and to inhibit migration, invasion and angiogenesis in many cancer cell lines. In addition, HDAC inhibitors inhibit tumor growth in animal models and show antitumor activity in patients.

There is also growing evidence that HDAC inhibitors have potential therapeutic application in nonmalignant diseases, such as for treatment of inflammatory and neurodegenerative diseases.

Study has shown that pan-HDAC inhibitor could effectively induce cell cycle arrest in G1 phase in many lung cancer cell lines, thus inhibiting cell proliferation. This inhibitor significantly reduced the protein levels of CyclinD1, CDK2 and CDK4 in cells, and upregulated the expression of P21WAF1/CIP1 and cyclin E. Further experiments proved this inhibitor suppresses the activity of HDAC6 through down regulating its expression. Pan-HDAC inhibitor induced super acetylation of HSP90 in lung cancer cells, thus increasing the cellular degradation of CyclinD1 and CDK4.

Another study demonstrates that Retinoblastoma (Rb) could form nucleosome remodeling complex with HDAC and hSWI/SNF, inhibit the transcription of CyclinE and CyclinA, and induce cell cycle arrest in G1 phase. Rb phosphorylation catalyzed by CyclinD1/CDK4 prevents it from interacting with HDAC, leading to the release of CyclinE expression repression and G1 cell cycle arrest. Renier Heijkants et al. reported that combined inhibition of CDK and HDAC is a promising therapeutic strategy for the treatment of cutaneous and uveal metastatic melanoma.

In summary, small molecule CDK inhibitors (which inhibit one or more subtypes of CDK) can be used to treat many different cancers. In particular, a single small molecule designed to inhibit CDK and HDAC at the same time has novelty and may have a synergetic effect in the treatment of cancer.

On the other hand, study has reported that CDK inhibitors can also be used in combination with other targeted antitumor drugs or antibodies, which have synergetic effects on cancer treatment. The CDK-HDAC dual-pathway inhibitor can also be used in combination with other targeted antitumor drugs or antibodies, and such a combination treatment scheme provides the possibility of acting on multiple targets at the same time, thus reducing the clinical complexity and technical problems of using single CDK inhibitor+single HDAC inhibitor+targeted anticancer drugs (or antibodies). The combination of CDK-HDAC dual pathway inhibitor and other targeted antitumor drugs (or antibodies) can delay the generation of drug resistance and increase the anti-tumor effect, which has certain advantages in the treatment of various cancers. In summary, there is a need in the art to provide novel CDK-HDAC dual pathway inhibitors.

SUMMARY OF THE INVENTION

The present invention provides novel heterocyclic compounds and their uses, for example as protein kinase inhibitors (such as CDKs) and HDACs. In particular, the compound of the patent of the present invention can simultaneously inhibit different subtypes of CDK and different subtypes of HDAC.

The present invention provides a compound of molecular formula (I), its diastereomers or enantiomers, when possible, comprise its deuterated derivatives, and/or its corresponding pharmaceutically acceptable salts, prodrugs, hydrates, and solvate thereof.

The compound of formula (I) shown below, its deuterium derivative at any available position of the molecule, its diastereomers and enantiomers (where possible):

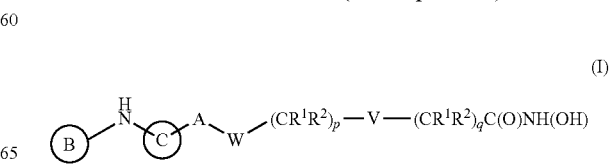

(I)

or the pharmaceutically acceptable salts, prodrugs, hydrates solvates thereof, wherein:

Ⓑ is formula (II):

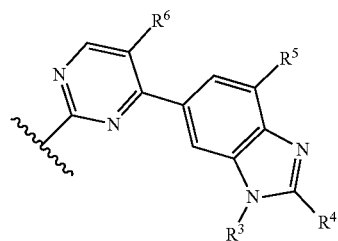

(II)

Ⓒ is phenyl ring, 5- to 6-membered monocyclic heteroaromatic ring, wherein the mono-heteroaromatic ring described herein may optionally comprise 1 to 3 heteroatoms independently selected from N, O and S;

"⌇⌇⌇" represents the attaching site of formula (II) to NH of Ⓒ in the formula (I);

A is a bond, —O—, —C(O)—, —$(CR^{10}R^{11})_m$—, —$N(R^{12})$—, $C_{3-8}$ cycloalkane structure, 3 to 9-membered heterocyclic ring (optionally containing 1-3 heteroatoms selected from N, O or S), aryl, or heteroaryl; the cycloalkane structure, heterocyclic ring, aryl and heteroaryl can be optionally and independently substituted by 0-4 substituents selected from the group consisting of hydroxy, halogen, $C_{1-4}$ alkyl, $C_{1-4}$ haloalkyl, cyano, provided that the chemical structure formed being stable and meaningful. When two hydroxyl groups are both connected to the same carbon atom on the cycloalkane structure or heterocyclic ring, it means that the two hydroxyl groups and the carbon atom form a carbon group (ie —C(O)—) structure;

W is chemical bond, —C(O)—, —$(CR^{10}R^{11})_m$—, —$(CR^{10}R^{11})_mNR^{12}$—, —$N(R^{12})$—, —OC(O)—, —C(O)O—, —C(O)NH—, —NHC(O)—, —$S(O)_2$—, —$S(O)_2NH$—, —$NHS(O)_2$—, $C_{3-8}$ cycloalkane structure, 3 to 9-membered heterocycle (optionally containing 1-3 heteroatoms selected from N, O or S), aromatic ring, or heteroaromatic ring; with the proviso that Ⓒ, A, W, V, $R^1$, $R^2$, p and q together form a stable chemical structure; when A and W are both bond, $(CR^1R^2)_p$—V—$(CR^1R^2)_qC(O)NH(OH)$ is directly connected to Ⓒ;

each $R^1$ and $R^2$ is independently hydrogen, deuterium, halogen, or $C_{1-4}$ alkyl;

or $R^1$ and $R^2$ together with the carbon atom they attached to form a 3- to 9-membered cyclic structure which optionally containing 0-3 additional heteroatoms selected from N, O or S); or $R^1$ and $R^2$ together with the carbon atom they attached to form carbonyl (i.e., $CR^1R^2$ is C(O));

$R^3$ is independently hydrogen, $C_{1-8}$ alkyl, $C_{3-8}$ cycloalkyl, 3- to 9-membered heterocyclic group (optionally containing 1-3 heteroatoms selected from N, O or S), or $C_{3-8}$ cycloalkylmethyl;

$R^4$ is independently hydrogen, deuterium, $C_{1-8}$ alkyl, $C_{2-8}$ alkenyl, $C_{2-8}$ alkynyl, $C_{3-8}$ cycloalkyl, or 3- to 9-membered heterocyclic group (optionally containing 1-3 heteroatoms selected from N, O, or S);

each of $R^5$ and $R^6$ is independently hydrogen, deuterium, halogen, $C_{1-8}$ alkyl, $C_{2-8}$ alkenyl, $C_{2-8}$ alkynyl, $C_{3-8}$ cycloalkyl, or 3- to 9-membered heterocyclic (optionally containing 1-3 heteroatoms selected from N, O, or S); wherein at least one of $R^5$ and $R^6$ is fluorine;

each of $R^{10}$ and $R^{11}$ is independently hydrogen, deuterium, halogen, $C_{1-4}$ alkyl, $C_{2-4}$ alkenyl, $C_{2-4}$ alkynyl, $C_{3-8}$ cycloalkyl, 3- to 9-membered heterocyclic (optionally containing 1-3 heteroatoms selected from N, O, or S), aryl, or heteroaryl;

or $R^{10}$ and $R^{11}$ together with the carbon atom they attached form a 3- to 9-membered cyclic structure which optionally containing 0-3 additional heteroatoms each independently selected from N, O, or S;

$R^{12}$ is hydrogen, $C_{1-4}$ alkyl, $R^{13}C(O)$—, $R^{13}S(O)_2$—, $C_{3-8}$ cycloalkyl, 3- to 9-membered heterocyclic group (optionally containing 1-3 heteroatoms selected from N, O and S), aryl, or heteroaryl; wherein $R^{13}$ is hydrogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O, and S), aryl, or heteroaryl;

V is —$CR^{14}R^{15}$—, —CH=CH—, —C≡C—, —O—, —S—, —$N(R^{12})$—, —C(O)—, —OC(O)—, —C(O)O—, —OC(O)O—, —C(O)NH—, —NHC(O)—, —NHC(O)NH—, —S(O)—, —$S(O)_2$—, —$S(O)_2NH$—, —$NHS(O)_2$—, $C_{3-8}$cycloalkene structure, 3- to 9-membered heterocyclic group (optionally containing 1-3 heteroatoms selected from N, O or S), aryl, heteroaryl, or —$V^1(CR^1R^2)_tV^2$—;

wherein $R^{14}$ and $R^{15}$ are each independently hydrogen, deuterium, halogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O or S), aryl, heteroaryl, —CN, —$OR^{16}$, —$SR^{16}$, —$N(R^{17})_2$, —$C(O)R^{13}$, —$C(O)OR^{16}$, —$C(O)N(R^{17})_2$, —$OC(O)R^{13}$, —$NR^{17}C(O)R^{13}$, or —$S(O)_2R^{13}$; or $R^{14}$ and $R^{15}$ together with the carbon atom they attached to form a 3- to 9-membered cyclic which optionally containing 0-3 additional heteroatoms selected from N, O or S); wherein $R^{16}$ is hydrogen, $C_{1-4}$ alkyl, $C_{3-8}$ cycloalkyl, 3- to 9-membered heterocyclic group (optionally containing 1-3 heteroatoms selected from N, O or S), aryl, or heteroaryl; each $R^{17}$ is hydrogen, $C_{1-4}$ alkyl, $C_{3-8}$ cycloalkyl, 3- to 9-membered heterocyclic group (optionally containing 1-3 heteroatoms selected from N, O or S), aryl, or heteroaryl; or two $R^{17}$ together with the nitrogen atom they attached to form a 3- to 9-membered cyclic structure which optionally containing 0-3 additional heteroatoms selected from N, O, or S;

$V^1$ and $V^2$ are each independently bond, —$CR^{14}R^{15}$—, —CH=CH—, —C≡C—, —O—, —S—, —$N(R^{12})$—, —C(O)NH—, —NHC(O)—, —$S(O)_2$—, —$S(O)_2NH$—, —$NHS(O)_2$—, $C_{3-8}$ cycloalkyl structure, 3- to 9-membered heterocyclic group (optionally containing 1-3 heteroatoms selected from N, O, or S), aryl, or heteroaryl;

p and q are each independently 0, 1, 2, 3, 4, 5, 6, 7, 8, 9 or 10;

m is 0, 1, 2, 3, or 4;

t is 0, 1, 2, 3, 4, or 5;

with the proviso that the group formed by V, $V^1$, $V^2$, p, q, and t is chemically stable structure;

each of the above alkyl, alkenyl, alkynyl, cycloalkyl, heterocyclyl, aryl, heteroaryl, cycloalkane structure, heterocyclic, aromatic cyclic and heteroaryl cyclic are optionally and each independently substituted by 1-3 substituents selected from the group consisting of deuterium, halogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O or S), aryl, heteroaryl, —CN, —NO$_2$, —OR$^{16}$, —SR$^{16}$, —N(R$^{17}$)$_2$, —C(O)R$^{13}$, —C(O)OR$^{16}$, —C(O)N(R$^{17}$)$_2$, —SO$_2$N(R$^{17}$)$_2$; wherein R$^{16}$ is hydrogen, $C_{1-4}$ alkyl, $C_{3-8}$ cycloalkyl, 3- to 9-membered heterocyclic group (optionally containing 1-3 heteroatoms selected from N, O or S), aryl, or heteroaryl; each R$^{17}$ is hydrogen, $C_{1-4}$ alkyl, $C_{3-8}$ cycloalkyl, 3- to 9-membered heterocyclic group (optionally containing 1-3 heteroatoms selected from N, O or S), aryl, or heteroaryl; or two R$^{17}$ together with the nitrogen atom they attached to form a 3- to 9-membered cyclic structure which optionally containing 0-3 additional heteroatoms selected from N, O or S; the other groups are defined as above;

unless otherwise specified, the aryl above comprises 6 to 12 carbon atoms; the heteroaryl is 5- to 15-membered heteroaryl group.

In another preferred embodiment,

A is bond, —O—, —C(O)—, —(CR$^{10}$R$^{11}$)$_m$—, —N(R$^{12}$)—, 3- to 9-membered heterocyclic ring (optionally containing 1-3 heteroatoms selected from N, O and S), or heteroaryl; the heterocyclic ring or heteroaryl can be optionally and independently substituted with 0-4 substituents selected from the group consisting of hydroxyl, halogen, $C_{1-4}$ alkyl, $C_{1-4}$ haloalkyl, cyano, with the proviso that the chemical structure formed is stable and meaningful. when two hydroxyl groups are both connected to the same carbon atom on the heterocyclic ring, it means that the two hydroxyl groups and the carbon atom form a carbon group (ie —C(O)—) structure;

W is bond, —O—, —C(O)—, —(CR$^{10}$R$^{11}$)$_m$—, —(CR$^{10}$R$^{11}$)$_m$NR$^{12}$—, —N(R$^{12}$)—, —OC(O)—, —C(O)O—, —C(O)NH—, —NHC(O)—, —S(O)$_2$—, —S(O)$_2$NH—, —NHS(O)$_2$—, 3- to 9-membered heterocyclic group (optionally containing 1-3 heteroatoms selected from N, O, and S), or heteroaryl; with the proviso that ⓒ, A, W, V, R$^1$, R$^2$, p and q together forms a chemical stable structure; when A and W are both bond, (CR$^1$R$^2$)$_p$—V—(CR$^1$R$^2$)$_q$C(O)NH(OH) directly link to ⓒ;

each R$^1$ and R$^2$ is independently hydrogen, deuterium, halogen, or $C_{1-4}$ alkyl;

or R$^1$ and R$^2$ together with the carbon atom they attached to form a 3- to 9-membered cyclic structure which optionally containing 0-3 additional heteroatoms selected from N, O or S); or R$^1$ and R$^2$ together with the carbon atom they attached to form carbonyl (i.e., CR$^1$R$^2$ is C(O));

R$^3$ is hydrogen, $C_{1-8}$ alkyl, $C_{3-8}$ cycloalkyl, or $C_{3-8}$ cycloalkylmethyl;

R$^4$ is hydrogen, deuterium, $C_{1-8}$ alkyl, $C_{3-8}$ cycloalkyl;

R$^5$ and R$^6$ are each independently hydrogen, deuterium, halogen or $C_{1-8}$ alkyl; wherein at least one of R$^5$ and R$^6$ is fluorine;

each R$^{10}$ and R$^{11}$ are independently hydrogen, deuterium, halogen, or $C_{1-4}$ alkyl;

or R$^{10}$ and R$^{11}$ together with the carbon atom they attached form a 3- to 9-membered cyclic structure which optionally containing 0-3 additional heteroatoms each independently selected from N, O or S;

R$^{12}$ is hydrogen, $C_{1-4}$ alkyl, R$^{13}$C(O)—, R$^{13}$S(O)$_2$—, $C_{3-8}$ cycloalkyl, 3- to 9-membered heterocyclic group (optionally containing 1-3 heteroatoms selected from N, O and S), aryl, or heteroaryl; wherein R$^{13}$ is hydrogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O and S), aryl, or heteroaryl;

V is bond, —CR$^{14}$R$^{15}$—, —CH═CH—, —C≡C—, —O—, —S—, —N(R$^{12}$)—, —C(O)—, $C_{3-8}$ cycloalkane structure, 3- to 9-membered heterocyclic group (optionally containing 1-3 heteroatoms selected from N, O and S), aryl, heteroaryl, or —V$^1$(CR$^1$R$^2$)$_t$V$^2$—;

wherein, R$^{14}$ and R$^{15}$ are each independently hydrogen, deuterium, halogen, $C_{1-4}$ alkyl; or R$^{14}$ and R$^{15}$ together with the carbon atom they attached form a 3- to 9-membered ring which optionally have 0-3 additional heteroatoms each independently selected from N, O and S;

V$^1$ and V$^2$ are each independently bond, —CR$^{14}$R$^{15}$—, —CH═CH—, —C≡C—, —O—, —S—, —N(R$^{12}$)—, —C(O)NH—, $C_{3-8}$ cycloalkyl structure, 3- to 9-membered heterocyclic group (optionally containing 1-3 heteroatoms selected from N, O and S), aryl, or heteroaryl;

each of the above alkyl, alkenyl, alkynyl, cycloalkyl, heterocyclyl, aryl, heteroaryl, cycloalkane structure, heterocyclic, aromatic cyclic and heteroaryl cyclic are optionally and each independently substituted by 1-3 substituents selected from the group consisting of deuterium, halogen, $C_{1-4}$ alkyl, $C_{2-4}$ alkenyl, $C_{2-4}$ alkynyl, $C_{3-8}$ cycloalkyl, 3- to 9-membered heterocyclic group (optionally containing 1-3 heteroatoms selected from N, O or S), aryl, heteroaryl, —CN, —NO$_2$, —OR$^{16}$, —SR$^{16}$, —N(R$^{17}$)$_2$, —C(O)R$^{13}$, —C(O)OR$^{16}$, —C(O)N(R$^{17}$)$_2$, —SO$_2$N(R$^{17}$)$_2$; wherein R$^{13}$ is as defined above; R$^{16}$ is hydrogen, $C_{1-4}$ alkyl, $C_{3-8}$ cycloalkyl, 3- to 9-membered heterocyclic group (optionally containing 1-3 heteroatoms selected from N, O or S), aryl, or heteroaryl; each R$^{17}$ is hydrogen, $C_{1-4}$ alkyl, $C_{3-8}$ cycloalkyl, 3- to 9-membered heterocyclic group (optionally containing 1-3 heteroatoms selected from N, O or S), aryl, or heteroaryl; or two R$^{17}$ together with the nitrogen atom they attached to form a 3- to 9-membered cyclic structure which optionally containing 0-3 additional heteroatoms selected from N, O, or S;

In another preferred example, groups in formula (II) are defined as follows: R$^3$ is $C_{1-8}$ alkyl, $C_{3-8}$ cycloalkyl, or $C_{3-8}$ cycloalkylmethyl; R$^4$ is hydrogen, $C_{1-8}$ alkyl, $C_{2-8}$ alkenyl, $C_{2-8}$ alkynyl, $C_{3-8}$ cycloalkyl; R$^5$ and R$^6$ are each independently hydrogen, halogen, $C_{1-8}$ alkyl, $C_{2-8}$ alkenyl, $C_{2-8}$ alkynyl, $C_{3-8}$ cycloalkyl; wherein at least one of R$^5$ or R$^6$ is fluorine.

In another preferred example, in formula (II), R$^3$ is isopropyl, R$^4$ is methyl, R$^5$ is fluorine, and R$^6$ is fluorine; i.e., Ⓑ is.

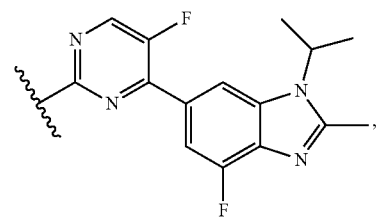 [SMILES: *c1ncc(F)c(-c2cc(F)c3nc(C)n(C(C)C)c3c2)n1]

wherein "  " means the connecting site of Ⓑ to NH on Ⓒ.

In another preferred example, Ⓒ is a benzene ring or a pyridine ring.

In another preferred example, A is bond, —O—, —C(O)—, —CH$_2$—, —N(R$^{12}$)—, 3- to 9-membered heterocyclic group (optionally containing 1-3 heteroatoms selected from N, O, S), or heteroaryl; W is bond, —C(O)—, —CH$_2$—, —N(R$^{12}$)—, —C(O)NH—, —S(O)$_2$—, 3- to 9-membered heterocyclic ring (optionally containing 1-3 heteroatoms selected from N, O, and S).

In another preferred example, A and W are both bonds, in this case, (CR$^1$R$^2$)$_p$—V—(CR$^1$R$^2$)$_q$C(O)NH(OH) directly connect to Ⓒ.

In another preferred example, R$^1$ and R$^2$ are each independently hydrogen or C$_{1-4}$ alkyl; p and q are each independently 0, 1, 2, 3, 4, 5, or 6.

In another preferred example, V is selected from the group consisting of bond, —CH$_2$—, —CH=CH—, —C≡C—, —O—, —S—, —N(R$^{12}$)—, C$_{3-8}$ cycloalkane structure, 3- to 9-membered heterocyclic ring (optionally containing 1-3 heteroatoms selected from N, O and S), aryl, heteroaryl, or —V$^1$(CR$^1$R$^2$)$_t$V$^2$—;

In another preferred example, V$^1$ and V$^2$ are each independently bond, —CH$_2$—, —CH=CH—, —C≡C—, —O—, —S—, —N(R$^{12}$)—, C$_{3-8}$ cycloalkane structure, 3- to 9-membered heterocycle (optionally containing 1-3 heteroatoms selected from N, O and S), aryl, or heteroaryl; t is 0, 1, 2, or 3.

In another preferred example, the combination of A and W

is selected from the following groups:
bond

wherein 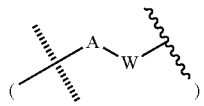 the connecting point to (CR$^1$R$^2$)$_p$—V—(CR$^1$R$^2$)$_q$C(O)NH(OH),  is the connecting site to Ⓒ, R$^{12}$ is as defined above.

In another preferred embodiment, the combination of A, W and (CR$^1$R$^2$)$_p$—V—(CR$^1$R$^2$)$_q$C(O)NH(OH), i.e,

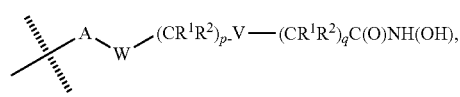

is selected from the following groups:

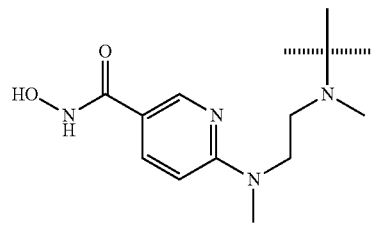

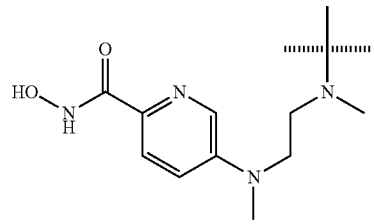

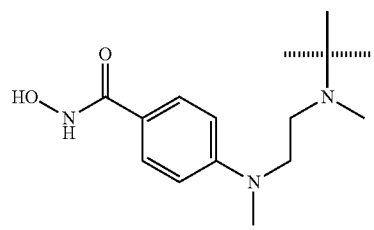

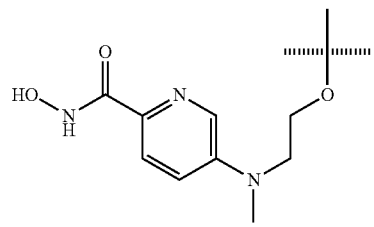

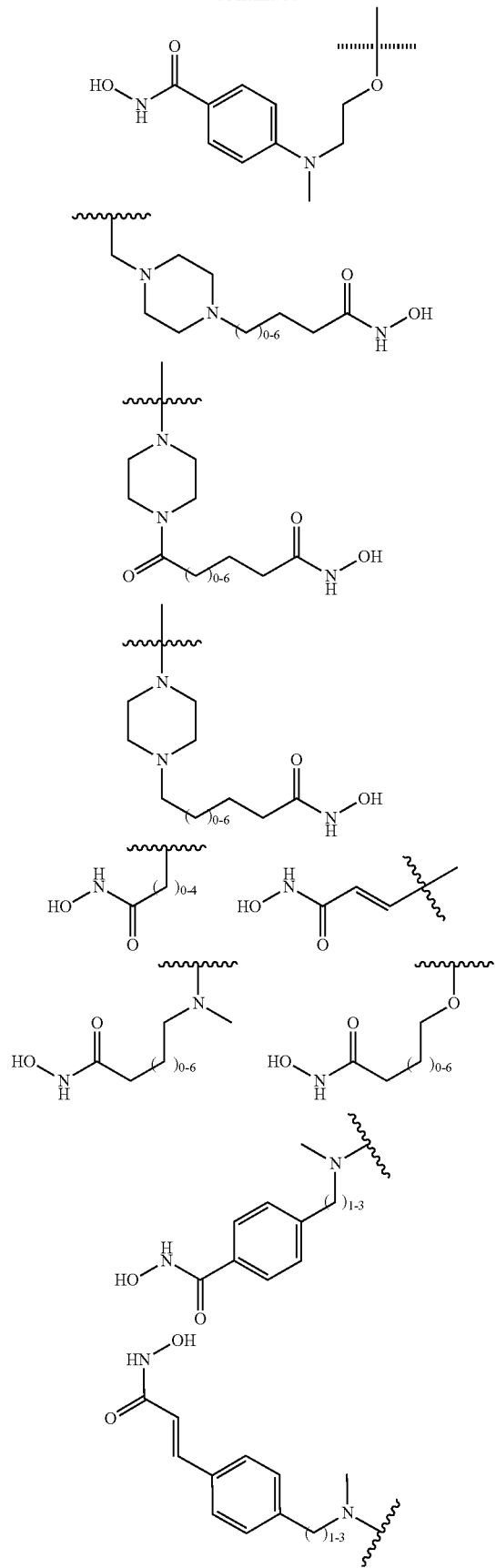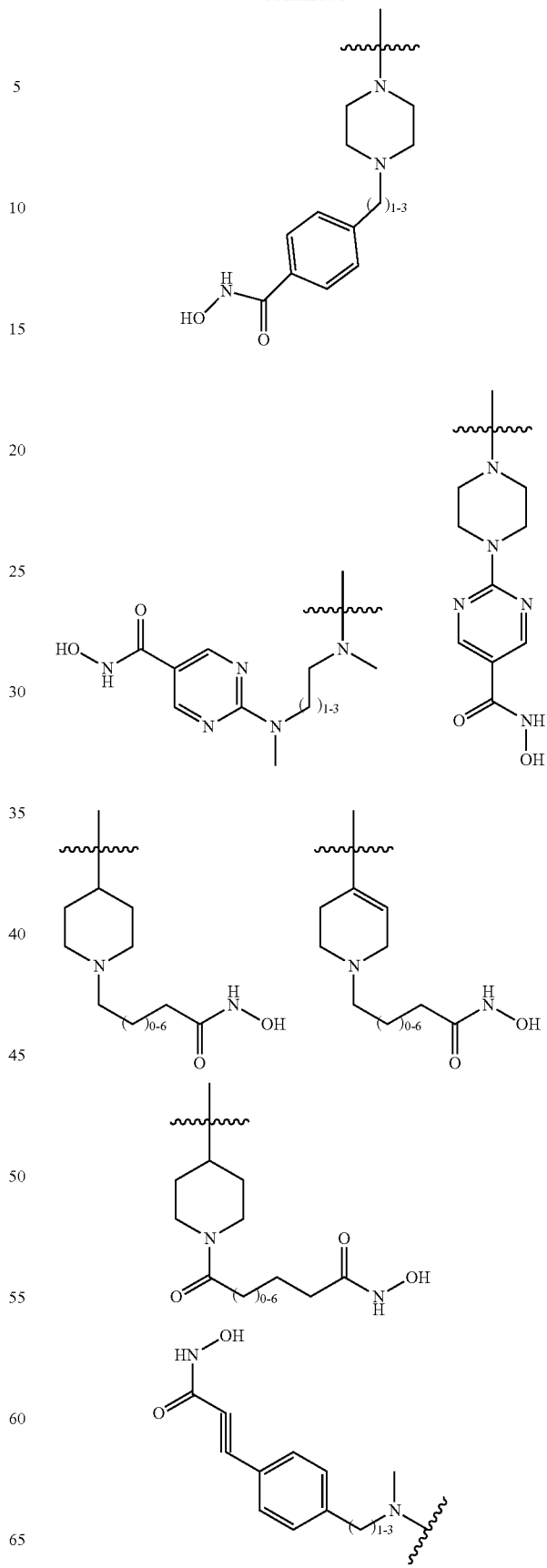

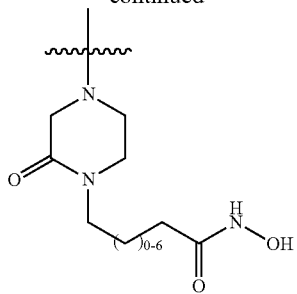
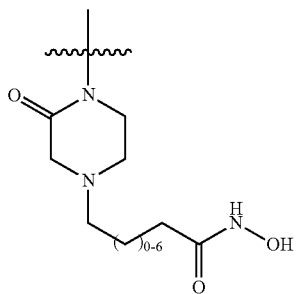
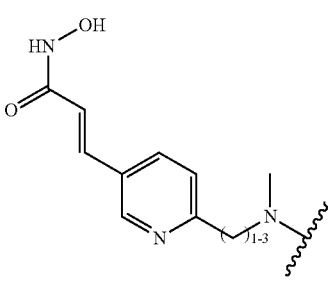
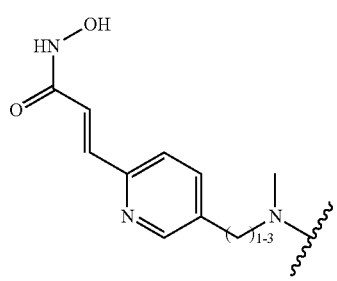
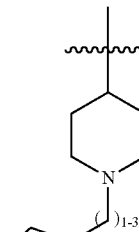 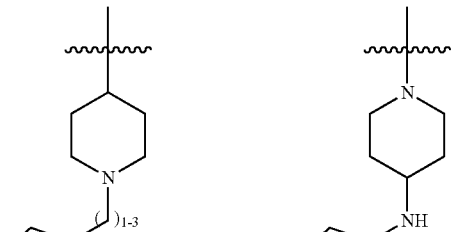
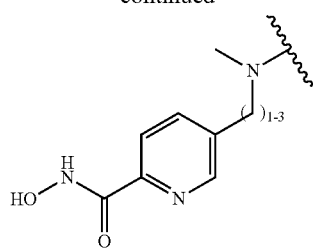
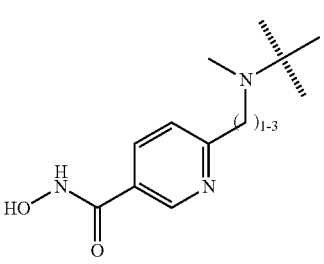
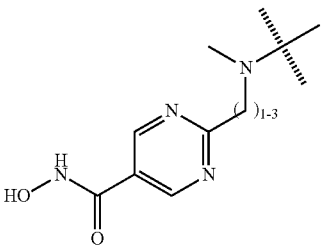
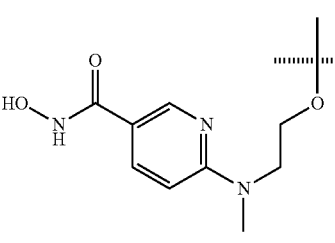
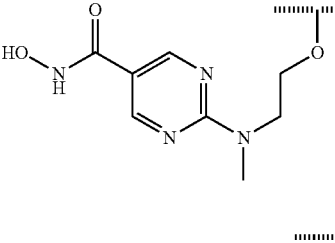
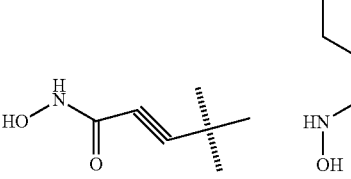

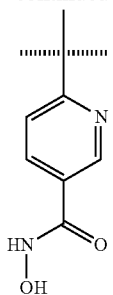
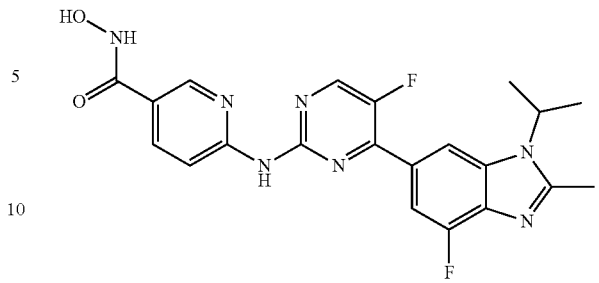
wherein ⌇ is the connecting point to ⓒ.
In another preferred embodiment, the compound of formula (I) is:
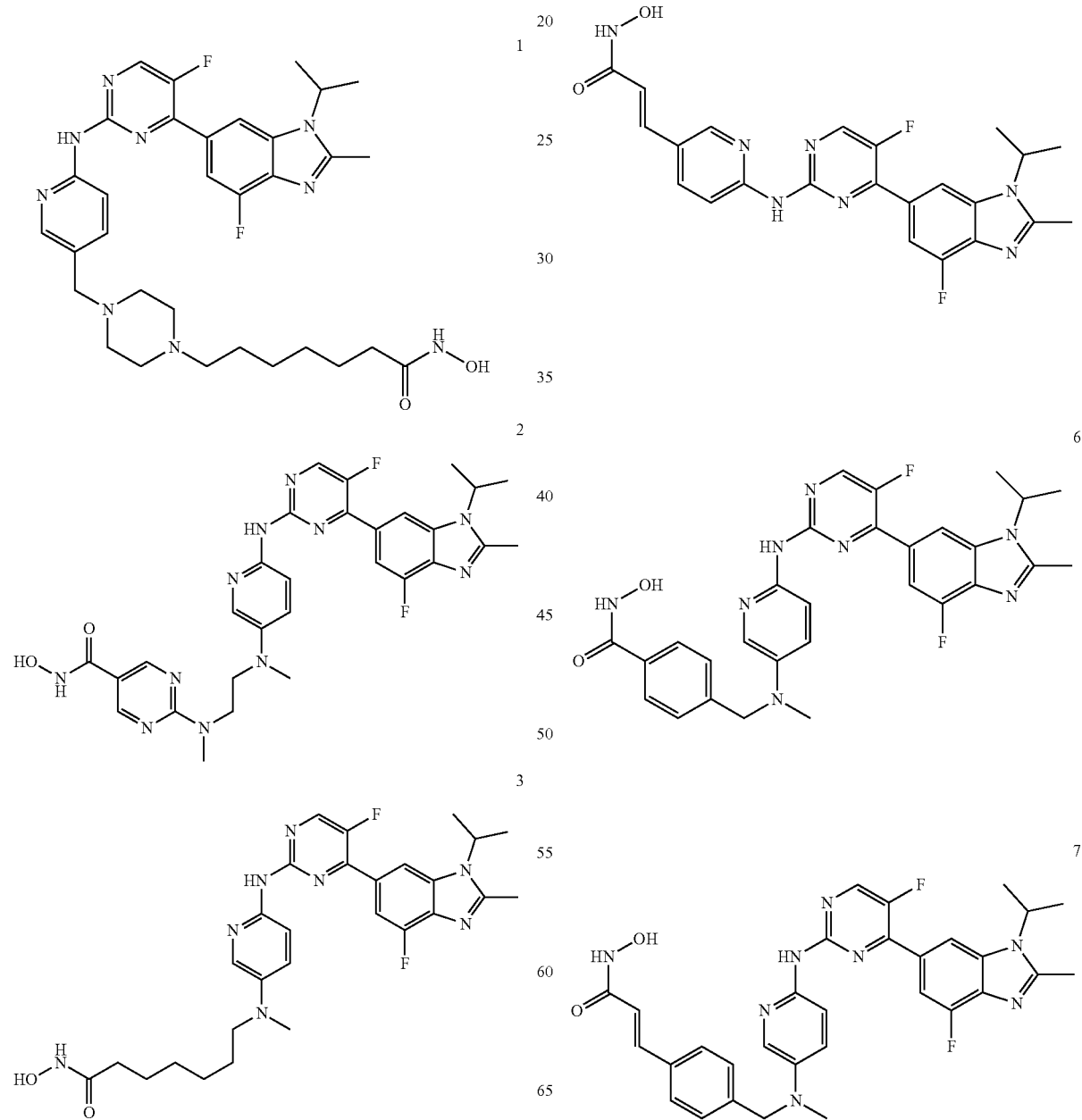

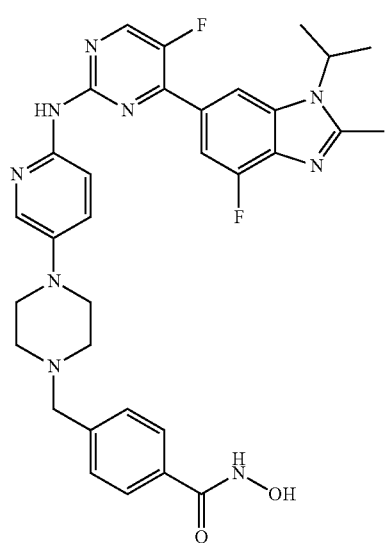
8
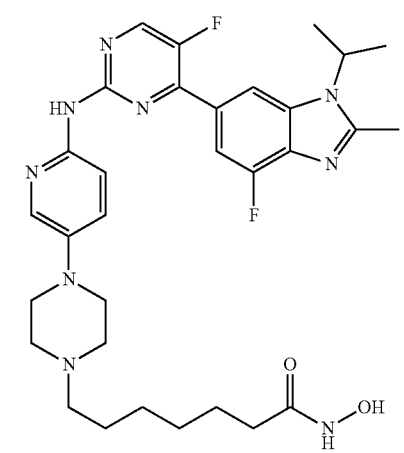
9
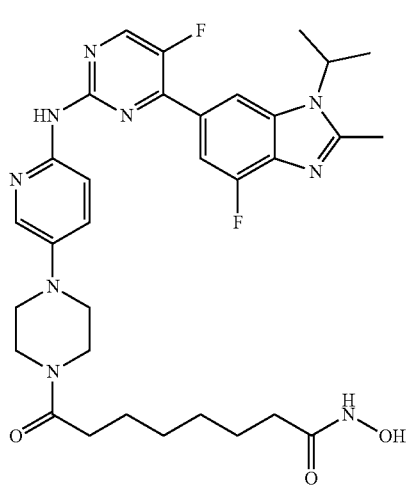
10
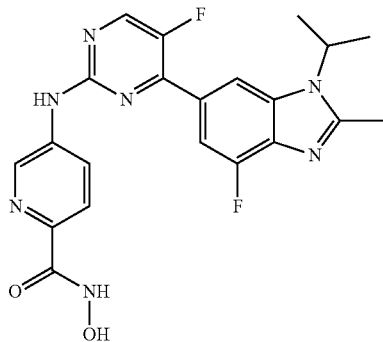
11
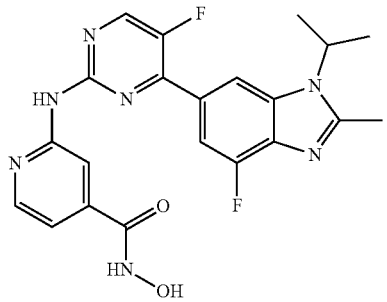
12
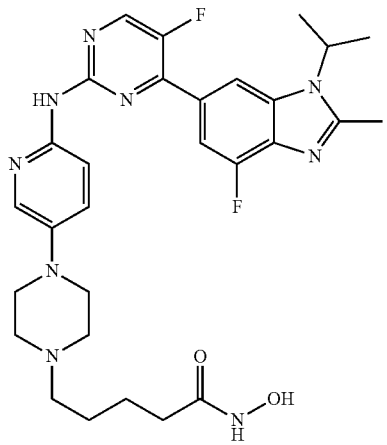
13
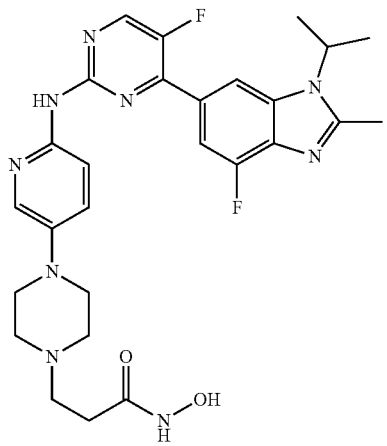
14

17
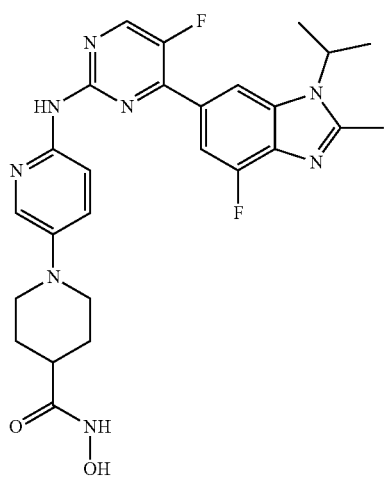
16
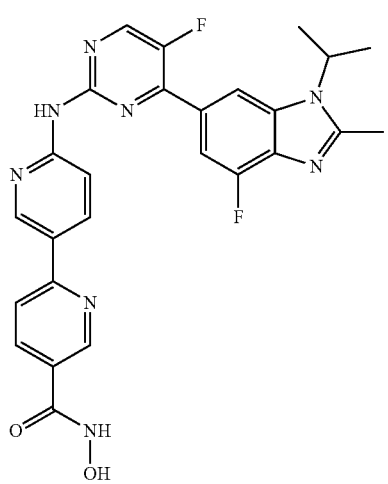
17
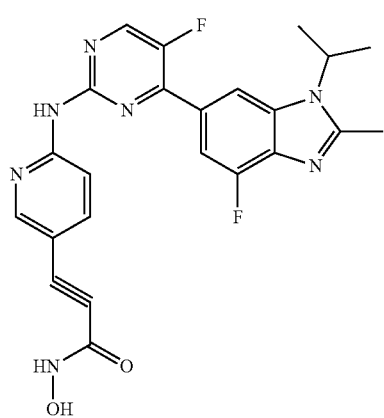
15
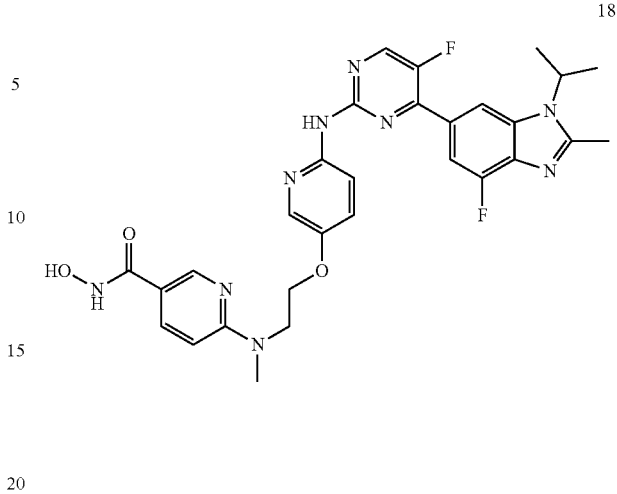
18
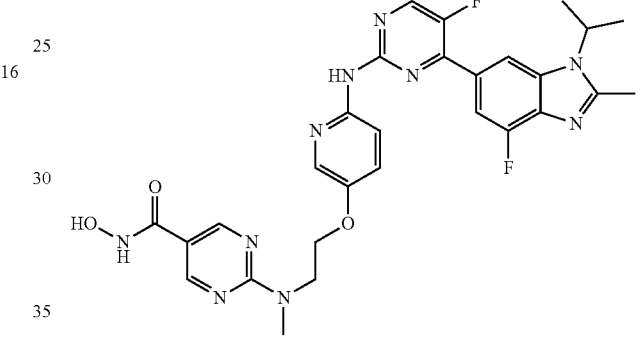
19
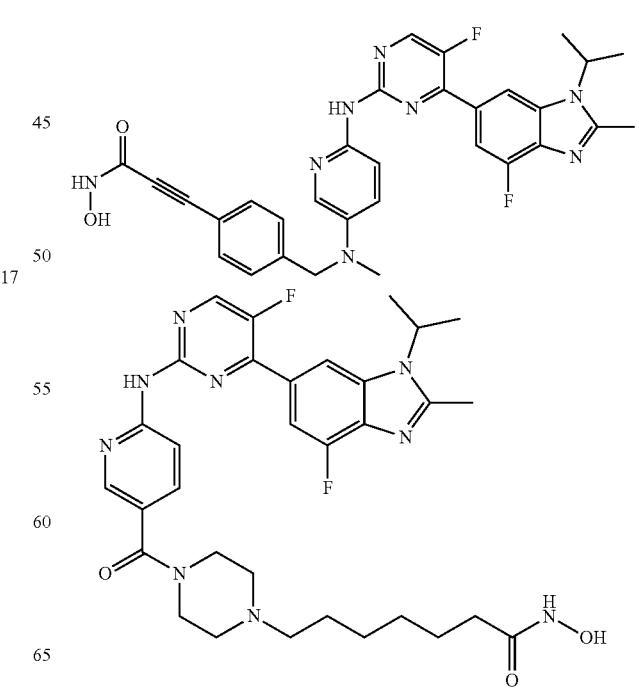

19
-continued
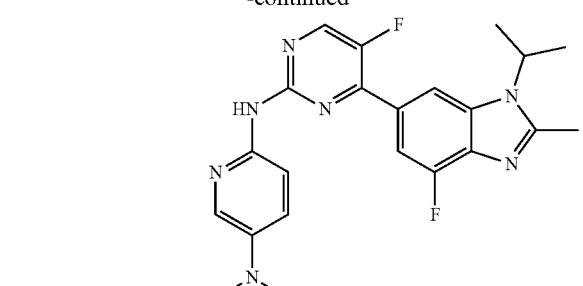
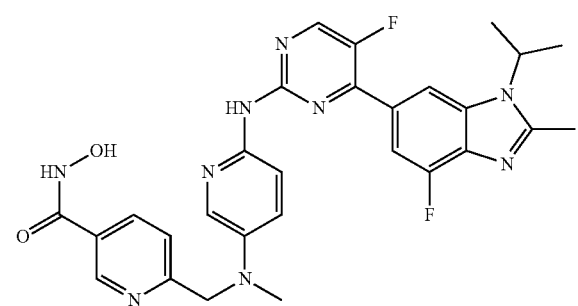
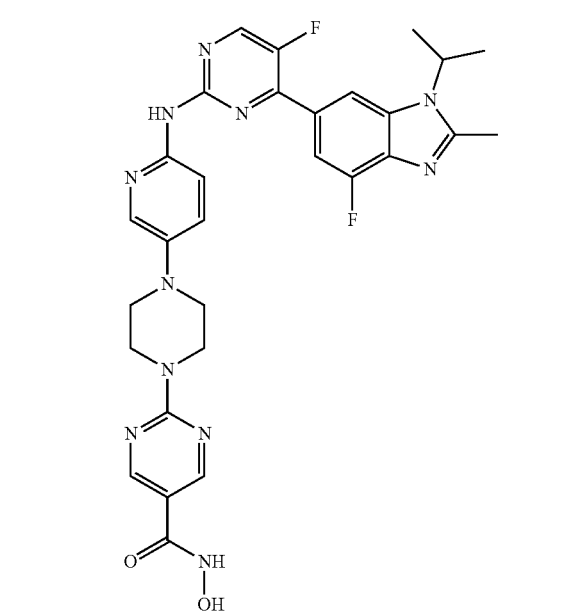
20
-continued
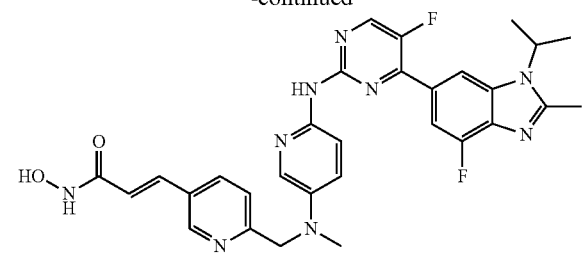
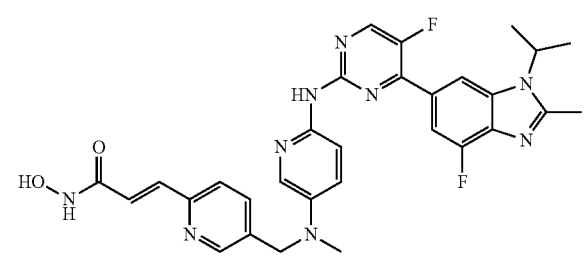
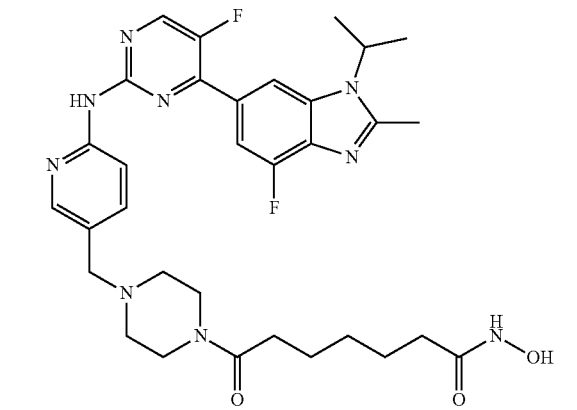
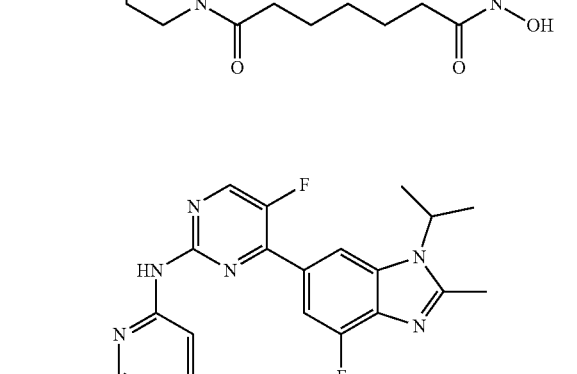
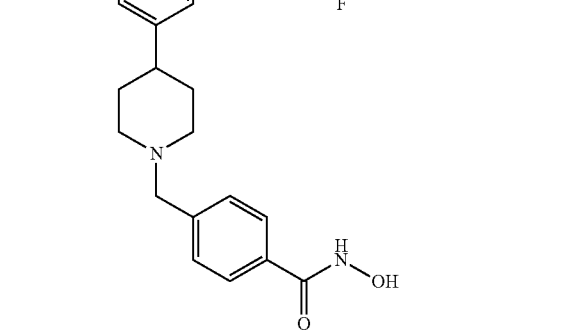
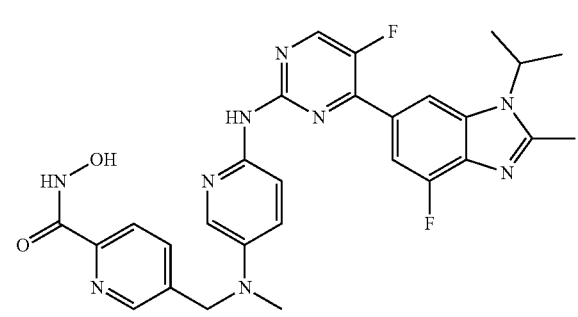

-continued
21
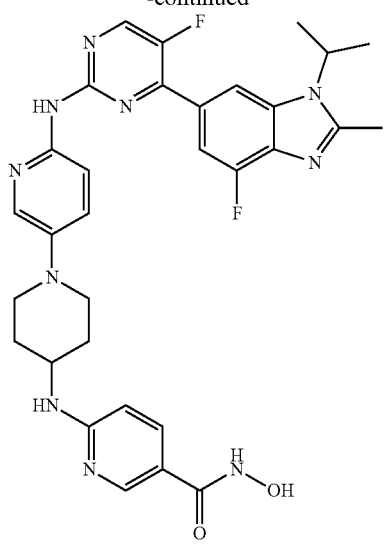
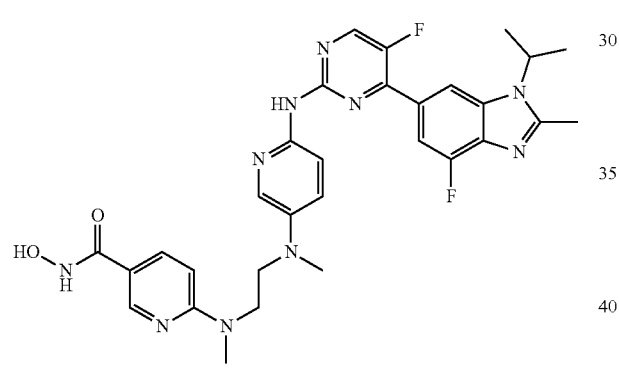
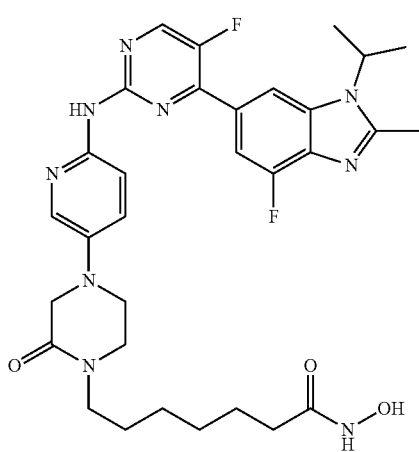
-continued
22
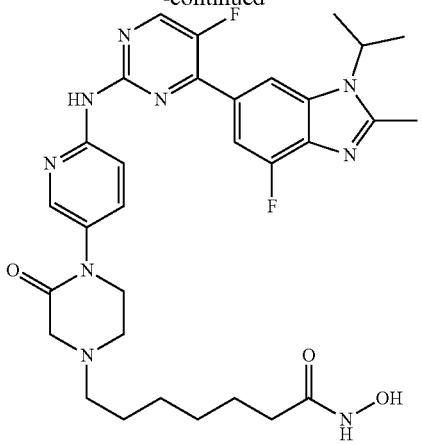
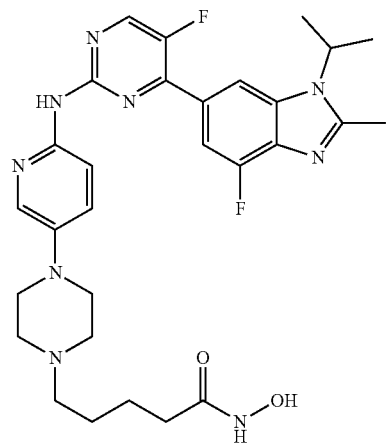
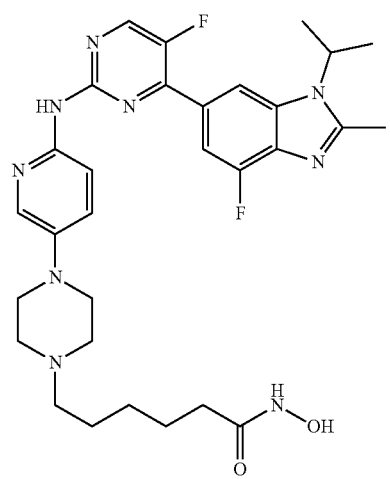

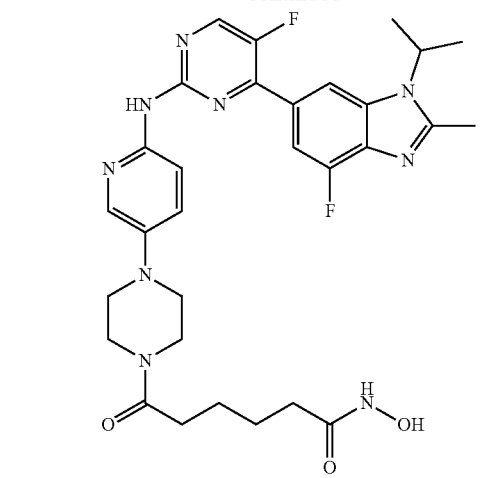
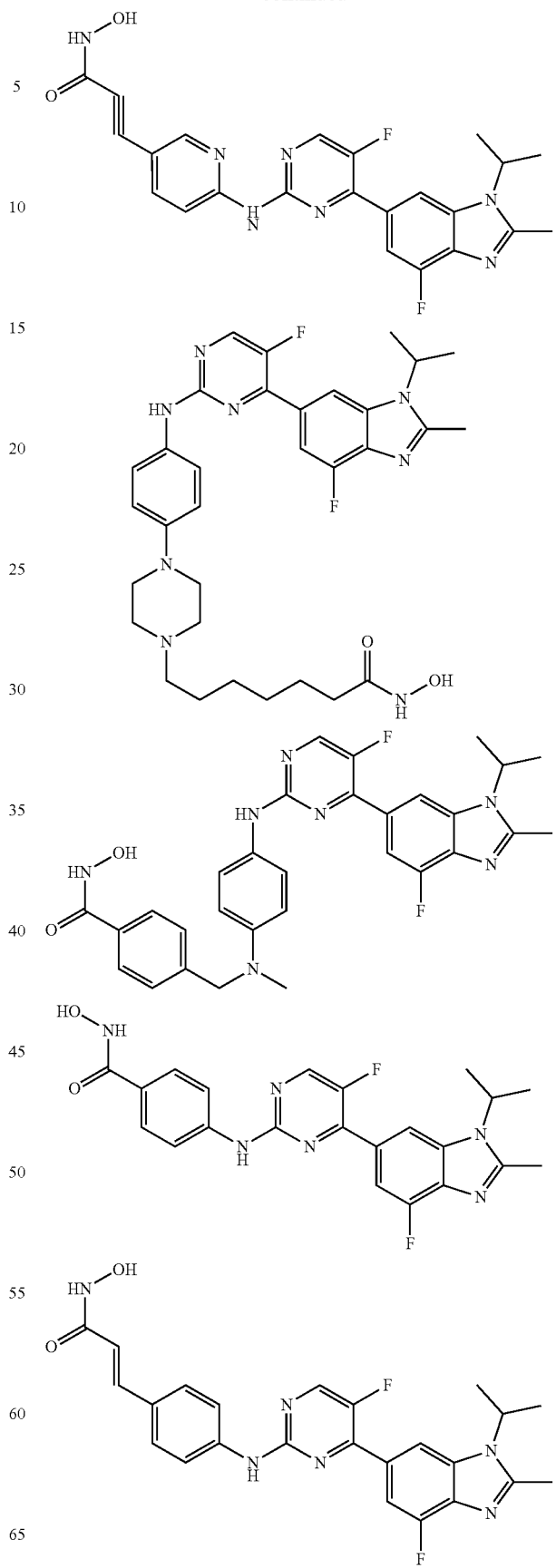

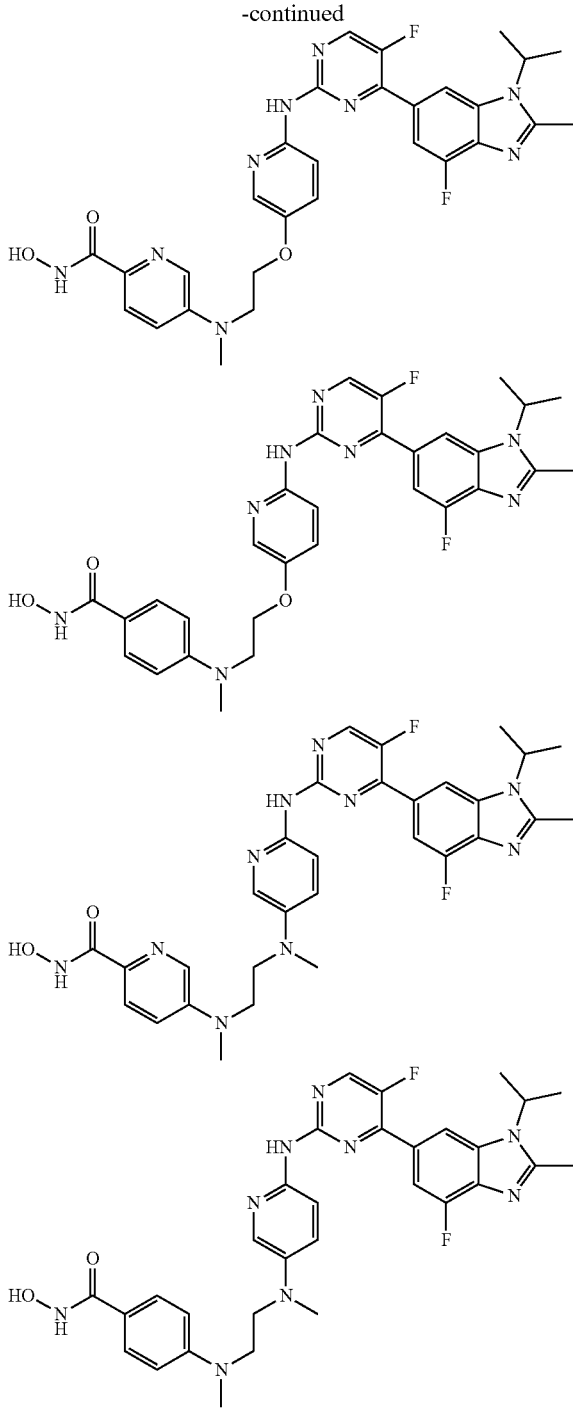

In the second aspect of the present invention, a pharmaceutical composition is provided, which comprising compounds of the first aspect of the invention, and their pharmaceutically acceptable carriers, or excipients.

In the third aspect of the present invention, a compound described in the first aspect of the present invention are provided, wherein in the uses of preparation of a pharmaceutical dependent kinases or histone deacetylases.

In another preferred embodiment, the disease or condition is selected from the groups consisting of breast cancer, lymphoma, leukemia, lung cancer, ovarian cancer, liver cancer, melanoma, colon cancer, rectal cancer, kidney cells cancer, small bowel cancer, esophageal cancer, bladder cancer, prostate cancer, or pharyngeal cancer.

DETAILED DESCRIPTION OF THE INVENTION

Definitions

As use herein, unless clearly indicated otherwise, use of the terms "a", "an" and the like refers to one or more.

As used herein, the word "or" has the meaning of both "or" and "and" and is equivalent to "and/or"—unless otherwise specifically limited to just "or".

As used herein, unless otherwise stated, a chiral carbon atom (or chiral center) of the compound(s) in the invention is optionally R-type, S-type, or a combination thereof.

As used herein, unless otherwise stated, the term "alkyl" by itself or as part of another substituent (which may include the short form of "alk," e.g., alkoxy), refers to a straight (i.e. unbranched), branched chain, or cyclic hydrocarbon radical, or combination thereof, which may be fully saturated, mono- or polyunsaturated and can include di- and multivalent radicals. When an alkyl is preceded by a carbon-number modifier, e.g., $C_{1-10}$, its means the alkyl group contains 1 to 10 carbon atoms. For instance, examples of $C_{1-8}$ alkyl may include a linear or branched alkyl having 1-8 carbon atoms, such as methyl, ethyl, propyl, isopropyl, butyl, isobutyl, sec-butyl, and t-butyl.

As used herein, the term "alkenyl," by itself or as part of another substituent, refers to a straight chain, or branched hydrocarbon chains having at least one carbon-carbon double bond. An alkenyl group with one double bond can be denoted as $-C_nH_{2n-1}$ or $-C_nH_{2n-3}$ with two double bonds. When an alkenyl is preceded by a carbon-number modifier, e.g., $C_{2-8}$, it means the alkenyl group contains 2 to 8 carbon atoms. For instance, examples of $C_{2-8}$ alkenyl may include vinyl, allyl, 1,2-butenyl, 2,3-butenyl, and butadienyl etc.

As used herein, the term "alkynyl," by itself or as part of another substituent, refers to an aliphatic hydrocarbon group with at least one carbon-carbon triple bond. An alkynyl group may be linear or branched or combinations thereof. In some embodiments, it can contain 2 to 12 (e.g., 2 to 8, 2 to 6, or 2 to 4) carbon atoms. When an alkynyl is preceded by a carbon-number modifier, e.g., $C_{2-8}$, it means the alkynyl group contains 2 to 8 carbon atoms. Examples of an alkynyl group (e.g., $C_{2-8}$ alkynyl) may include acetenyl, propynyl, isopropynyl, 1-butynyl, isobutynl, and sec-butynyl etc.

As used herein, the term "cycloalkyl" by itself or as part of another substituent, refers to a saturated or partially saturated carbocyclic mono-, bi-, or tri-cyclic (fused or bridged or spiral) ring system. It can contain 3 to 12 (e.g., 3 to 10, or 5 to 10) carbon atoms. When a cycloalkyl group is preceded by a carbon-number modifier, e.g., $C_{3-10}$, it means the cycloalkyl group contains 3 to 10 carbon atoms. In some embodiments, the term "$C_{3-10}$ cycloalkyl" may refer to a saturated or partially saturated mono- or bicyclic alkyl ring system containing 3 to 10 carbon atoms, such as cyclopropyl, cyclobutyl, cyclopentyl, cyclohexyl, and cycloheptyl. Below are some examples of cycloalkyl group.

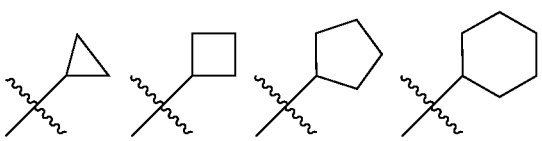

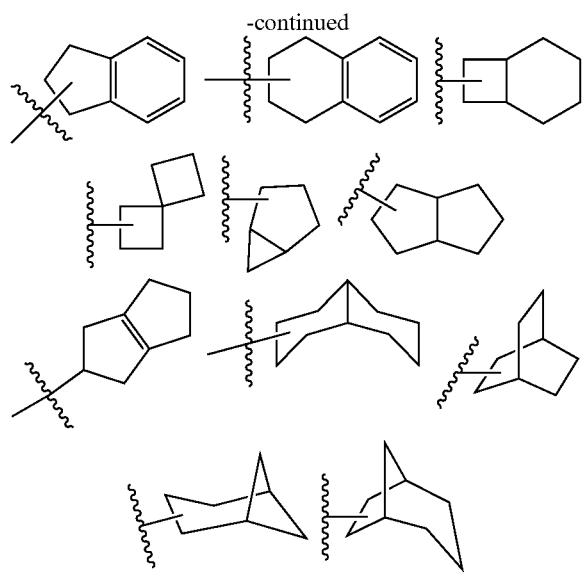

As used herein, the term "alkoxy" or "alkyloxy" refers to an alkyl group linked by an oxygen atom (i.e., —O-alkyl), wherein alkyl is as defined above. Specific examples of "alkoxy" include, but are not limited to, methoxy, ethoxy, n-propoxy, isopropoxy, n-butoxy, iso-butoxy, sec-butoxy, t-butoxy, cyclohexyloxy, and cyclopentyloxy. An alkoxy group can be optionally substituted with one or more appropriate substituents such as halogen, amino, cyano, or hydroxyl. An alkoxy group can be straight or branched. When an alkoxy group is preceded by a carbon-number modifier, e.g., $C_{1-8}$, it means the alkoxy group contains 1 to 8 carbon atoms.

As used herein, the term "halo" or "halogen," by itself or as part of another substituent (e.g., haloalkyl), may refer to and include F, Cl, Br, and/or I.

As used herein, a "carbonyl" group refers to —C(O)— or —C(=O)—.

As used herein, the term "aryl," by itself or as part of another substituent, refers to and includes monocyclic, bicyclic, or polycyclic aromatic hydrocarbon radicals. An aryl group can be substituted or unsubstituted. When an aryl group is preceded by a carbon-number modifier, e.g., $C_{6-12}$, it means the aryl group contains 6 to 12 carbon atoms. Aryl group can be fused with another all-carbon containing cyclic structure (including saturated, partial saturated, or aromatic ring). But the attaching point to the parent structure has to be from aromatic ring system to be able to qualify as aryl. When attaching point to parent structure is on a saturated carbon atom, it can be called as cycloalkyl instead of aryl. Examples of an aryl group include but are not limited to phenyl, biphenylyl, and naphthyl. Below are some examples of aryl group.

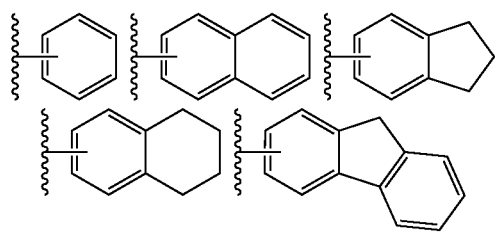

As used herein, the term "heteroaryl" by itself or as part of another substituent, refers to a monocyclic or polycyclic aromatic hydrocarbon radicals, having the number of annular carbon atoms designated (e.g., $C_{4-10}$ means four to ten annular carbon atoms) and containing at least one or more of the same or different heteroatoms each independently being N, O, or S. Each carbon atom may be optionally substituted. A heteroaryl group may be 5- to 15-membered aromatic group containing 1 to 4 heteroatoms each independently being N, O, or S. A heteroaryl group may include a nitrogen containing heteroaryl, an oxygen containing heteroaryl, a sulfur containing heteroaryl.

As used herein, the term "nitrogen containing heteroaryl" refers to an aromatic group having one or more nitrogen atoms in the ring(s). Preferably, it is $C_{4-10}$ nitrogen containing heteroaryl which is an aromatic group having 4 to 10 carbon atoms and one or more nitrogen atoms in the ring. Specific examples include but are not limited to substituted or unsubstituted pyridinyl, pyrimidinyl, and pyrrolyl.

As used herein, the term "oxygen containing heteroaryl" refers to an aromatic group having one or more oxygen atoms in the ring(s). Preferably, it is $C_{4-10}$ nitrogen-containing heteroaryl which is an aromatic group having 4 to 10 carbon atoms and one or more oxygen atoms in the ring(s), such as optionally substituted furyl and benzofuryl.

As used herein, the term "sulfur containing heteroaryl" refers to an aromatic group having one or more sulfur atoms in the ring(s). Preferably, it is $C_{4-10}$ sulfur containing heteroaryl which is an aromatic group having 4 to 10 carbon atoms and one or more sulfur atoms in the ring, such as optionally substituted thienyl.

Below are some examples of heteroaryl group.

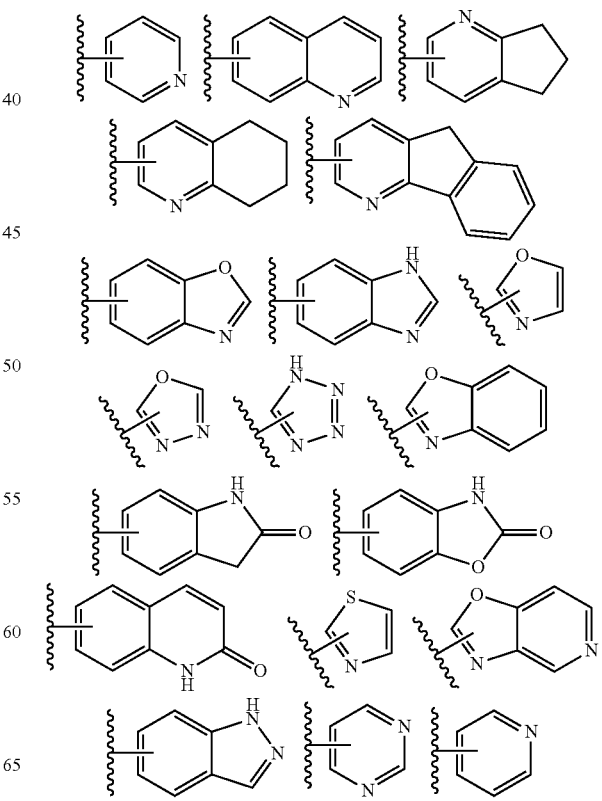

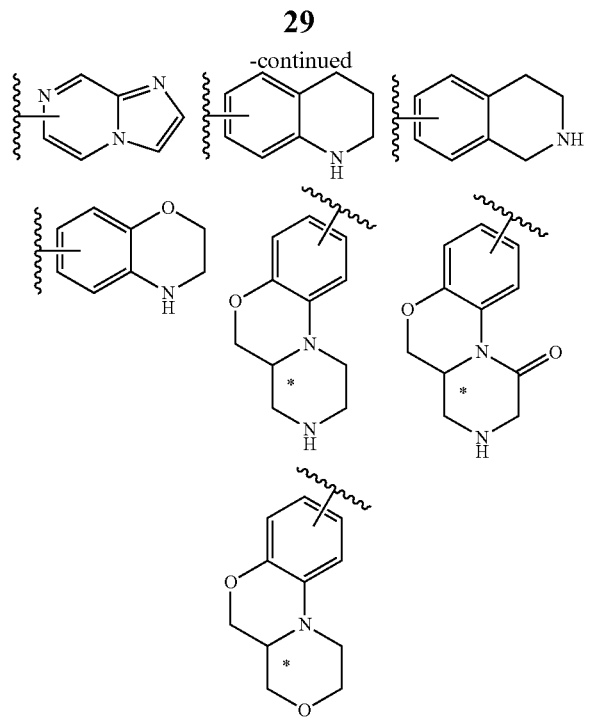

As used herein, the term "heterocyclyl" by itself or as part of another substituent, refers to mono- or polycyclic radicals which may be saturated, partially saturated, or fully unsaturated, having the number of annular carbon atoms designated (e.g., $C_{3-11}$ means three to eleven annular carbon atoms) and containing at least one or more of the same or different heteroatoms each independently being N, S, or O. A heterocyclyl group may be 3- to 15-membered group containing 1 to 4 heteroatoms each independently being N, O, or S. A heteroaryl group may include a nitrogen containing heterocyclyl, oxygen containing heterocyclyl, and sulfur containing heterocyclyl, nitrogen and oxygen containing heterocyclyl, nitrogen and sulfur containing heterocyclyl, sulfur and oxygen containing heterocyclyl, etc. Below are some examples of heterocycle.

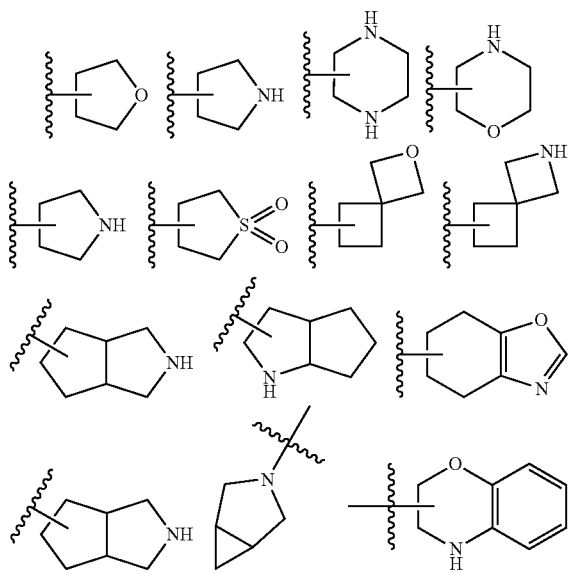

As used herein, the term "optionally" (e.g., as in "optionally substituted with") means that the moiety at issue is either substituted or not substituted, and that the substitution occurs only when it is chemically feasible. For instance, H cannot be substituted with a substituent and a covalent bond or —C(═O)— group cannot be substituted with a substituent.

As used herein, an "oxo" or "oxide" group refers to ═O.

As used herein, the term "pharmaceutically acceptable salt"—unless otherwise specified—refers to salts which are suitable for use in contact with the tissues of a subject (e.g., human) without excessive adverse effect. In some embodiments, pharmaceutically acceptable salts include salts of a compound of the invention having an acidic group (e.g., potassium salts, sodium salts, magnesium salts, calcium salts) or a basic group (e.g., sulfate, hydrochloride, phosphate, nitrate, carbonate).

As used herein, the term "substituted" whether preceded by the term "optionally" or not, refers to the replacement of hydrogen radicals in a given structure with the radical of a specified substituent. Specific substituents are described above in the definitions and below in the description of compounds and examples thereof. Unless otherwise indicated, an optionally substituted group can have a substituent at each substitutable position of the group, and when more than one position in any given structure can be substituted with more than one substituent selected from a specified group, the substituent can be either the same or different in every position. A ring substituent, such as a heterocycloalkyl, can be bound to another ring, such as a cycloalkyl, to form a spiro-bicyclic ring system, e.g., both rings share one common atom. As one of ordinary skill in the art will recognize, combinations of substituents envisioned by this invention are those combinations that result in the formation of stable or chemically feasible compounds. Examples of the substituents include but are not limited to $C_{1-8}$ alkyl, $C_{2-8}$ alkenyl, $C_{2-8}$ alkynyl, $C_{3-10}$ cycloalkyl, $C_{1-8}$ alkyloxy, halogen, hydroxyl, carboxyl (—COOH), $C_{1-8}$ aldehyde, $C_{2-10}$ acyl, $C_{2-10}$ ester, amino, amido, phenyl. For instance, a phenyl may be optionally substituted with 1-3 substituents each independently is halogen, $C_{1-10}$ alkyl, cyano, OH, nitro, $C_{3-10}$ cyclic hydrocarbyl, $C_{1-8}$ alkoxy, or amino.

For convenience and as commonly understood, the term "optionally substituted" only applies to the chemical entities that can be substituted with suitable substituents, not to those that cannot be substituted chemically.

Unless specifically otherwise defined, all the terms used herein have their common meanings as known to a skilled person in the art.

In one preferred embodiment, a compound of Formula (I) is selected from the compounds shown above.

In a preferred embodiment, A, Ⓑ, Ⓒ, W, and V in Formula (I) independently are selected from the corresponding groups or structure fragments included by the specific compounds shown above. p and q independently are selected from the parameters that can constitute the above specific compounds.

It should be understood that compounds of formula (I) may also have various derivatives, for example, any hydrogen atom of which may have derivatives rich in deuterium, or crystal forms and salts formed by compounds of formula (I). The derivatives can be easily obtained by those skilled in the art after reading the contents of the present invention.

General Synthetic Schemes for the Compounds of this Invention

Abbreviation

Boc₂O=di-tert-butyl dicarbonate
Cs₂CO₃=cesium carbonate
DCM=dichloromethane
DIPEA=N,N-diisopropylethylamine
DMAP=4-dimethylaminopyridine
DMF=N,N-dimethylformamide
DMSO=dimethyl sulphoxide
e.e.=enantiomeric access
EtOAc or EA=ethyl acetate
HATU=(1-[bis(dimethylamino)methylene]-1H-1,2,3-triazolo[4,5-b]pyridinium 3-oxide hexafluorophosphate)
MgCl₂=magnesium chloride
NH₄HCO₃=ammonium bicarbonate
Pd(OAc)₂=palladium(II) acetate
Pd₂dba₃=tris(dibenzylideneacetone)dipalladium(O)
PE=petroleum ether
RT=room temperature
TEA=triethylamine
TFA=trifluoroacetic acid Generally, each reaction is usually carried out in an inert solvent at a reaction temperature of −40° C. to reflux (example 100 or 120° C.). The reaction time in each step is usually from 1 to 72 h, preferably from 0.1 to 24 h or 0.2-12 h.

Formula (Ia) is a part of formula (I). Method A describes a general synthetic method for compound (Ia).

Method A:

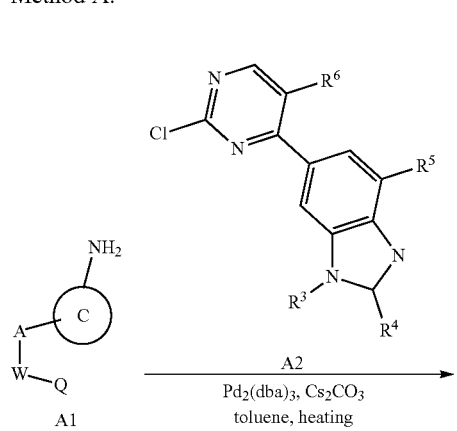

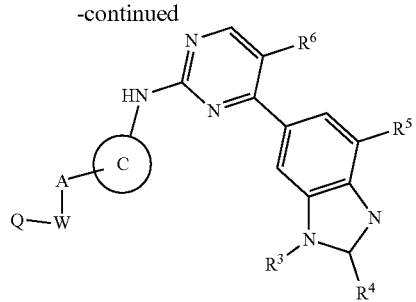

$Q = (CR^1R^2)_p-V-(CR^1R^2)_qC(O)NH(OH)$

The synthesis route of intermediate A1 can be selected according to the specific structure of A1. These synthetic routes can be realized for organic synthesis personnel in the industry.

Formula (Ib) is a part of formula (I). Method B describes a general synthetic method for compound (Ib).

Method B:

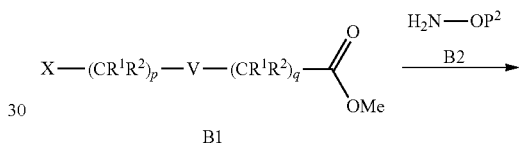

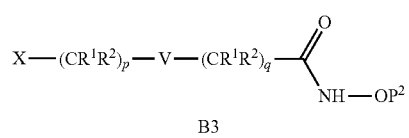

-continued
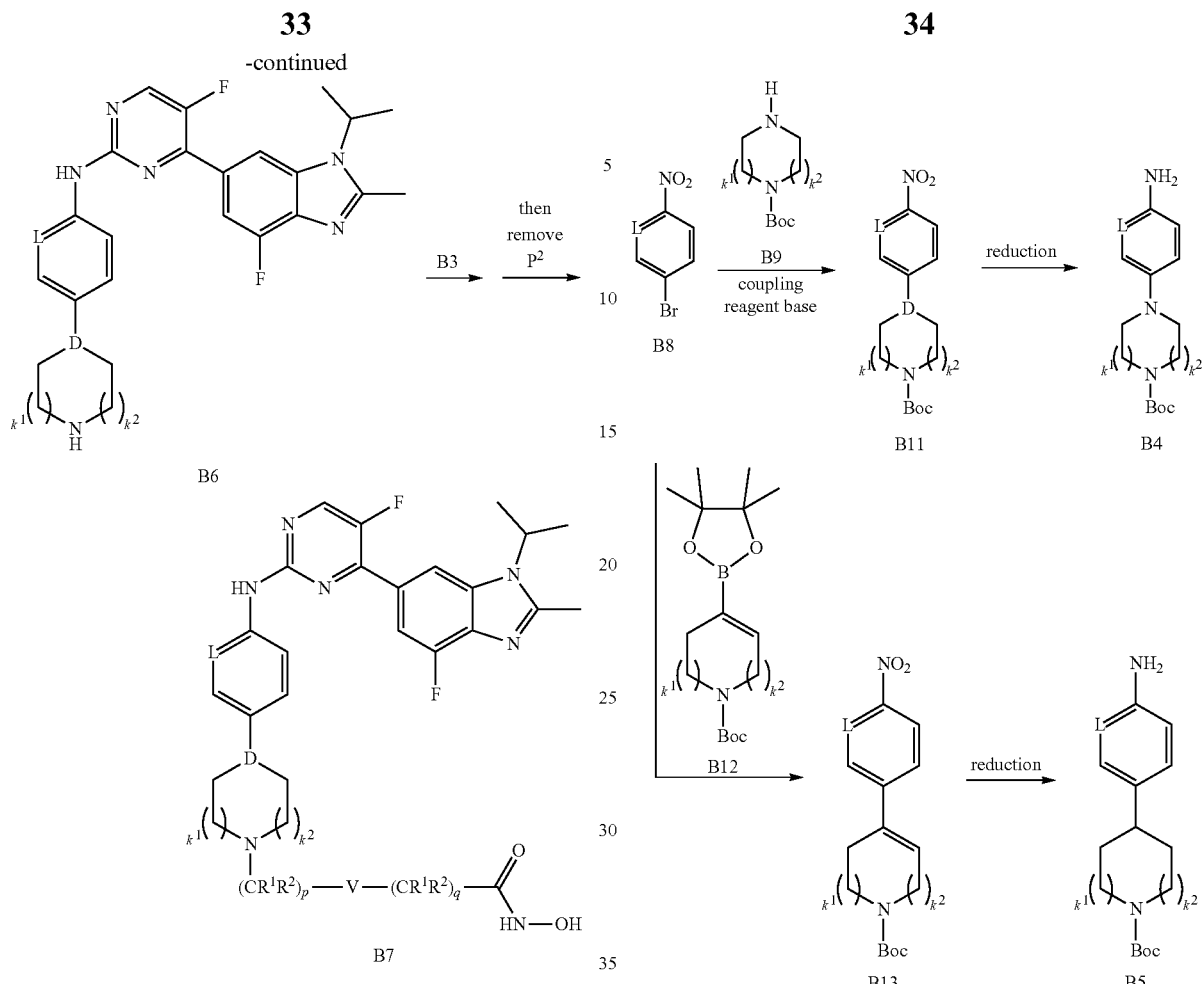
X = Cl, Br, I
P² = protecting group
D = N, CH
L = N, CH
$k^1, k^2$ = 0-3
V, p, q as above
Wherein, intermediates B4 and B5 can be synthesized using the following scheme.
Wherein, intermediate A3 can be synthesized following reference's method: (1) US 20100160340; (2) *Tetrahedron Letters*, 2015, 56(7), 949-951; (3) WO2015130540.
Compound C12 is a part of formula (I). Method C describes a general synthetic scheme for compound C12.
Method C:
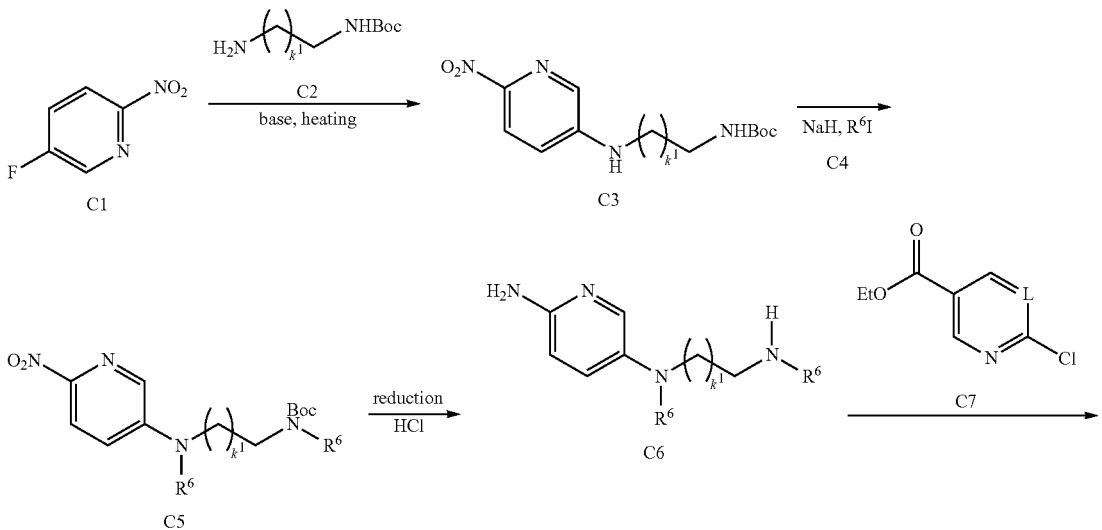

-continued
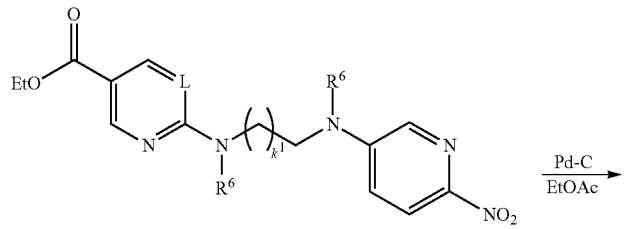
C8
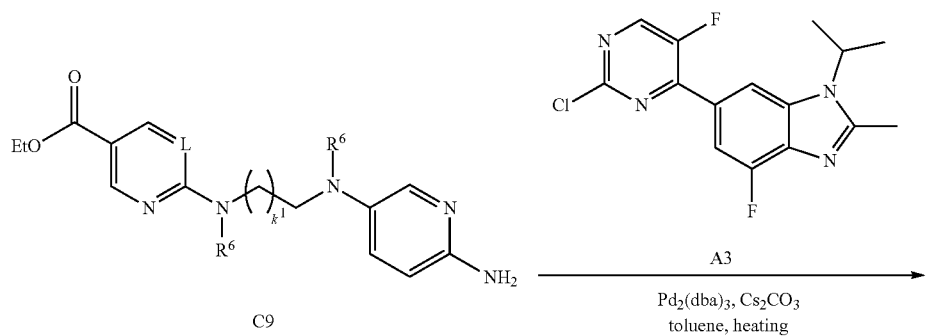
C9
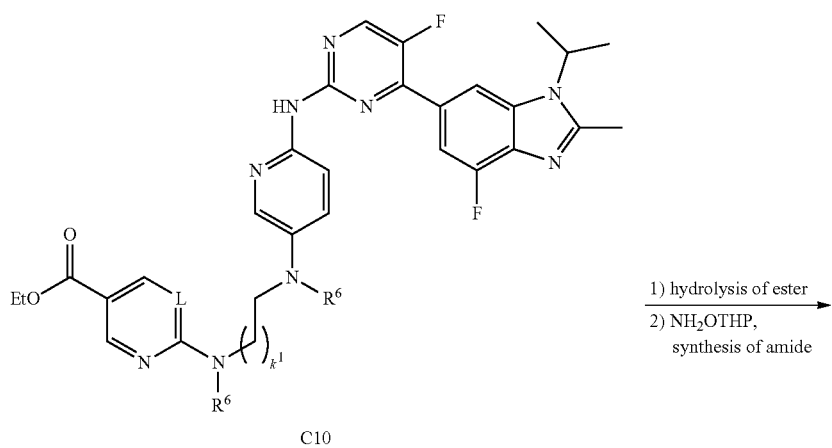
C10
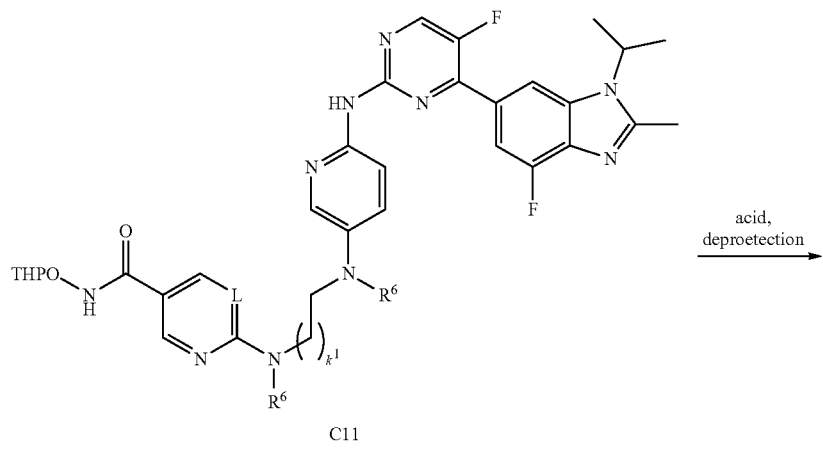
C11

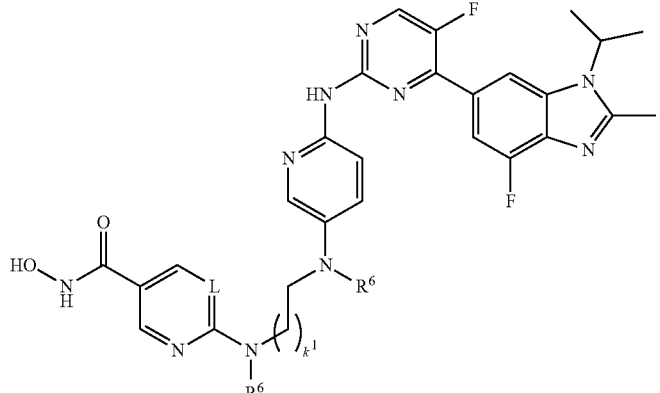
L = N, CH
$k^1$ = 0-5
$R^6$ = $C_{1-4}$ alkyl
Compound D7 is a part of formula (I). Method D describes a general synthetic scheme for compound D7.
Method D:
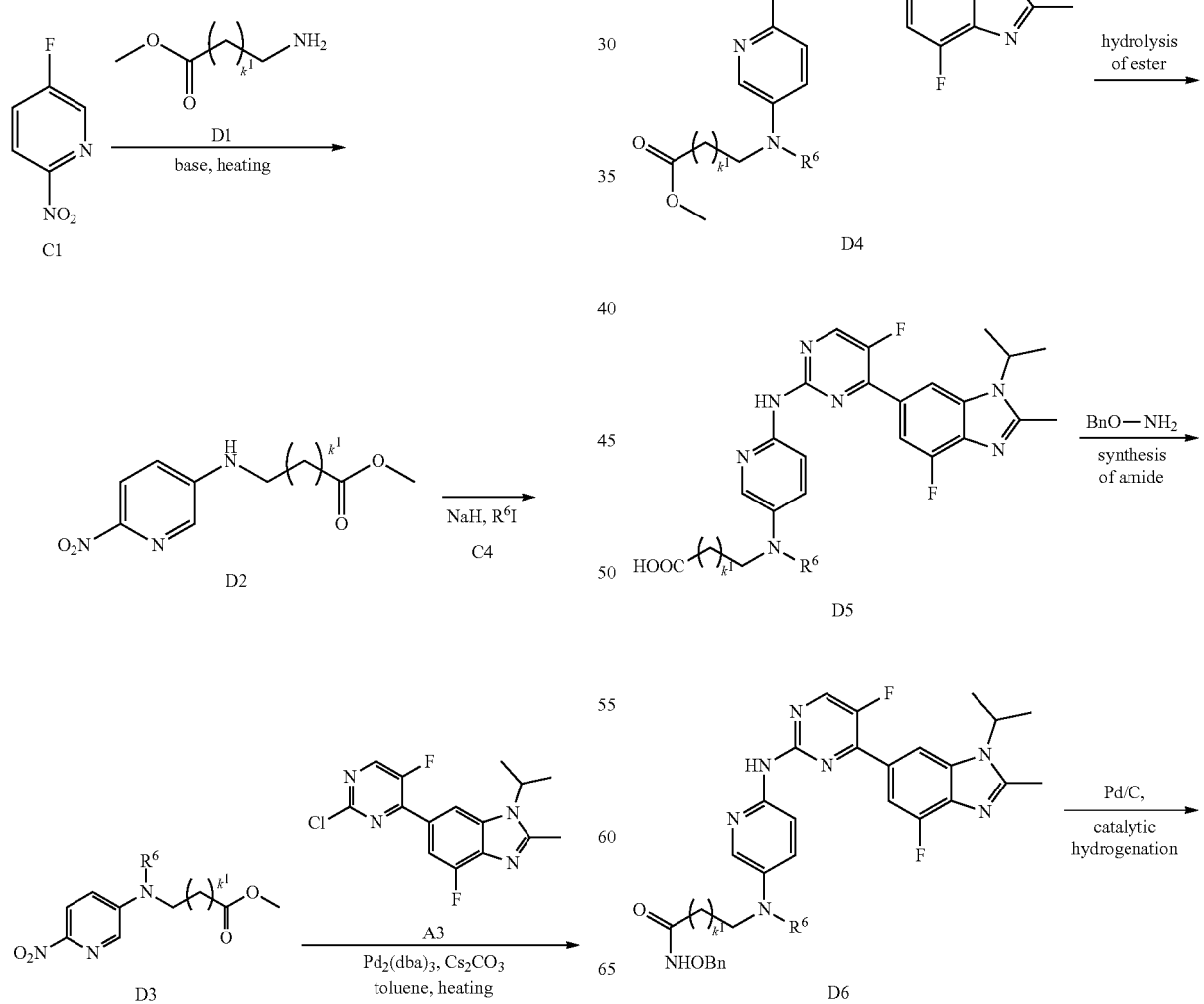

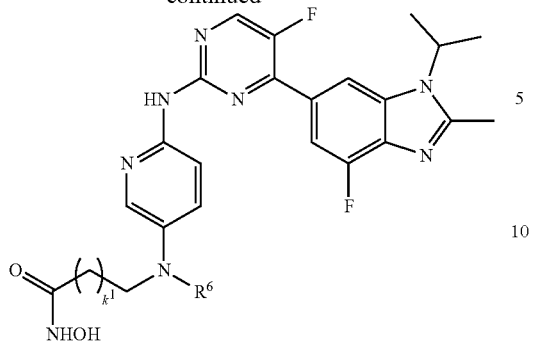
D7
$K^1 = 0 - 10$
$R^6 = C_{1-4}$ alkyl
Compound E9 is a part of formula (I). Method E describes a general synthetic scheme for compound E9.
Method E:
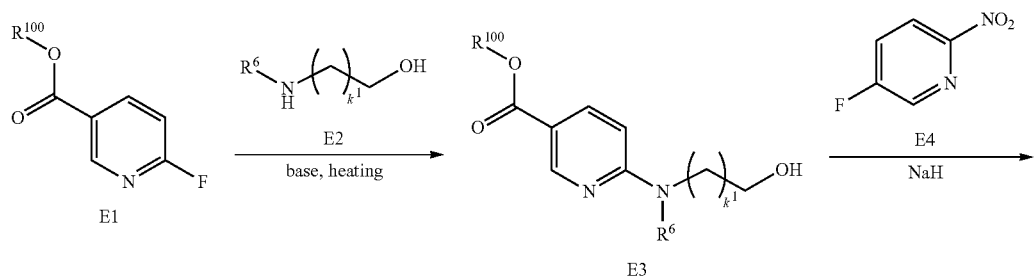
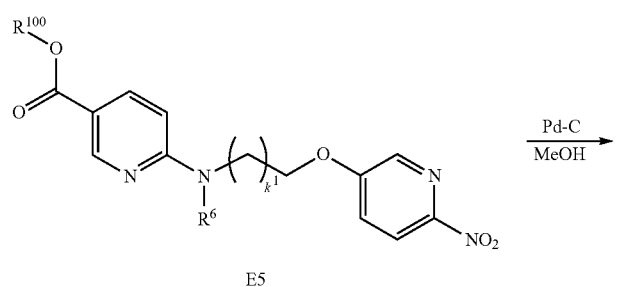
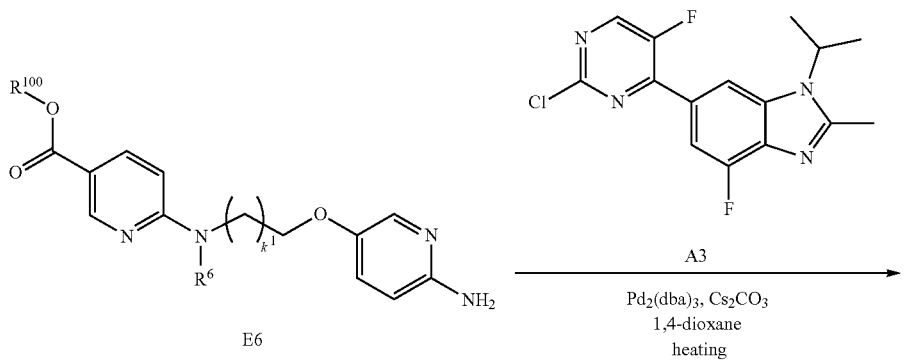

-continued

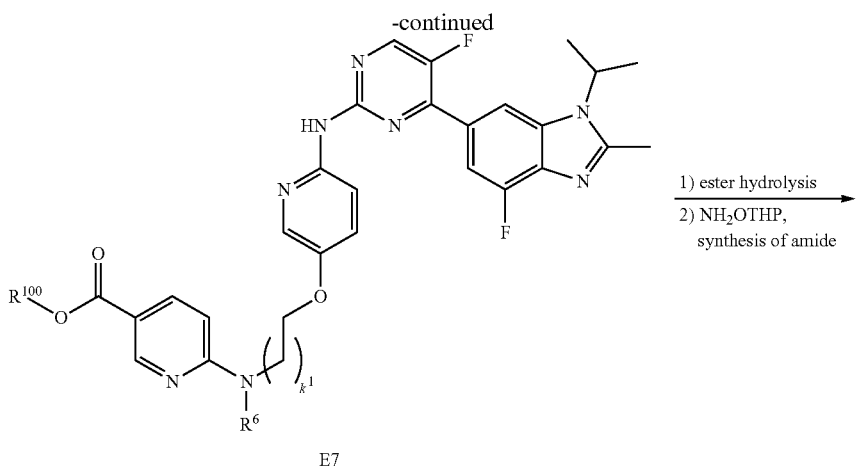

E7

1) ester hydrolysis
2) NH₂OTHP, synthesis of amide

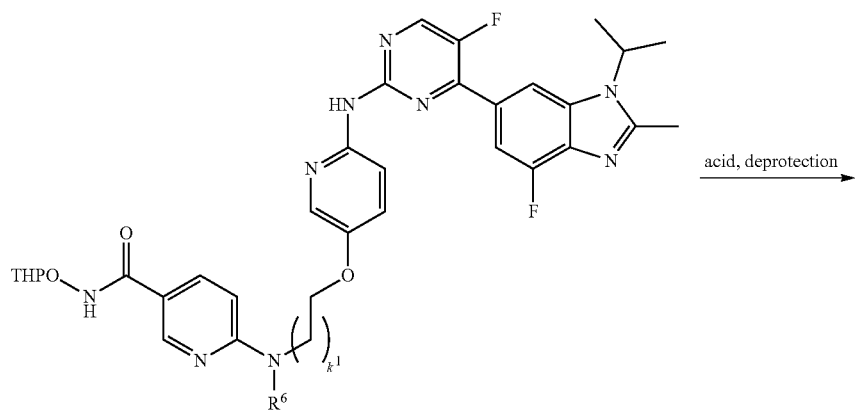

E8 acid, deprotection

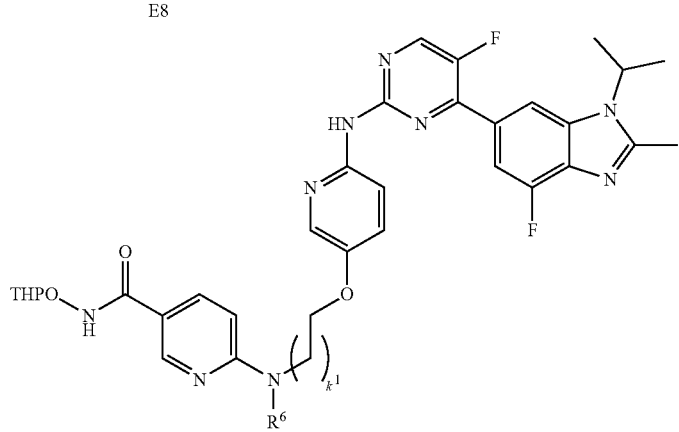

E9

$R^{100}$ = Me, Et
$k^1$ = 0-3
$R^6$ = $C_{1-4}$ alkyl

In addition to the partial synthesis schemes of formula (I) listed above, there are other schemes for synthesizing formula (I), including the replacement of the synthesis sequence of the schemes listed above, and the use of different catalysts and synthesis methods. These synthesis schemes and methods are understandable and achievable for organic synthesis technicians and workers, so it's not going to be elaborated one by one here.

Pharmaceutical Compositions and Administration Thereof

The compounds provided by the present invention are useful as kinase inhibitors, especially as inhibitors of CDK4 and/or CDK6, and/or HDAC inhibitors. Therefore, these compounds possess outstanding therapeutic effect for cancers.

The pharmaceutical composition according to the present invention comprises (i) a safe and effective amount of the compounds of the invention or the pharmaceutical acceptable salts thereof and (ii) a pharmaceutically acceptable excipient or carrier. As used herein, the term "safe and effective amount" means an amount of the compounds which is sufficient to improve the patient's condition and will not induce any serious side effect. Generally, the pharmaceutical composition contains 0.01-100 mg compounds of the invention/dose, preferably 0.10-10 mg compounds of the invention/dose. In some embodiments, "one dose" refers to a capsule or tablet.

A "pharmaceutically acceptable carrier" means one or more compatible solid or liquid fillers or gel materials, which are suitable for human, and usually must have sufficient purity and sufficiently low toxicity. The term "compatibility" as used herein means that the components of the compositions can be blended with the compounds of the invention or with each other, and would not significantly reduce the efficacy of the compounds. Examples of pharmaceutically acceptable carriers include but are not limited to cellulose and the derivatives thereof (such as sodium carboxymethyl cellulose, sodium ethyl cellulose, cellulose acetate, etc.), gelatin, talc, solid lubricants (such as stearic acid and magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween©), wetting agent (such as sodium dodecyl sulfate), coloring agents, flavoring agents, stabilizers, antioxidants, preservatives, and pyrogen-free water.

There is no special limitation to the route of administration for the compounds or pharmaceutical compositions of the invention. The representative administration route includes but is not limited to: oral, parenteral (intravenous, intramuscular or subcutaneous), and topical administration.

Solid dosage forms for oral administration include capsules, tablets, pills, powders and granules. In these solid dosage forms, the active compounds are mixed with at least one conventional inert excipient (or carrier), such as sodium citrate or dicalcium phosphate, or mixed with the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and gum arabic; (c) humectant, such as, glycerol; (d) disintegrating agents such as agar, calcium carbonate, potato starch or tapioca starch, alginic acid, certain complex silicates, and sodium carbonate; (e) dissolution-retarding agents, such as paraffin; (f) absorption accelerators, for example, quaternary ammonium compounds; (g) wetting agents, such as cetyl alcohol and single glyceryl stearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffer.

The solid dosage forms such as tablets, sugar pills, capsules, pills and granules can be prepared by using coating and shell material, such as enteric coatings and other materials known in the art. They can contain opaque agent, and the release of the active compounds or compounds in such compositions can be delayed for releasing in certain portion of the digestive tract. Instance of the embedding components can be polymers and waxes. If necessary, the active compounds and one or more above excipients can be prepared into microcapsules.

Liquid dosage forms for oral administration include pharmaceutically acceptable emulsions, solutions, suspensions, syrups or tinctures. In addition to the active compounds, the liquid dosage forms may contain conventional inert diluent known in the art, such as water or other solvent, solubilizer and emulsifier, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the mixtures thereof and so on.

Besides the inert diluents, the composition may also contain additives such as wetting agents, emulsifiers, and suspending agent, sweetener, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the mixtures thereof and so on.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and the suitable mixtures thereof.

The dosage forms of compounds of the invention for topical administration include ointments, powders, patches, aerosol, and inhalants. The active ingredients are mixed with physiologically acceptable carriers and any preservatives, buffers, or propellant if necessary, under sterile conditions.

The compounds of the invention can be administered alone, or in combination with other pharmaceutically acceptable compounds.

When the pharmaceutical compositions are used, a safe and effective amount of compounds of the present invention is administered or delivered to mammals in need thereof (such as human), wherein the dosage of administration is a pharmaceutically effective amount. For a person weighted about 60 kg, the daily dose is usually 1 to 2000 mg, preferably 20 to 500 mg. Of course, the particular dose should also depend on other factors, such as the route of administration, patient healthy status, etc., which are well within the skill of a skilled physician.

The compounds and pharmaceutical composition of the invention can be used for treating cancer. As used herein, the term "cancer" is meant to include all types of cancerous growths or oncogenic processes, metastatic tissues or malignantly transformed cells, tissues, or organs, irrespective of histopathologic type or stage of invasiveness. Examples of cancerous disorders include, but are not limited to, solid tumors, soft tissue tumors, and metastatic lesions. Examples of solid tumors include malignancies, e.g., sarcomas, adenocarcinomas, and carcinomas, of the various organ systems, such as those affecting prostate, lung, breast, lymphoid, gastrointestinal (e.g., colon), and genitourinary tract (e.g., renal, urothelial cells), pharynx. Adenocarcinomas include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions of the invention. The subject method can be useful in treating malignancies of the various organ systems, such as those affecting lung, breast, lymphoid, gastrointestinal (e.g., colon), bladder, genitourinary tract (e.g., prostate), pharynx, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The examples of cancer include but are not limited to breast cancer, lymph cancer, lung cancer, ovarian cancer, liver cancer melanoma, colon cancers, rectal cancer, renal-cell carcinoma, cancer of the small intestine and cancer of the esophagus, bladder cancer, prostate cancer, or pharynx cancer, etc.

The main advantages of the present invention include at least the following:

(1) The invention provides novel heterocyclic compounds useful as kinase inhibitors and histone deacetylase inhibitors. The main feature of the invention is that a single small molecule can simultaneously inhibit multiple different signal pathways, such as cell dependent kinase and histone deacetylase.

(2) The invention reveals that these novel heterocyclic compounds of Formula (I) possess outstanding effect for inhibiting activity of CDK4, CDK6, and HDACs.

The present invention will be further illustrated below with reference to the specific examples. It should be understood that these examples are only to illustrate the invention but not to limit the scope of the invention. Unless indicated otherwise, parts and percentage are calculated by weight.

Example 1. Preparation of 7-(4-((6-((5-fluoro-4-(4-fluoro-1-isopropyl-2-methyl-1H-benzo[d]imidazol-6-yl)pyrimidin-2-yl)amino)pyridin-3-yl)methyl)piperazin-1-yl)-N-hydroxyheptanamide (Compound 1)

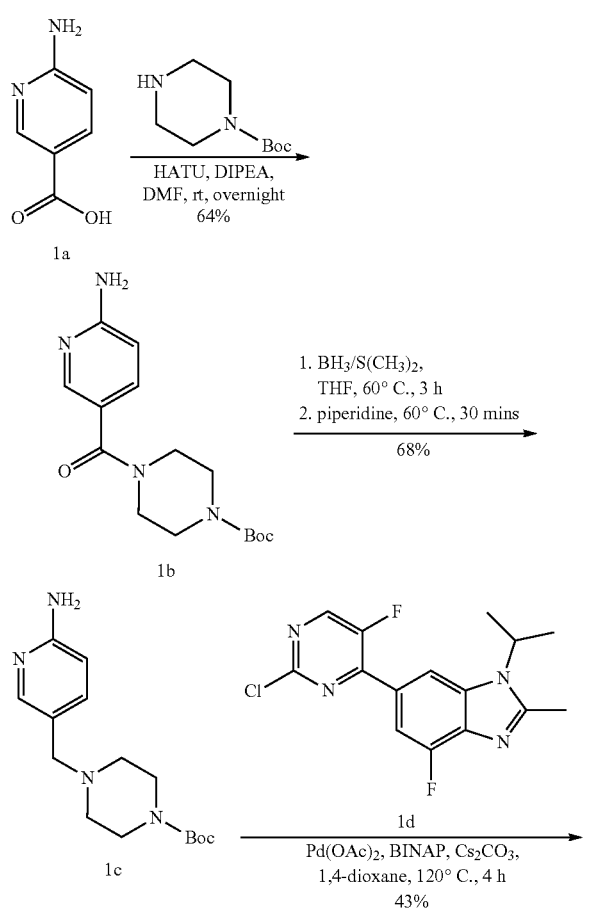

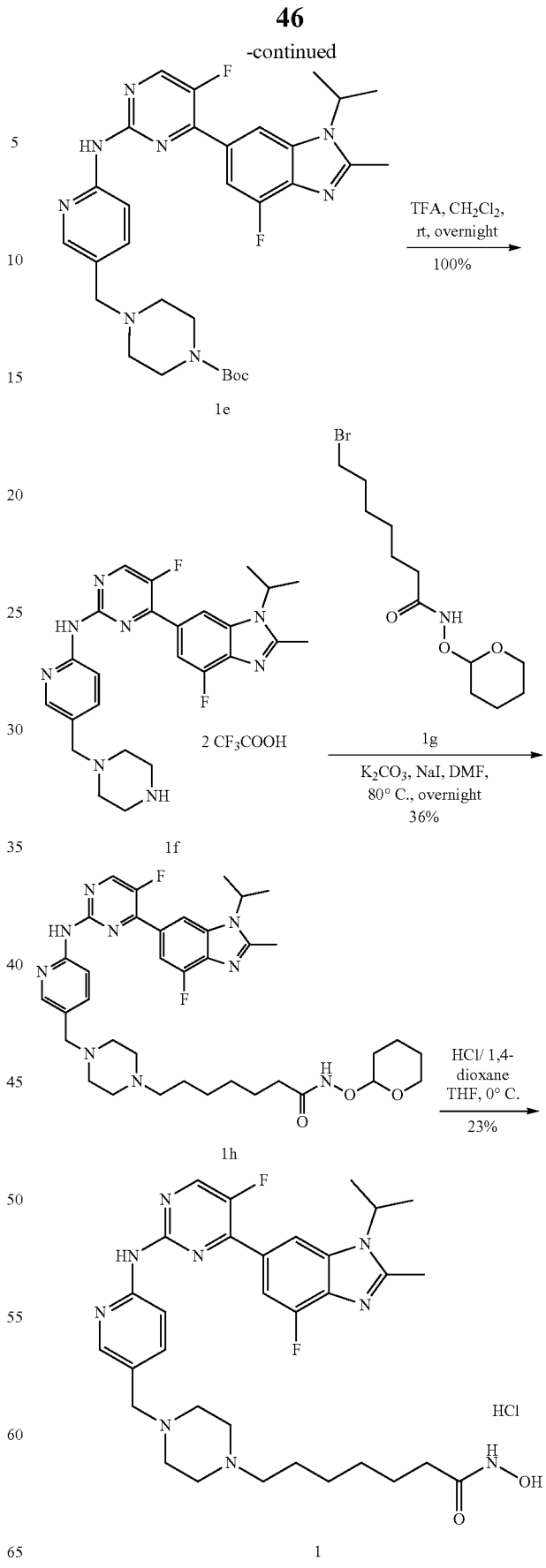

Compound 1a (700 mg, 5.07 mmol), N-Boc-piperazine (1.04 g, 5.57 mmol), DIPEA (1.31 g, 10.2 mmol), and HATU (2.889 g, 7.605 mmol) were dissolved in DMF (10 mL), and the reaction mixture was stirred at room temperature overnight. It was poured into water, extracted with ethyl acetate (40 mL×3). The combined organic layers were washed with brine, dried over anhydrous magnesium sulfate, filtered and concentrated under reduced pressure at 40° C. The residue was purified by SiO$_2$ column chromatography (dichloromethane:methanol=20:1) to afford compound 1b (1.0 g, yield: 64%) as a white solid. MS m/z 307.3 [M+H]$^+$.

Compound 1b (400 mg, 1.31 mmol) was dissolved in THF (10 mL) followed by the addition of a solution of borane in dimethyl sulfide (1.0 M, 4.0 mL). The reaction mixture was stirred at 60° C. for 3 hours. Piperidine (1 mL) was added to the reaction mixture and stirred at 60° C. for 30 minutes. After cooling to room temperature, it was poured into water, extracted with ethyl acetate (15 mL×3). The combined organic layers were washed with brine, dried over anhydrous magnesium sulfate, filtered, and concentrated under reduced pressure. The residue was purified by SiO$_2$ column chromatography (dichloromethane:methanol=20:1) to afford compound 1c (260 mg, yield: 68%) as a white solid. MS m/z 293.0 [M+H]$^+$.

Compound 1c (120 mg, 0.41 mmol), 1d (90 mg, 0.29 mmol, prepared according to patent: US20100160340), Pd(OAc)$_2$ (9.0 mg, 0.04 mmol), BINAP (25 mg, 0.04 mmol), Cs$_2$CO$_3$ (195 mg, 0.60 mmol), and 1, 4-dioxane (5.0 mL) placed in a reaction tube was stirred at 120° C. for 4 hours. It was poured into water and extracted with ethyl acetate (10 mL×3). The combined organic layers were washed with brine, dried over anhydrous magnesium sulfate, filtered, and concentrated under reduced pressure at 35° C. The residue was purified by preparative TLC (dichloromethane:methanol=20:1) to afford compound 1e (70 mg, yield 43%) as a yellow solid. MS m/z 579.4 [M+H]$^+$.

Compound 1e (70 mg, 0.12 mmol) was dissolved in dichloromethane (5 mL) followed by the addition of CF$_3$CO$_2$H (1.0 mL). The reaction mixture was stirred at room temperature overnight. The reaction mixture was concentrated under reduced pressure at 40° C. to afford compound 1f (85 mg, yield: 100%) as a yellow solid. MS m/z 479.0 [M+H]$^+$.

Compounds 1g (110 mg, 0.36 mmol) and 1f (85 mg, 0.12 mmol) were dissolved in DMF (3 mL) followed by the addition of K$_2$CO$_3$ (42 mg, 0.30 mmol) and NaI (5 mg, 0.03 mmol), and the reaction mixture was stirred at 80° C. overnight. After cooling to room temperature, it was poured into water, extracted with ethyl acetate (10 mL×3). The combined organic layers were washed with brine, dried over anhydrous magnesium sulfate, and concentrated under reduced pressure. The residue was purified by preparative TLC (dichloromethane:methanol=5:1) to afford compound 1h (30 mg, yield: 36%) as a yellow solid. MS m/z 706.4 [M+H]$^+$.

Compound 1h (30 mg, 0.042 mmol) was dissolved in THF (2 mL) followed by the addition of HCl in dioxane (4 M, 0.5 mL) under ice bath. The reaction mixture was stirred at room temperature for 3 hours. It was concentrated under reduced pressure at 30° C. and dried to afford a yellow solid, which was purified by prep-HPLC to afford compound 1 hydrochloride salt (6.05 mg, yield: 23%) as a yellow solid. $^1$H NMR (400 MHz, DMSO-d$_6$): δ 10.49 (d, J=14.4 Hz, 1H), 10.34 (s, 1H), 8.75 (d, J=3.6 Hz, 1H), 8.29 (d, J=3.2 Hz, 2H), 8.20 (d, J=8.8 Hz, 1H), 7.83-7.81 (m, 1H), 7.72 (d, J=12.0 Hz, 1H), 4.90-4.82 (m, 1H), 5.53-4.12 (m, 6H), 3.78 (brs, 2H), 3.48 (brs, 2H), 3.20-2.85 (m, 4H), 2.66 (s, 3H), 1.94 (t, J=7.2 Hz, 2H), 1.64 (s, 3H), 1.63 (s, 3H), 1.62-1.50 (m, 2H), 1.49-1.39 (m, 2H), 1.28-1.20 (m, 4H). MS m/z 622.4 [M+H]$^+$.

Example 2. Preparation of 2-((2-((6-((5-fluoro-4-(4-fluoro-1-isopropyl-2-methyl-1H-benzo[d]imidazol-6-yl)pyrimidin-2-yl)amino)pyridin-3-yl)(methyl)amino)ethyl)(methyl) amino)-N-hydroxypyrimidine-5-carboxamide (Compound 2)

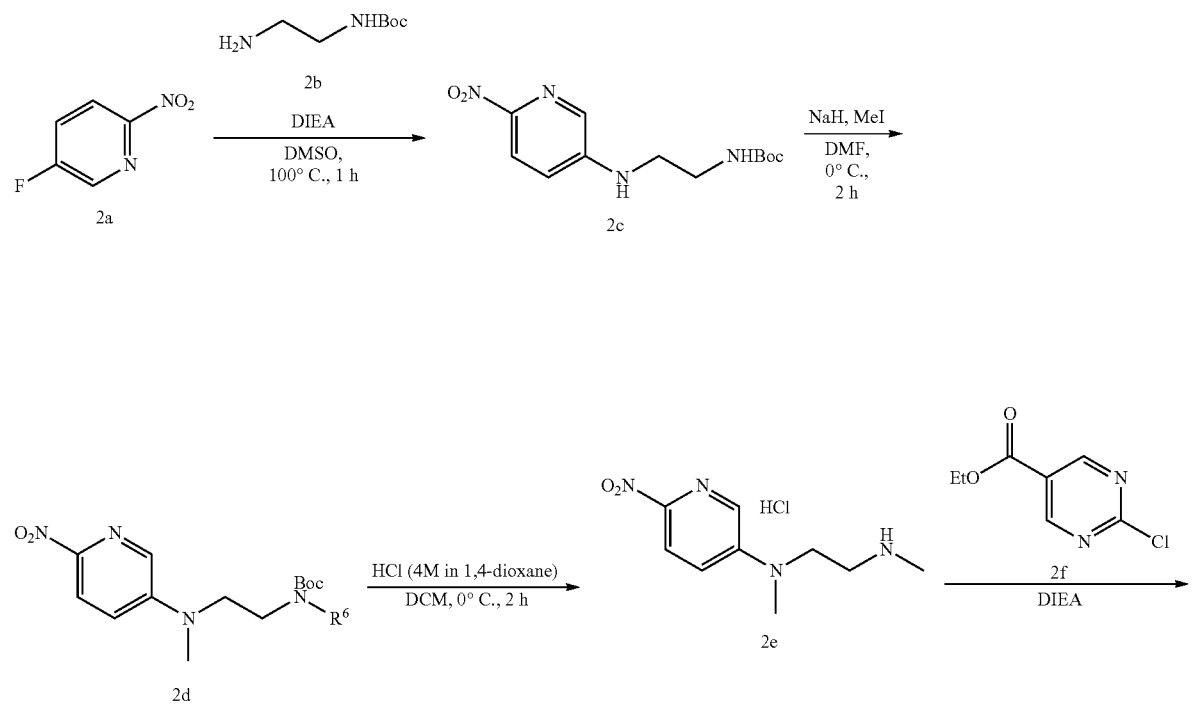

-continued
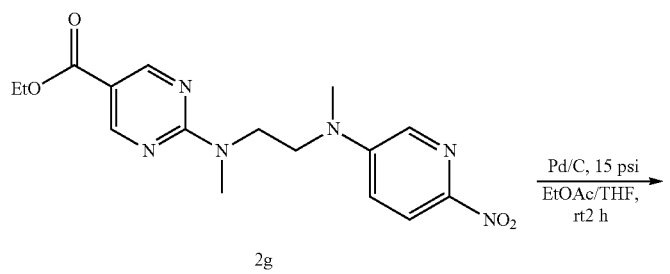
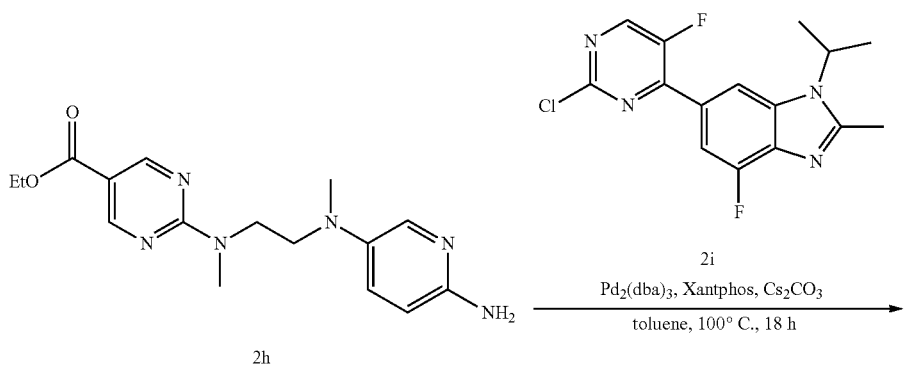
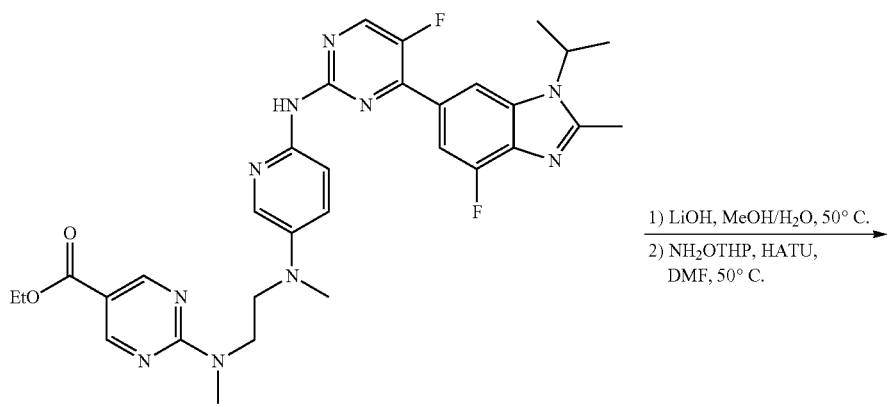
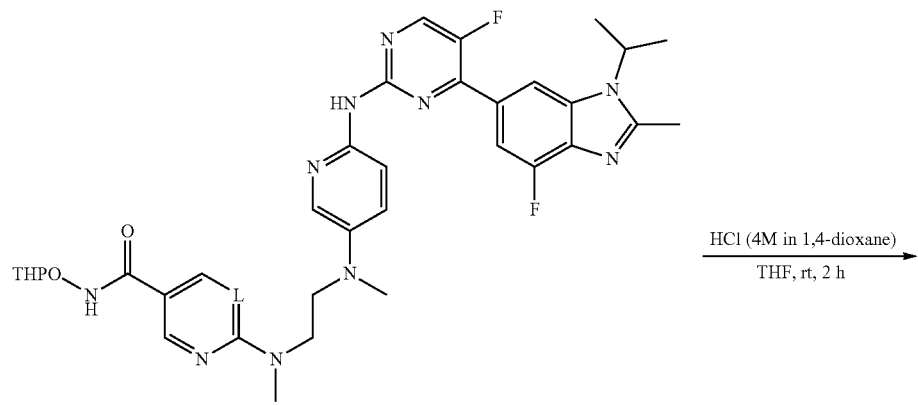

-continued

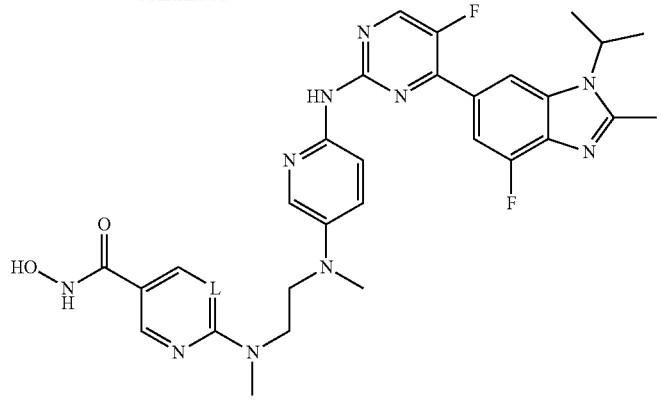

2

Compound 2a (0.2 g, 1.41 mmol), 2b (0.27 g, 1.69 mmol), and DIPEA (0.36 g, 2.82 mmol) were added to DMSO (5 mL, and the reaction mixture was stirred at 100° C. for 1 hour. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure. The residue product was purified by $SiO_2$ column chromatography (dichloromethane:methanol=20:1) to afford compound 2c (0.3 g, yield: 76%) as a yellow oil.

Compound 2c (0.3 g, 1.06 mmol) was added to DMF (10 mL). The reaction mixture was cooled to 0° C. NaH (0.1 g, 2.66 mmol) was added slowly to the reaction mixture, and stirred for 1 hour. $CH_3I$ (0.45 g, 3.19 mmol) was added and the reaction mixture was stirred until the reaction was completed. After cooling to room temperature, it was poured into water, and extracted with ethyl acetate (three times). The combined organic layers were washed with brine, dried over anhydrous sodium sulfate, and concentrated under reduced pressure to afford compound 2d (0.28 g, yield: 85%) as a yellow solid (The compound was used in next step without further purification).

Compound 2d (0.28 g, 0.09 mmol) was added to dichloromethane (5 mL) followed by the addition of a solution of HCl in 1, 4-dioxane (4 M, 1 mL) at 0° C. The reaction mixture was stirred at room temperature for 2 hours. The reaction was monitored by TLC for completion. It was concentrated to afford compound 2e (180 mg, yield: 95%) as a yellow solid (The compound was used in next step without further purification).

Compound 2e (280 mg, 1.14 mmol), 2f (254 mg, 1.36 mmol), and DIPEA (293 mg, 2.27 mmol) were added to DMSO (5 mL). The reaction mixture was heated to 100° C. and stirred for 1 hour. The reaction was monitored by TLC for completion. After cooling to room temperature, it was poured into water, and extracted with ethyl acetate (three times). The combined organic layers were washed with brine and dried over anhydrous sodium sulfate, and concentrated under reduced pressure. The residue was stirred in a mixture of dichloromethane and petroleum ether (1:5) and filtered to afford compound 2g (250 mg, yield: 61%) as a yellow solid.

Compound 2g (250 mg, 2.31 mmol) was dissolved in a mixture of EtOA and THF (10 mL, 1:1) followed by the addition of Pd/C (25 mg). The reaction mixture was stirred under $H_2$ atmosphere for 2 hours. The reaction was monitored by TLC for completion. It was filtered through celite and the filtrate was concentrated. The residue was purified by $SiO_2$ column chromatography (dichloromethane:methanol=20:1) to afford compound 2h (180 mg, yield: 78%) as an off-white solid.

Compound 2h (180 mg, 0.54 mmol), 2i (211 mg, 0.65 mmol, intermediate 2i same as above intermediate 1d, prepared according to patent: US20100160340), $Pd_2(dba)_3$ (100 mg, 0.11 mmol), xantphos (470 mg, 0.82 mmol), and $Cs_2CO_3$ (532 mg, 1.63 mmol) were dissolved in anhydrous toluene (10 mL). The reaction mixture was heated to 120° C. under $N_2$ atmosphere for 18 hours. After cooling to room temperature, it was poured into water, and extracted with ethyl acetate (three times). The combined organic layers were washed with brine, dried over anhydrous sodium sulfate, and concentrated under reduced pressure. The residue was purified by $SiO_2$ column chromatography (dichloromethane:methanol=20:1) to afford compound 2j (0.18 g, yield: 53%) as a yellow solid.

Compound 2j (180 mg, 0.29 mmol) and lithium hydroxide monohydrate (122 mg, 2.92 mmol) were dissolved in methanol and water (14 mL/6 mL), and the reaction mixture was heated to 60° C. and stirred overnight. The reaction was monitored by TLC for completion. The reaction mixture was concentrated to remove methanol, acidified with aqueous HCl (2 M) to pH=5, and extracted with ethyl acetate (three times). The combined organic layers were washed with brine, dried over anhydrous sodium sulfate, filtered, and concentrated to afford compound 2k (140 mg, yield: 82%) as a light yellow solid (The compound was used in next step without further purification).

Compound 2k (140 mg, 0.24 mmol), N,N-diisopropylethylamine (62 mg, 0.48 mmol), HATU (136 mg, 0.36 mmol), and o-(tetrahydro-2H-pyran-2-yl)hydroxylamine (31 mg, 0.26 mmol) were added to DMF (15 mL) and the reaction mixture was stirred at 50° C. for 2 hours. The reaction was monitored by TLC for completion. It was poured into water, and the precipitate was filtered. The solid was purified by $SiO_2$ column chromatography (dichloromethane/methanol=25:1~15:1) to afford compound 2l (100 mg, yield: 61%) as a yellow solid. Compound 2l (25 mg, 0.036 mmol) was added to THF (1 mL) following the addition of HCl in 1, 4-dioxane (4 M, 10 drops) and deionized water (10 drops). The reaction mixture was stirred at room temperature for 5 hours. The reaction was monitored by TLC for completion. $Et_2O$ was added and the precipitate was filtered. The solid was washed with $Et_2O$ and acetonitrile, and dried to afford compound 2 hydrochloride salt (15 mg, yield: 68%) as a yellow solid. MS m/z 604.0 [M+H]$^+$.
Example 3. Preparation of 7-((6-((5-fluoro-4-(4-fluoro-1-isopropyl-2-methyl-1H-benzo[d]imidazol-6-yl)pyrimidin-2-yl)amino)pyridin-3-yl)(methyl)amino)-N-hydroxyheptanamide (Compound 3)
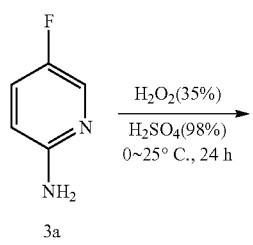
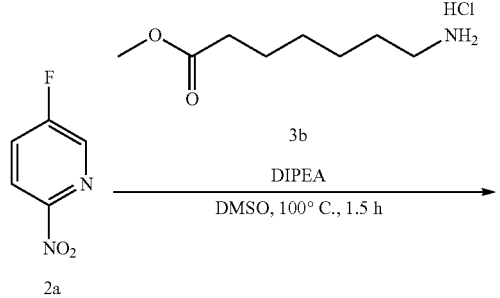
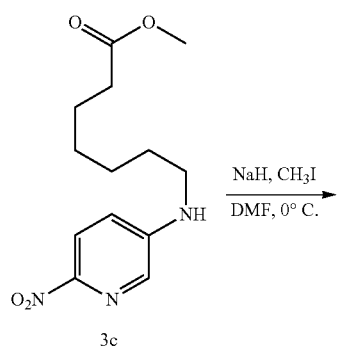
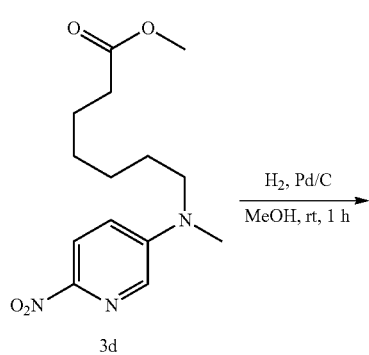
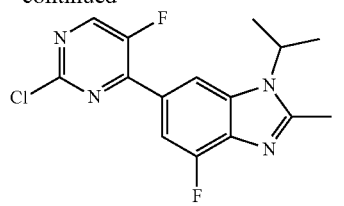
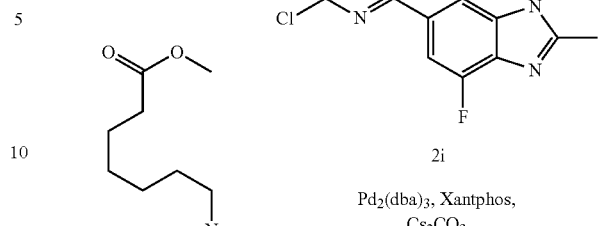
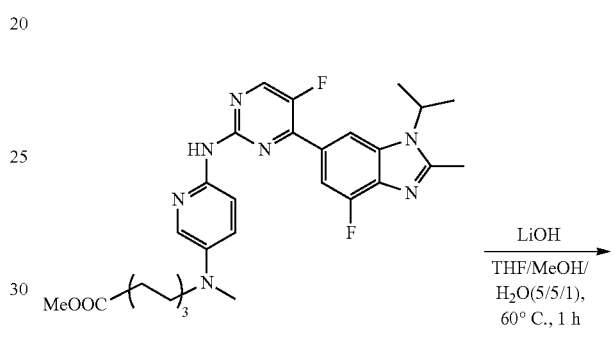
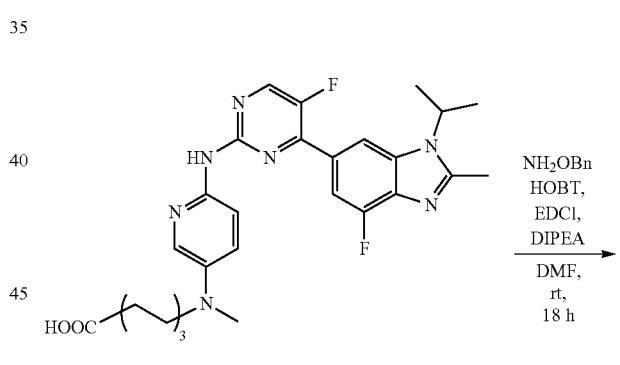
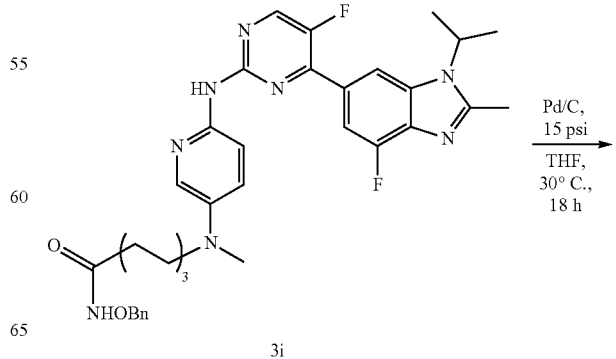

-continued

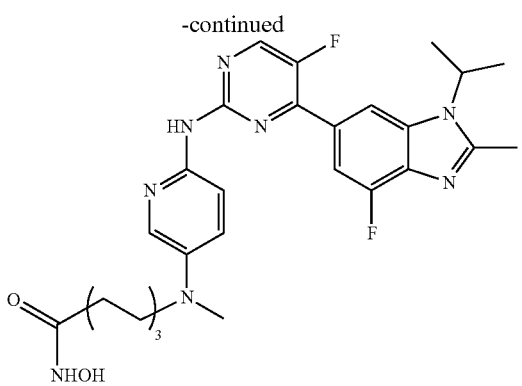

3

H₂O₂ (35%, 2.5 mL) was added to concentrated H₂SO₄ (6 mL) at 0° C. followed by the addition of a cooled solution of compound (3a (1.0 g, 8.90 mmol) in concentrated H₂SO₄ (6 mL). The reaction mixture was stirred at room temperature for 24 hour. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure. The residue was purified by SiO₂ column chromatography (petroleum ether/EtOAc=20:1) to afford compound 2a (0.6 g, yield: 47%) as a yellow solid.

Compound 2a (100 mg, 0.70 mmol), 3b (165 mg, 0.84 mmol), and DIPEA (182 mg, 1.40 mmol) were added to DMSO (3 mL). The reaction mixture was heated to 100° C. and stirred for 1.5 hours. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure to afford compound 3c (0.15 g, yield: 95%) as a yellow solid (The compound was used in next step without further purification).

Compound 3c (150 mg, 0.53 mmol) was added to DMF (3 mL) and the reaction mixture was cooled to 0° C. 60% NaH (32 mg, 0.80 mmol) was added to the reaction mixture and stirred for 1 hour. CH₃I (113 mg, 0.80 mmol) was added. The reaction was monitored by TLC for completion. It was poured into water, and extracted with ethyl acetate (three times). The combined organic layers were washed with brine, dried over anhydrous sodium sulfate, and concentrated under reduced pressure. The residue was purified by SiO₂ column chromatography (dichloromethane:methanol=20:1) to afford a solid, which was stirred in a mixture of dichloromethane and petroleum (1:5) and filtered to afford compound 3d (0.14 g, yield: 89%) as a yellow solid.

Pd/C (14 mg) was added to a solution of compound 3d (0.14 g, 0.47 mmol) in methanol (5 mL), and reaction mixture was stirred under H₂ atmosphere at room temperature for 1 hour. The reaction was monitored by TLC for completion. It was filtered through celite, and the filtrate was concentrated under reduced pressure. The residue was purified by SiO₂ column chromatography (dichloromethane:methanol=20:1) to afford compound 3e (95 mg, yield 75%) as a gray solid.

Compound 3e (90 mg, 0.34 mmol), 2i (131 mg, 0.41 mmol, Pd₂(dba)₃ (62 mg, 0.068 mmol), xantphos (300 mg, 0.51 mmol), and Cs₂CO₃ (332 mg, 1.02 mmol) were dissolved in anhydrous toluene (10 mL). The reaction mixture was heated to 120° C. under N₂ atmosphere and stirred for 1 hour. After cooling to room temperature, it was poured into water, and extracted with ethyl acetate (three times). The combined organic layers were washed with brine, dried over anhydrous sodium sulfate, and concentrated under reduced pressure. The residue was purified by SiO₂ column chromatography (dichloromethane:methanol=20:1) to afford compound 3f (100 mg, yield: 53%) as a yellow solid.

Compound 3f (100 mg, 0.18 mmol) and lithium hydroxide monohydrate (76 mg, 1.81 mmol) were dissolved in a mixture of THE (5 mL), MeOH (5 mL), and water (1 mL). The reaction mixture was stirred at 60° C. for 18 hours. The reaction was monitored by TLC for completion. It was concentrated to remove methanol, acidified with aqueous HCl (2 M) to pH=5, and extracted with ethyl acetate (three times). The combined organic layers were concentrated under reduced pressure to afford compound 3g (86 mg, yield: 88%) as a yellow solid (The compound was used in next step without further purification).

Compound 3g (86 mg, 0.16 mmol), N,N-diisopropylethylamine (62 mg, 0.48 mmol), HOBT (32 mg, 0.24 mmol), EDCI (46 mg, 0.24 mmol), and o-benzylhydroxylamine (24 mg, 0.19 mmol) were added to DMF (5 mL). The reaction mixture was stirred at 50° C. for 2 hours. The reaction was monitored by TLC for completion. It was poured into water, and the solid was collected via filtration. The solid was purified by SiO₂ column chromatography (dichloromethane:methanol=25:1~15:1) to afford compound 3h (78 mg, yield: 76%) as a yellow solid.

Pd/C (5 mg) was added to a solution of compound 3h (20 mg, 0.03 mmol) in methanol (2 mL), and the reaction mixture was stirred at 30° C. under H₂ atmosphere for 18 hours. The reaction was monitored by TLC for completion. It was filtered through celite. Et₂O was added to the filtrate and the precipitate was collected via filtration. The solid was washed with a mixture of acetonitrile and Et₂O (1:1) to afford compound 3 (10 mg, yield 58%) as a yellow solid. MS m/z 553.5 [M+H]⁺.

Example 4. Preparation of 6-((5-fluoro-4-(4-fluoro-1-isopropyl-2-methyl-1H-benzo[d]imidazol-6-yl)pyrimidin-2-yl)amino)-N-hydroxynicotinamide (Compound 4)

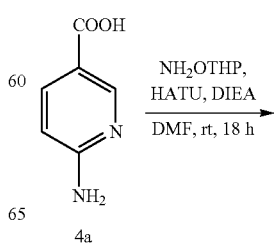

4a

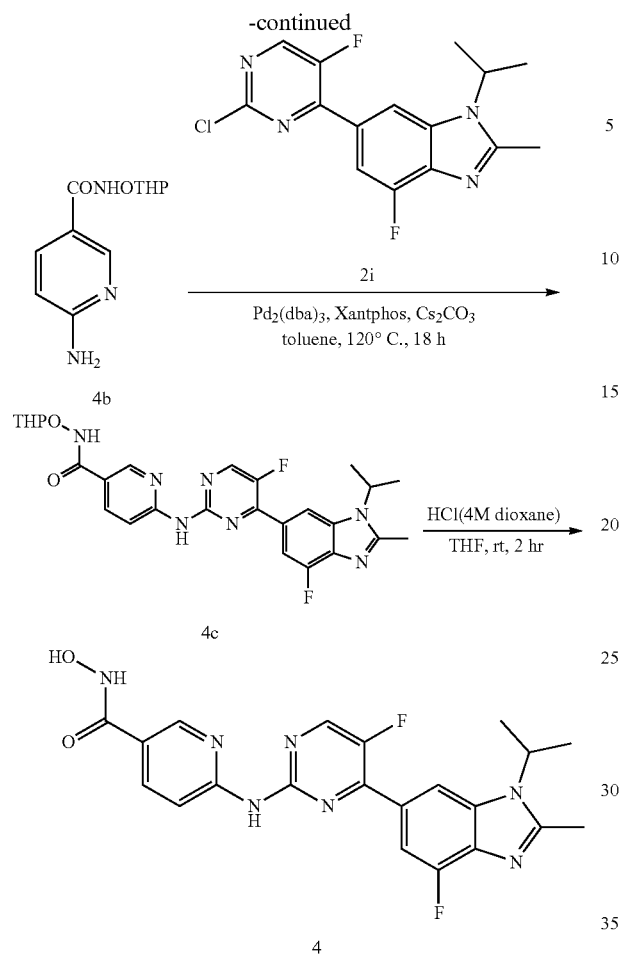

acetonitrile to afford compound 4 hydrochloride salt (2 mg, yield: 18%) as a yellow solid. MS m/z 440.3 [M+H]+.

Example 5. Preparation of (E)-3-(6-((5-fluoro-4-(4-fluoro-1-isopropyl-2-methyl-1H-benzo[d]imidazol-6-yl)pyrimidin-2-yl)amino)pyridin-3-yl)-N-hydroxyacrylamide (Compound 5)

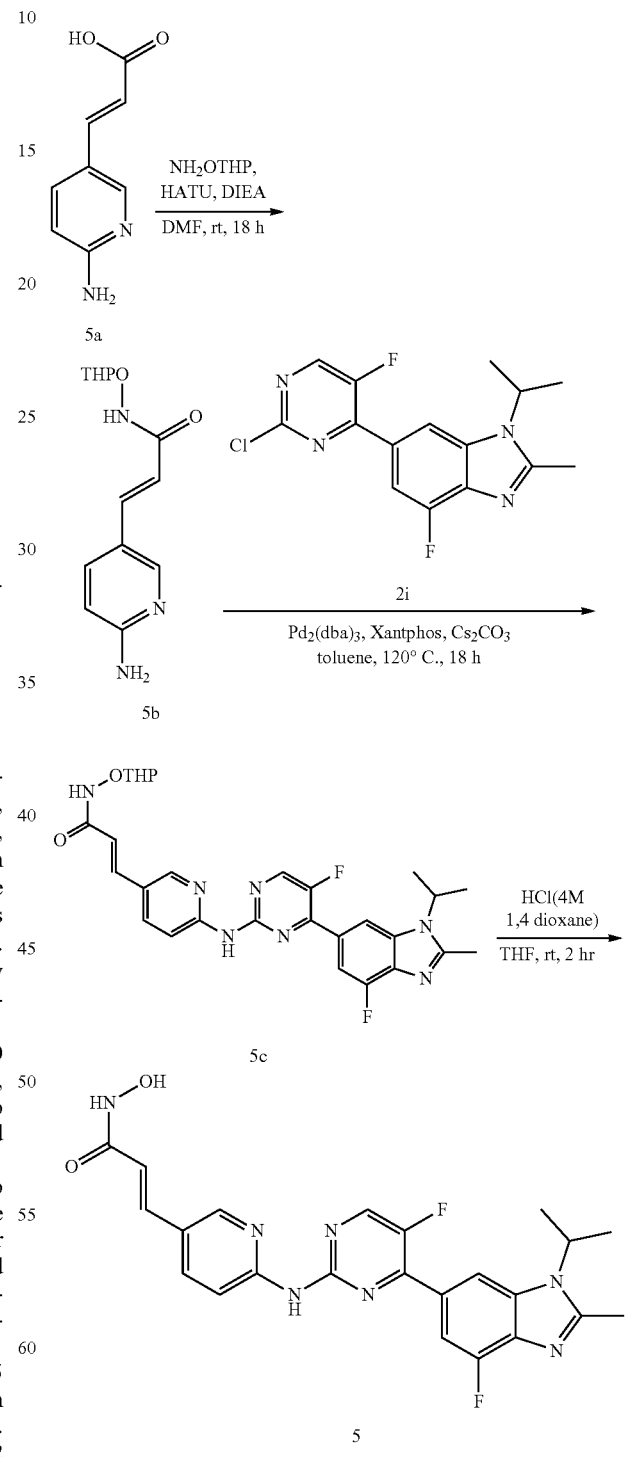

Compound 4a (100 mg, 0.72 mmol), N,N-diisopropylethylamine (280 mg, 2.17 mmol), HATU (413 mg, 1.09 mmol), and o-(tetrahydro-2-1-pyran-2-yl)hydroxylamine (102 mg, 0.87 mmol) were added to DMF (15 mL). The reaction mixture was stirred at room temperature for 2 hours. The reaction was monitored by TLC for completion. It was poured into water, and the solid was collected via filtration. The solid was purified by SiO2 column chromatography (dichloromethane:methanol=25:1~15:1) to afford compound 4b (100 mg, yield: 58%) as a yellow solid.

Compound 4b (20 mg, 0.084 mmol), 2i (32 mg, 0.10 mmol, Pd2(dba)3 (15 mg, 0.017 mmol), xantphos (73 mg, 0.13 mmol), and Cs2CO3 (82 mg, 0.25 mmol) were added to anhydrous toluene (3 mL). The reaction mixture was stirred at 120° C. under N2 atmosphere for 18 hours.

After cooling to room temperature, it was poured into water, and extracted with ethyl acetate (three times). The combined organic layers were washed with brine, dried over anhydrous sodium sulfate, and concentrated under reduced pressure. The residue was purified by SiO2 column chromatography (dichloromethane/methanol=20:1) to afford compound 4c (8 mg, yield: 18%) as a yellow solid Compound 4c (8 mg, 0.043 mmol) was added to THF (0.5 mL) at room temperature followed by the addition of HCl in 1, 4-dioxane (4 M, 2 drops) and deionized water (2 drops). The reaction mixture was stirred at room temperature for 2 hours. The reaction was monitored by TLC for completion. Et2O was added to the filtrate and the precipitate was collected via filtration. The solid was washed with Et2O and Compound 5a (100 mg, 0.61 mmol), N,N-diisopropylethylamine (236 mg, 1.83 mmol), HATU (347 mg, 0.91 mmol), and o-(tetrahydro-2H-pyran-2-yl)hydroxylamine (86 mg, 0.73 mmol) were added to dry DMF (5 mL). The reaction mixture was stirred at room temperature for 28 hours. The reaction was monitored by TLC for completion. It was poured into water, and the solid was collected via filtration. The solid was purified by $SiO_2$ column chromatography (dichloromethane/methanol=25:1~15:1) to afford compound 5b (80 mg, yield: 50%) as a yellow solid.

Compound 5b (20 mg, 0.076 mmol), 2i (29 mg, 0.09 mmol, $Pd_2(dba)_3$ (14 mg, 0.015 mmol), xantphos (66 mg, 0.11 mmol), and Cs2CO3 (74 mg, 0.253 mmol) were added to anhydrous toluene (3 mL). The reaction mixture was stirred at 120° C. under N2 atmosphere for 18 hours. After cooling to room temperature, it was poured into water, and extracted with ethyl acetate (three times). The combined organic layers were washed with brine, dried over anhydrous sodium sulfate, and concentrated under reduced pressure. The residue was purified by SiO2 column chromatography (dichloromethane/methanol=20:1) to afford compound 5c (8 mg, yield: 19%) as a yellow solid.

Compound 5c (8 mg, 0.015 mmol) was added to THF (0.5 mL) at room temperature followed by the addition of HCl in 1, 4-dioxane (4 M, 2 drops) and deionized water (2 drops). The reaction mixture was stirred at room temperature for 2 hours. The reaction was monitored by TLC for completion. $Et_2O$ was added to the filtrate and the precipitate was collected via filtration. The solid was washed with $Et_2O$ and acetonitrile to afford compound 5 hydrochloride salt (2 mg, yield: 27%) as a yellow solid. MS m/z 466.3 $[M+H]^+$.

Example 6. Preparation of 4-(((6-((5-fluoro-4-(4-fluoro-1-isopropyl-2-methyl-1H-benzo[d]imidazol-6-yl)pyrimidin-2-yl)amino)pyridin-3-yl)(methyl)amino)methyl)-N-hydroxybenzamide (Compound 6)

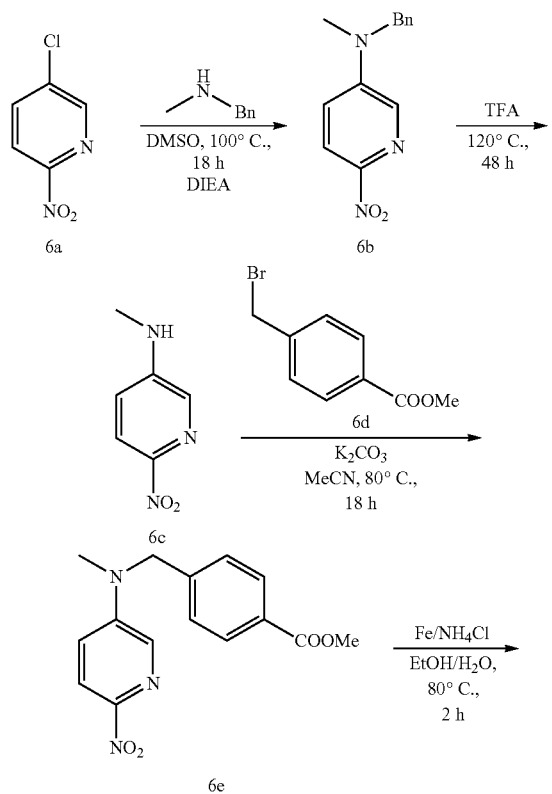

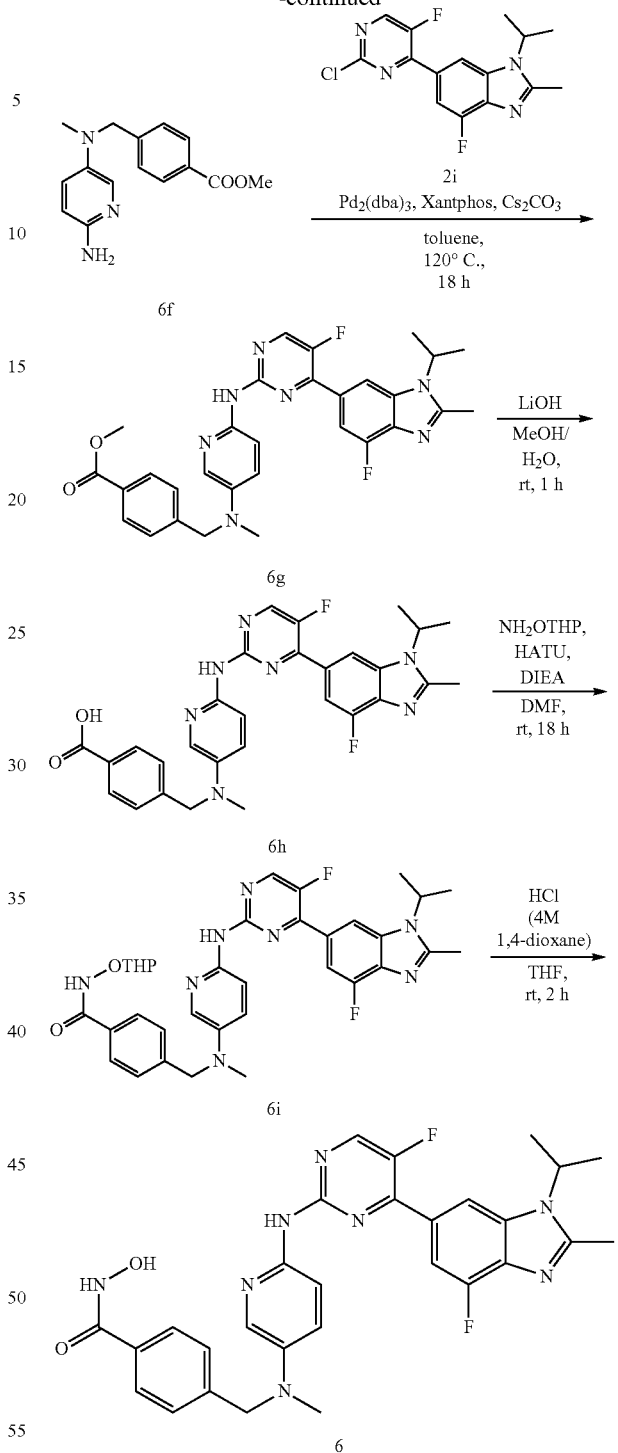

Compound 6a (5.0 g, 31.54 mmol), N-methylbenzylamine (5.7 g, 47.31 mmol), and DIPEA (8.2 g, 63.08 mmol) were added to DMSO (30 mL). The reaction mixture was heated to 100° C. for 18 hours. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure. The residue was purified by SiO2 column chromatography (dichloromethane:methanol=20:1) to afford compound 6b (5.0 g, yield: 65%) as a yellow solid.

Compound 6b (5.0 g, 20.55 mmol) was added to TFA (20 mL) and the reaction mixture was heated to 120° C. for 48 hours. The reaction was monitored by TLC for completion. After cooling to room temperature, it was poured into saturated aqueous NaHCO₃, and extracted with ethyl acetate (three times). The combined organic layers were washed with brine, dried over anhydrous sodium sulfate, and concentrated under reduced pressure. The residue was purified by SiO2 column chromatography (dichloromethane:methanol=10:1) to afford compound 6c (0.5 g, yield: 16%) as a yellow solid.

Compound 6c (0.1 g, 0.65 mmol), compound 6d (0.22 g, 0.98 mmol), and potassium carbonate (0.28 g, 1.96 mmol) were added to acetonitrile (10 mL). The reaction mixture was stirred at 80° C. for 18 hours. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure. The residue was purified by SiO$_2$ column chromatography to afford compound 6e (0.12 g, yield: 61%) as a yellow solid.

Compound 6e (50 mg, 0.17 mmol), Fe (46 mg, 0.83 mmol), and NH4Cl (44 mg, 0.83 mmol) were added to a mixture of ethanol and water (5:1, 10 mL) The reaction mixture was stirred at 80° C. for 2 hours. The reaction was monitored by TLC for completion. It was filtered and concentrated to remove ethanol. Water was added to the residue, and extracted with ethyl acetate (three times). The combined organic layers were washed with brine, dried over anhydrous sodium sulfate, and concentrated under reduced pressure. The residue was purified by SiO2 column chromatography (dichloromethane:methanol=10:1) to afford compound 6f (25 mg, yield: 55%) as a white solid.

Compound 6f (25 mg, 0.092 mmol), 2i (36 mg, 0.11 mmol), Pd2(dba)3 (17 mg, 0.018 mmol), xantphos (80 mg, 0.14 mmol), and Cs2CO3 (90 mg, 0.28 mmol) were added to anhydrous toluene (5 mL) The reaction mixture was stirred at 120° C. under N2 atmosphere for 18 hours. After cooling to room temperature, it was poured into water, and extracted with ethyl acetate (three times). The combined organic layers were washed with brine, dried over anhydrous sodium sulfate, and concentrated under reduced pressure. The residue was purified by SiO2 column chromatography (dichloromethane:methanol=20:1) to afford compound 6g (15 mg, yield: 30%) as a yellow solid.

Compound 6g (15 mg, 0.027 mmol) and lithium hydroxide monohydrate (12 mg, 0.27 mmol) were added to a mixture of methanol (5 mL) and water (1 mL). The reaction mixture was stirred at room temperature for 1 hour. The reaction was monitored by TLC for completion. It was concentrated to remove methanol, acidified with aqueous HCl (2 M) to pH=5, and extracted with ethyl acetate (three times). The combined organic layers were concentrated under reduced pressure to afford compound 6h (12 mg, yield: 82%) as a yellow solid (The compound was used in next step without further purification).

Compound 6h (12 mg, 0.022 mmol), N,N-diisopropylethylamine (8 mg, 0.066 mmol), HATU (13 mg, 0.033 mmol), and o-(tetrahydro-2H-pyran-2-yl)hydroxylamine (3 mg, 0.026 mmol) were added to dry DMF (2 mL). The reaction mixture was stirred at room temperature for 18 hours. The reaction was monitored by TLC for completion. It was poured into water, and the precipitate solid was collected via filtration, and purified by SiO$_2$ column chromatography (dichloromethane:methanol=25:1~15:1) to afford compound 6i (8 mg, yield: 56%) as a yellow solid.

Compound 6i (8 mg, 0.012 mmol) was added to THF (1 mL) at room temperature followed by the addition of HCl in 1, 4-dioxane (4 M, 1 drop) and deionized water (1 drop). The reaction mixture was stirred at room temperature for 5 hours. The reaction was monitored by TLC for completion. Et$_2$O was added to the filtrate and the precipitate was collected via filtration. The solid was washed with Et$_2$O and acetonitrile to afford compound 6 hydrochloride salt (2 mg, yield: 27%) as a yellow solid. MS m/z 559.5 [M+H]$^+$.

Example 7. Preparation of (E)-3-(4-(((6-((5-fluoro-4-(4-fluoro-1-isopropyl-2-methyl-1H-benzo[d]imidazol-6-yl)pyrimidin-2-yl)amino)pyridin-3-yl)(methyl)amino)methyl)phenyl)-N-hydroxyacrylamide (Compound 7)

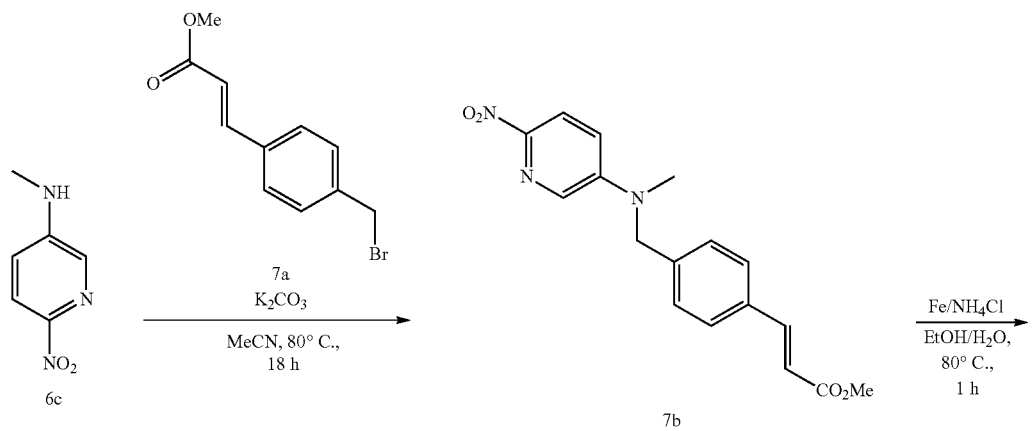

-continued
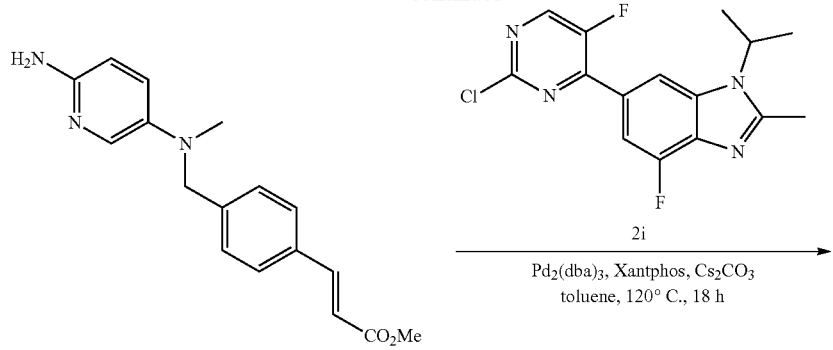
7c
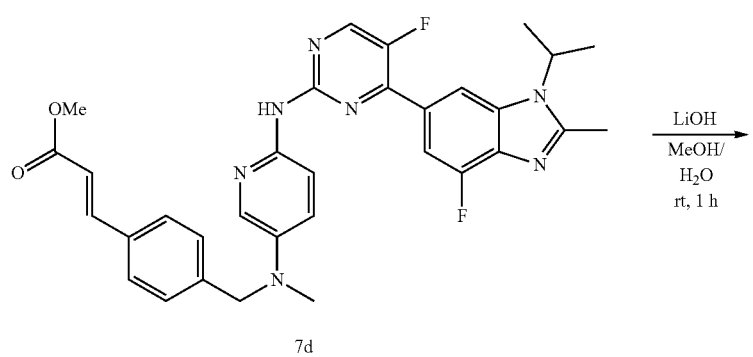
7d
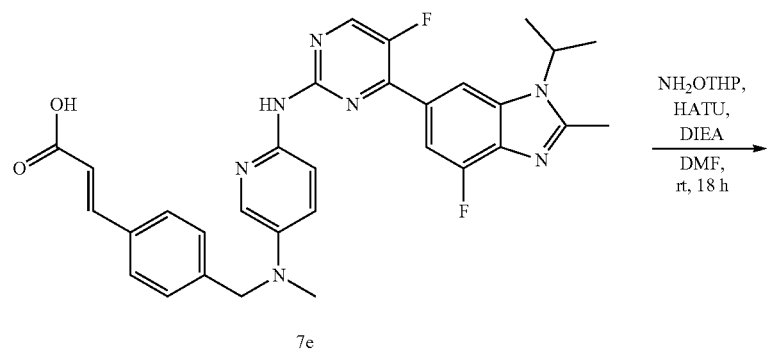
7e
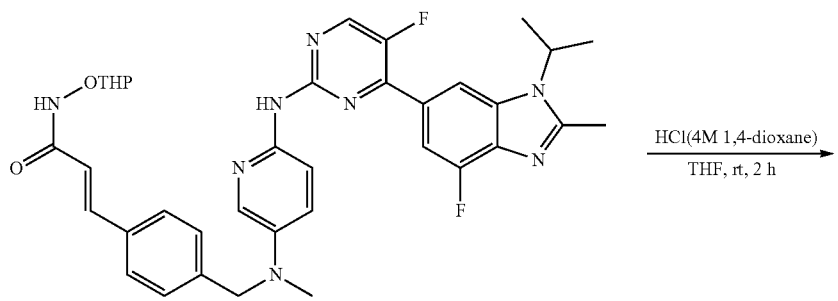
7f

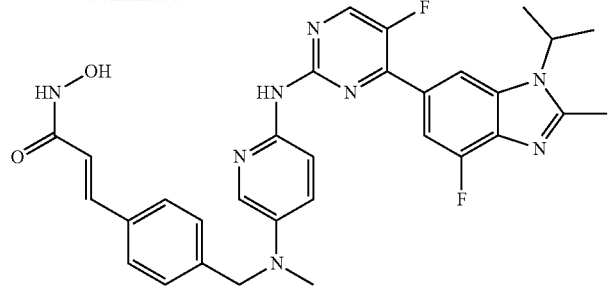

7

Compound 6c (0.1 g, 0.65 mmol), 7a (0.25 g, 0.98 mmol), and potassium carbonate (0.27 g, 1.96 mmol) were added to acetonitrile (10 mL). The reaction mixture was heated to 80° C. for 18 hours. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure. The residue was purified by $SiO_2$ column chromatography to afford compound 7b (80 mg, yield: 34%) as a yellow solid.

Compound 7b (80 mg, 0.23 mmol), Fe (65 mg, 1.17 mmol), and NH4Cl (63 mg, 1.17 mmol) were added to a mixture of ethanol and water (5:1, 10 mL). The reaction mixture was heated to 80° C. for 2 hours. The reaction was monitored by TLC for completion. After cooling to room temperature, it was poured into water, and extracted with ethyl acetate (three times). The combined organic layers were washed with brine, dried over anhydrous sodium sulfate, and concentrated under reduced pressure. The residue was purified by SiO2 column chromatography (dichloromethane:methanol=20:1) to afford compound 7c (50 mg, yield: 68%) as a yellow solid.

Compound 7c (50 mg, 0.16 mmol), 2i (62 mg, 0.62 mmol), Pd2(dba)3 (29 mg, 0.032 mmol), xantphos (139 mg, 0.24 mmol), and Cs2CO3 (160 mg, 0.48 mmol) were added to toluene (5 mL). The reaction mixture was heated at 120° C. under N2 atmosphere for 1 hour. After cooling to room temperature, it was poured into water, and extracted with ethyl acetate (three times). The combined organic layers were washed with brine, dried over anhydrous sodium sulfate, and concentrated under reduced pressure. The residue was purified by SiO2 column chromatography (dichloromethane:methanol=20:1) to afford compound 7d (20 mg, yield: 21%) as a yellow solid.

Compound 7d (20 mg, 0.034 mmol) and hydroxide monohydrate (14 mg, 0.34 mmol), were added to a mixture of methanol (5 mL) and water (1 mL). The reaction mixture was stirred at room temperature for 1 hour. The reaction was monitored by TLC for completion. It was concentrated to remove methanol, acidified with aqueous HCl (2 M) to pH=5, and extracted with ethyl acetate (three times). The combined organic layers were concentrated to afford compound 7e (15 mg, yield: 75%) as a yellow solid (The compound was used in next step without further purification).

Compound 7e (15 mg, 0.026 mmol), N,N-diisopropylethylamine (9 mg, 0.079 mmol), HATU (15 mg, 0.039 mmol), and o-(tetrahydro-2H-pyran-2-yl)hydroxylamine (4 mg, 0.040 mmol) were added to dry DMF (2 mL). The reaction mixture was stirred at 50° C. for 2 hours. The reaction was monitored by TLC for completion. It was poured into water, and the precipitate solid was collected via filtration. The solid was purified by SiO2 column chromatography (dichloromethane:methanol=25:1~15:1) to afford compound 7f (10 mg, yield: 57%) as a yellow solid.

Compound 7f (10 mg, 0.015 mmol) was added to THF (1 mL) at room temperature followed by the addition of 4 M HCl in 1, 4-dioxane (1 drop) and deionized water (1 drop). The reaction mixture was stirred at room temperature for 2 hours. The reaction was monitored by TLC for completion. Et2O was added to the filtrate and the precipitate was collected via filtration. The solid was washed with Et2O and acetonitrile to afford compound 7 hydrochloride salt (4 mg, yield: 43%) as a yellow solid compound. MS m/z 585.5 $[M+H]^+$.

Example 8. Preparation of 4-((4-(6-((5-fluoro-4-(4-fluoro-1-isopropyl-2-methyl-1H-benzo[d]imidazol-6-yl)pyrimidin-2-yl)amino)pyridin-3-yl)piperazin-1-yl)methyl)-N-hydroxybenzamide hydrochloride salt (Compound 8)

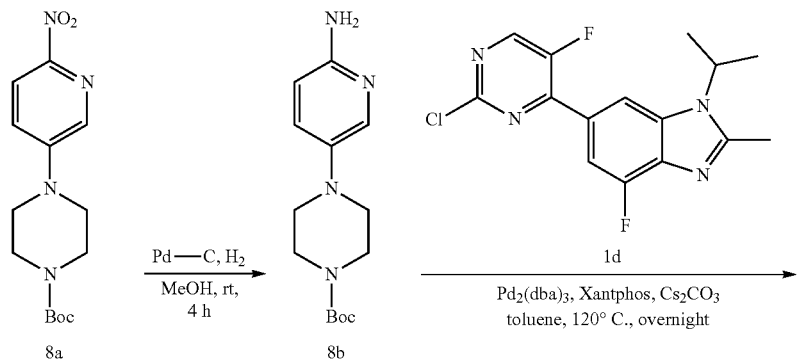

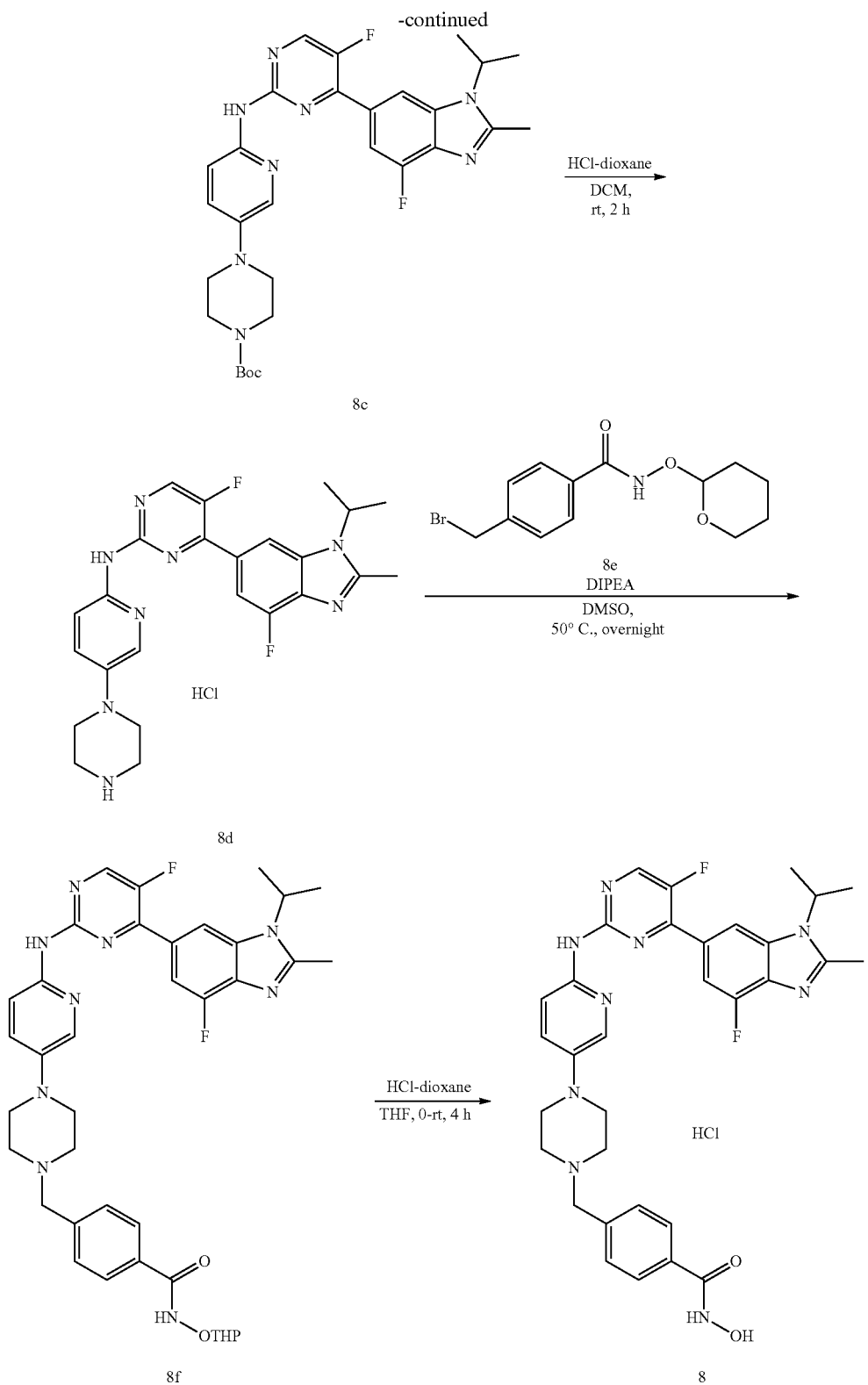

Compound 8a (2.0 g, 6.49 mmol) and Pd/C (10%, 200 mg) were added to methanol (20 mL) at room temperature, and the reaction mixture was stirred under H2 atmosphere at normal pressure for 4 hours. The reaction was monitored by TLC for completion. The reaction mixture was filtered through celite, and the filtrate was concentrated under reduced pressure. The residue was purified by SiO2 column chromatography (dichloromethane:methanol=20:1) to afford compound 8b (1.62 g, yield 90%).

Compound 8b (1.0 g, 3.59 mmol), compound 1d (1.39 g, 4.31 mmol), cesium carbonate (2.34 g, 7.19 mmol), Pd2(dba)3 (0.66 g, 0.72 mmol) and xantphos (0.72 g, 1.44 mmol) were added to dry toluene (20 mL) placed in a sealed tube under N2 atmosphere was heated to 120° C. overnight. The reaction mixture was filtered and the filtrate was concentrated under reduced pressure. The residue was purified by SiO2 column chromatography (dichloromethane:methanol=30:1) to afford compound 8c (1.6 g, yield 79%).

Compound 8c (1.50 g, 2.66 mmol) was dissolved in dichloromethane (10 mL), and a solution of HCl in 1,4-dioxane (4 M, 5 mL) was added. The reaction mixture was stirred at room temperature for 2 hours. The reaction was monitored by TLC for completion. The reaction mixture was concentrated under reduced pressure to afford compound 8d (1.33 g, yield 100%) as a yellow solid.

Compound 8d (50 mg, 0.10 mmol), 8e (38 mg, 0.12 mmol), DIPEA (39 mg, 0.30 mmol) were dissolved in DMSO (5 mL), and the reaction mixture was heated to 50° C. overnight. After cooling to room temperature, the reaction mixture was quenched with water, extracted with ethyl acetate. The combined organic layers were washed with brine, dried over anhydrous sodium sulfate, and concentrated to afford compound 8f (32 mg, 46%).

Compound 8f (32 mg, 0.05 mmol) was dissolved in THF (5 mL) followed by the addition of a solution of HCl in 1,4-dioxane (4 M, 2 mL) under ice bath. The reaction mixture was stirred at room temperature for 4 hours. The reaction was monitored by TLC for completion. The reaction mixture was concentrated under reduced pressure to remove 1,4-dioxane and THF.

Acetonitrile was added and the precipitate was collected by filtrated, washed with Et2O to give compound 8 (12 mg, yield 40%) as a yellow solid. 1H NMR (500 MHz, CD3OD) δ 8.84 (d, J=3.3 Hz, 1H), 8.55 (s, 1H), 8.27 (dd, J=9.7, 2.9 Hz, 1H), 8.15 (d, J=11.2 Hz, 1H), 7.90 (dd, J=11.6, 5.6 Hz, 3H), 7.73 (d, J=8.2 Hz, 2H), 7.57 (d, J=9.6 Hz, 1H), 5.12 (m, 1H), 4.53 (s, 2H), 3.93 (s, 2H), 3.61 (d, J=19.3 Hz, 2H), 3.46-3.37 (m, 2H), 3.33-3.31 (m, 2H), 2.94 (s, 3H), 1.80 (d, J=6.9 Hz, 6H). MS m/z 614.6 [M+H]+.

Example 9. Preparation of 7-(4-(6-((5-fluoro-4-(4-fluoro-1-isopropyl-2-methyl-1H-benzo[d]imidazol-6-yl)pyrimidin-2-yl)amino)pyridin-3-yl)piperazin-1-yl)-N-hydroxyheptanamide hydrochloride salt (Compound 9)

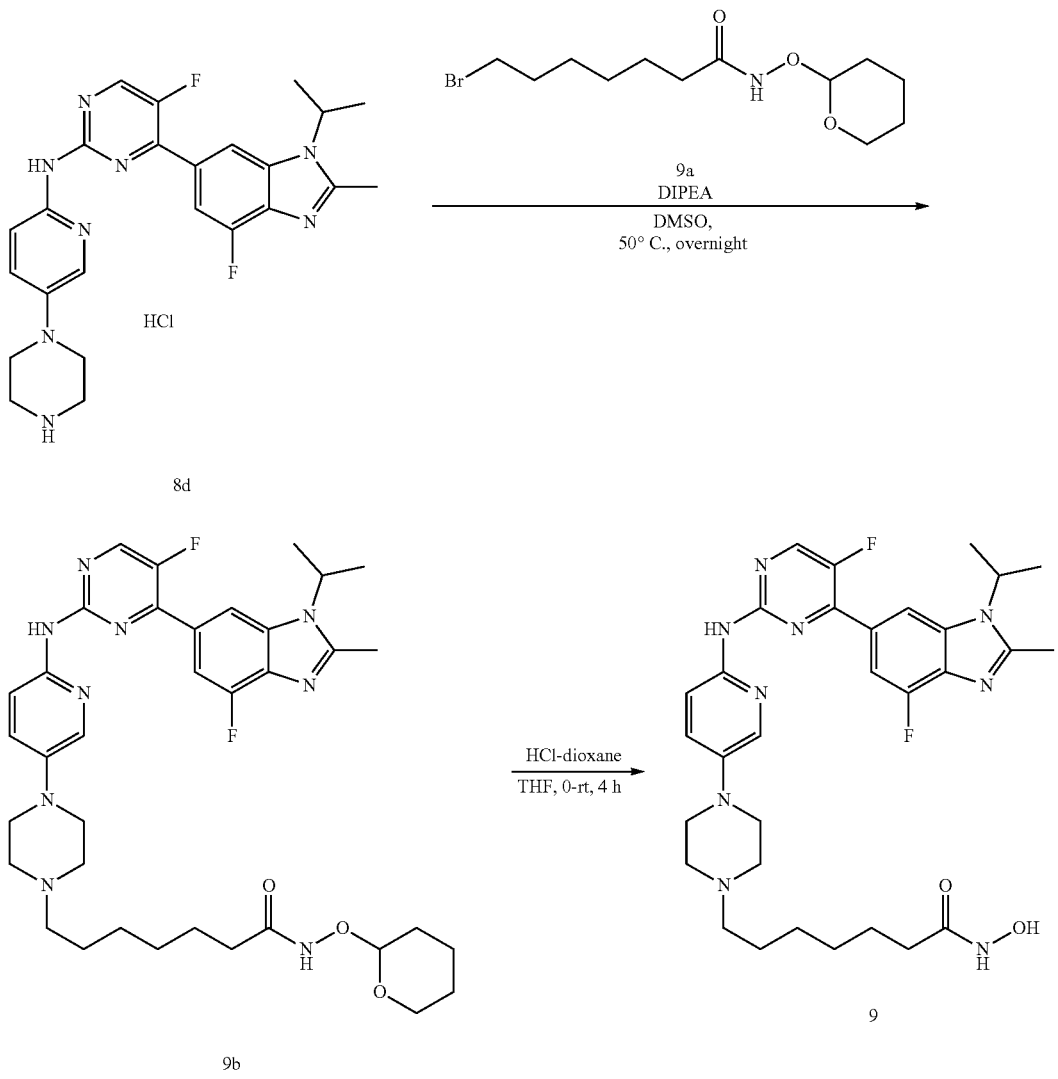

Compound 9b was prepared following the procedure of compound 8f.

Compound 9 was prepared following the procedure of compound 8. 1H NMR (500 MHz, DMSO-d6) δ 11.56 (s, 1H), 11.21 (s, 1H), 10.33 (d, J=70.7 Hz, 1H), 8.85 (s, 1H), 8.30 (s, 1H), 8.11 (s, 1H), 8.00 (d, J=2.8 Hz, 1H), 7.86 (d, J=9.5 Hz, 1H), 7.79 (d, J=11.2 Hz, 1H), 4.91 (m, 1H), 3.83 (d, J=12.6 Hz, 4H), 3.61 (d, J=12.2 Hz, 2H), 3.14 (dt, J=19.6, 5.9 Hz, 4H), 2.74 (s, 3H), 1.96 (t, J=7.3 Hz, 2H), 1.75 (s, 2H), 1.64 (d, J=6.9 Hz, 6H), 1.52 (dd, J=14.3, 7.1 Hz, 2H), 1.30 (d, J=3.0 Hz, 4H). MS m/z 608.5 [M+H]$^+$.

Example 10. Preparation of 8-(4-(6-((5-fluoro-4-(4-fluoro-1-isopropyl-2-methyl-1H-benzo[d]imidazol-6-yl)pyrimidin-2-yl)amino)pyridin-3-yl)piperazin-1-yl)-N-hydroxy-8-oxooctanamide (Compound 10)

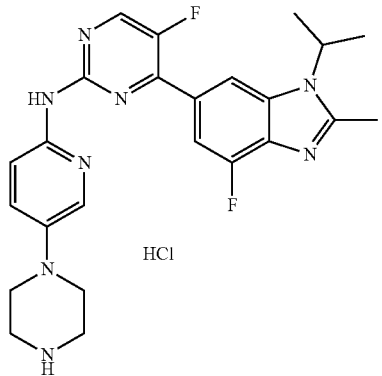
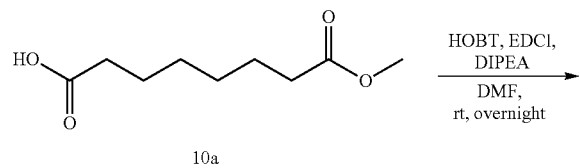

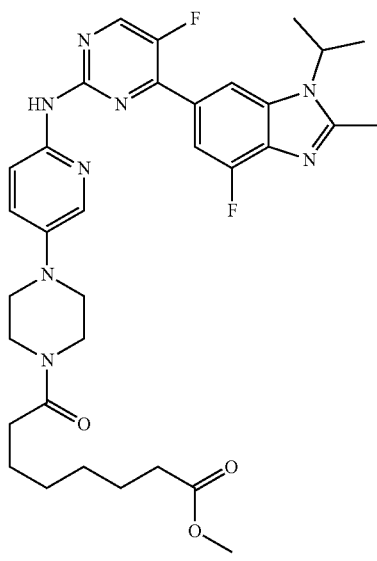
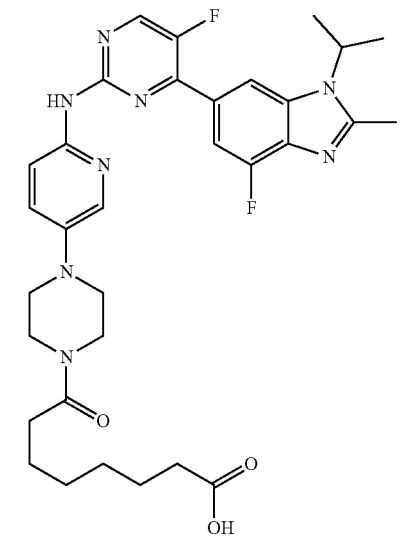

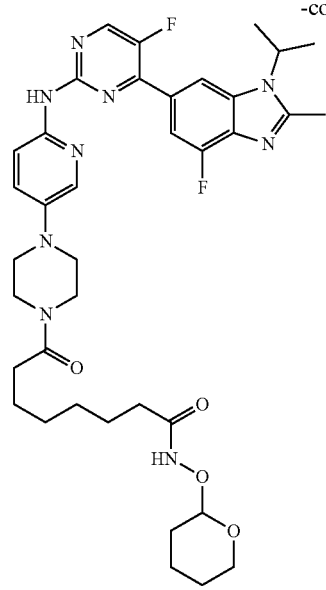

10d

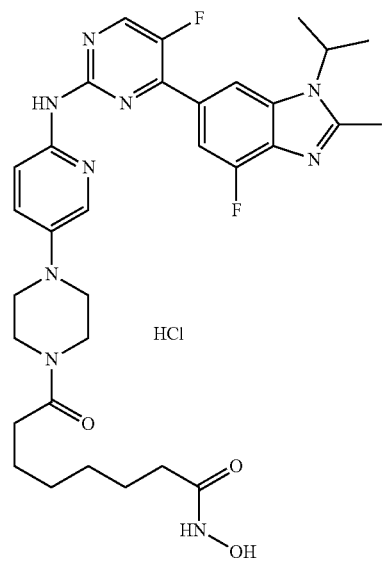

10

Compound 8d (100 mg, 0.20 mmol), 10a (45 mg, 0.24 mmol), HOBT (41 mg, 0.30 mmol), EDCI (58 mg, 0.30 mmol), and DIPEA (52 mg, 0.40 mmol) were dissolved in DMF (5 mL). The reaction mixture was stirred at room temperature overnight. Water was added, and extracted with EtOAc. The combined organic layers were washed with brine, dried over anhydrous sodium sulfate, and concentrated under reduced pressure. The residue was purified by SiO₂ column chromatography (dichloromethane:EtOAc=1:1) to afford compound 10b (86 mg, yield 68%).

Compound 10b (86 mg, 0.14 mmol) was dissolved in methanol (5 mL) followed by the addition of LiGH (16 mg, 0.68 mmol). The reaction mixture was stirred at room temperature overnight. It was concentrated to give compound 10c, which was used in next step without purification.

Compound 10c (84 mg, 0.14 mmol), o-(tetrahydro-2H-pyran-2-yl)hydroxylamine (19 mg, 0.16 mmol), HOBT (28 mg, 0.20 mmol), EDCI (39 mg, 0.20 mmol), and DIPEA (35 mg, 0.28 mmol) were dissolved in DMF (5 mL). The reaction mixture was stirred at room temperature overnight. Water was added, and extracted with a mixture of dichloromethane and methanol (10:1). The combined organic layers were washed with brine, dried over anhydrous sodium sulfate, and concentrated under reduced pressure. The residue was purified by SiO2 column chromatography (dichloromethane:methanol=50:1) to afford compound 10d (16 mg, yield 16%).

Compound 10 was prepared following the procedure of compound 8. 1H NMR (500 MHz, DMSO-d6) δ 11.76 (s, 1H), 10.36 (s, 1H), 8.87 (d, J=3.3 Hz, 1H), 8.29 (s, 1H), 8.20 (d, J=9.9 Hz, 1H), 7.89 (d, J=2.6 Hz, 1H), 7.77 (dd, J=15.7, 10.7 Hz, 2H), 4.92 (m, 1H), 3.64 (s, 4H), 3.22 (s, 2H), 3.17 (d, J=1.9 Hz, 2H), 2.74 (s, 3H), 2.36 (t, J=7.4 Hz, 2H), 1.93 (q, J=7.7 Hz, 2H), 1.64 (d, J=6.9 Hz, 6H), 1.52-1.45 (m, 4H), 1.27 (dd, J=11.7, 8.7 Hz, 4H). MS m/z 636.5 [M+H]+.

Example 11. 5-((5-fluoro-4-(4-fluoro-1-isopropyl-2-methyl-1H-benzo[d]imidazol-6-yl)pyrimidin-2-yl)amino)-N-hydroxypicolinamide hydrochloride salt (Compound 11)

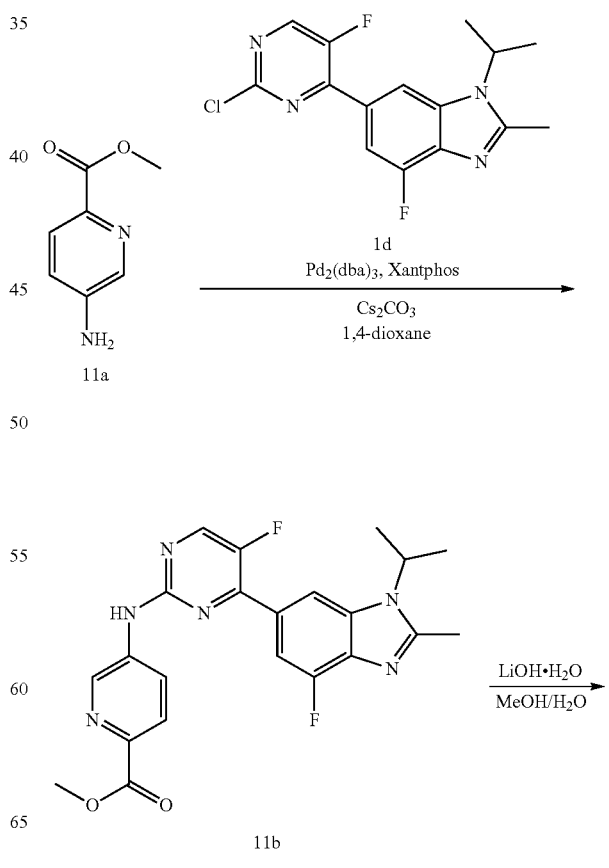

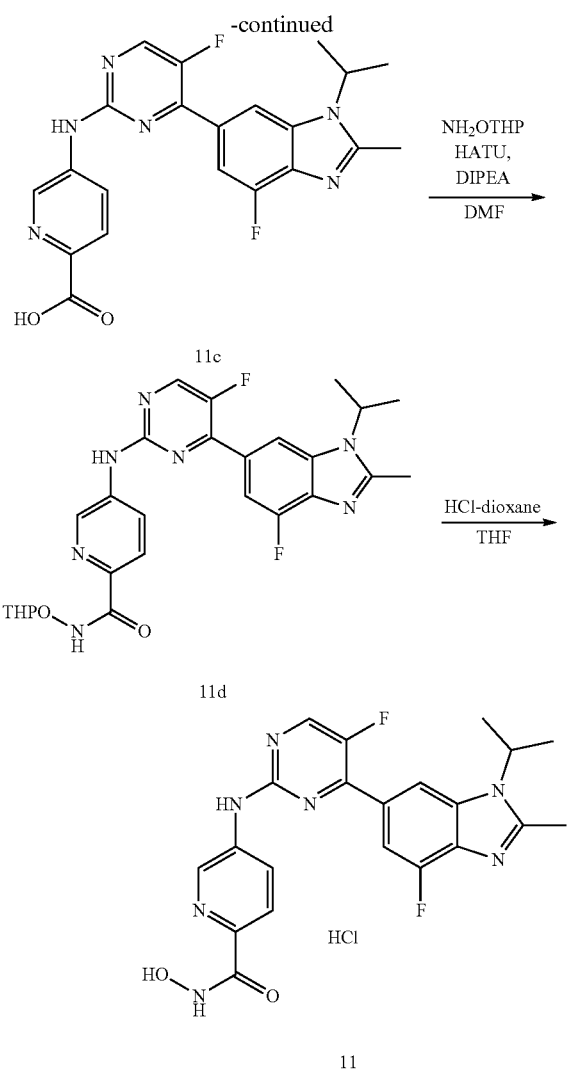

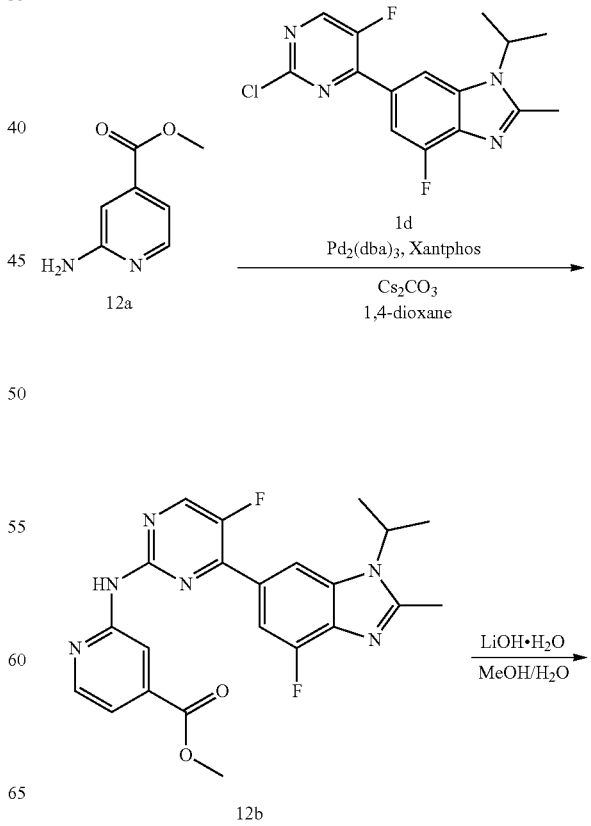

Compound 1d (400 mg, 1.24 mmol), 11a (189 mg, 1.24 mmol), caesium carbonate (1.2 g, 3.72 mmol), Pd2(dba)3 (114 mg, 0.12 mmol), and xantphos (144 mg, 0.25 mmol) were dissolved in 1,4-dioxane (10 mL) under N2 atmosphere. The reaction mixture was stirred at 110° C. for 5 hours. The reaction was monitored by TLC for completion. After cooling to room temperature, water (30 mL) was added with stirring, and the precipitate was collected via filtration. The solid was washed with methanol to afford compound 11b (468 mg) as a white solid, which was used in next step. MS m/z 439.4 [M+H]+.

Compound 11b (468 mg, 1.07 mmol) was dissolved in a mixture of methanol (20 mL) and water (2 mL) followed by the addition of lithium hydroxide monohydrate (137 mg, 3.21 mmol). The reaction mixture was stirred at 60° C. for 1 hour. The reaction was monitored by TLC for completion. It was concentrated in reduced pressure to remove most of methanol. Water (5 mL) was added to the residue, acidified with aqueous HCl (2 M) to pH=4-5, and extracted with ethyl acetate (3×10 mL). The combined organic layers were washed with brine, dried over anhydrous sodium sulfate, and filtered. The filtrate was concentrated under reduced pressure to afford compound 11c (328 mg) as a white solid, which was used in next step. MS m/z 425.4 [M+H]+.

Compound 11c (328 mg, 0.77 mmol), o-(tetrahydro-2H-pyran-2-yl)hydroxylamine (108 mg, 0.92 mmol), o-(7-azabenzotriazol-1-yl)-N,N,N',N'-tetramethyluronium hexafluorophosphate (441 mg, 1.16 mmol), and N,N-diisopropylethylamine (298 mg, 2.31 mmol) were dissolved in N,N-dimethylformamide (5 mL). The reaction mixture was stirred at room temperature for 1 hour. The reaction was monitored by TLC for completion. It was poured into ice water, and extracted with dichloromethane (3×20 mL). The combined organic layers were washed with brine, dried over anhydrous sodium sulfate and filtered. The filtrate was concentrated under reduced pressure. The residue was stirred in EtOAc (10 mL) and filtered to afford compound 11d (325 mg, yield 80%) as a white solid. MS m/z 524.5 [M+H]+.

Compound 11d (325 mg, 0.62 mmol) was dissolved in THF (5 mL) followed by the addition of a solution of HCl in 1,4-dioxane (4.0 M, 20 drops). The reaction mixture was stirred at room temperature for 2 hours. The reaction was monitored by TLC for completion. It was filtered and the solid was washed with acetonitrile to afford compound 11 hydrochloride salt (195 mg, yield 66%) as an off-white solid. 1H NMR (500 MHz, DMSO-d6) δ 10.46 (s, 1H), 8.95 (d, J=2.5 Hz, 1H), 8.81 (d, J=3.3 Hz, 1H), 8.47 (dd, J=8.7, 2.6 Hz, 1H), 8.36 (s, 1H), 7.97 (d, J=8.7 Hz, 1H), 7.89 (d, J=11.5 Hz, 1H), 5.05-4.93 (m, 1H), 2.85 (s, 3H), 1.67 (d, J=6.9 Hz, 6H). MS m/z 440.6 [M+H]+.

Example 12. Preparation 2-((5-fluoro-4-(4-fluoro-1-isopropyl-2-methyl-1H-benzo[d]imidazol-6-yl)pyrimidin-2-yl)amino)-N-hydroxyisonicotinamide hydrochloride salt (Compound 12)

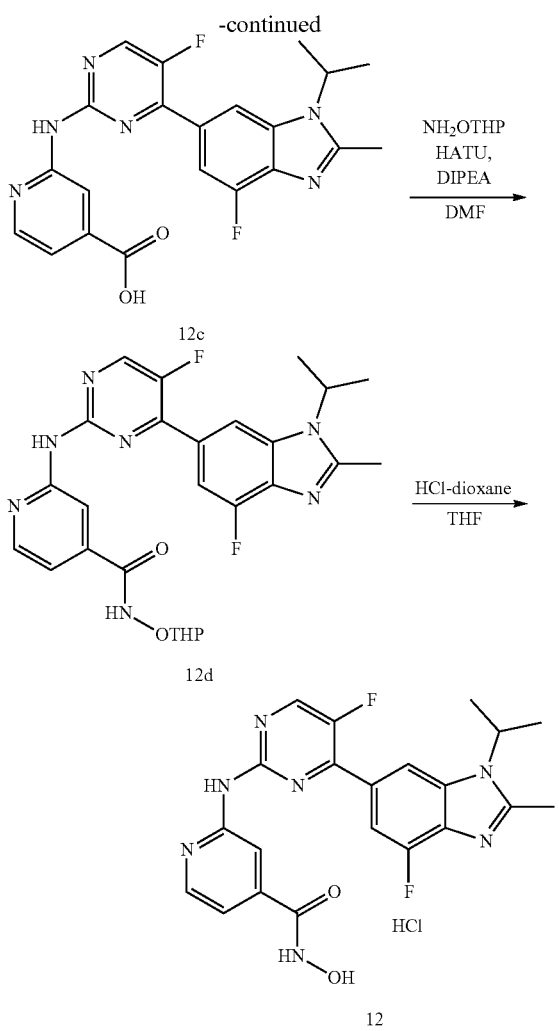

hexafluorophosphate (160 mg, 0.42 mmol), and N,N-diisopropylethylamine (108 mg, 0.84 mmol) were dissolved in N,N-dimethylformamide (3 mL). The reaction mixture was stirred at room temperature for 1 hour. The reaction was monitored by TLC for completion. It was poured into ice water, extracted with dichloromethane (3×20 mL). The combined organic layers were washed with brine, dried over anhydrous sodium sulfate and filtered. The filtrate was concentrated under reduced pressure. The residue was stirred in EtOAc (5 mL) and filtered to afford compound 12d (87 mg, yield 60%) as a white solid. MS m/z 524.5 [M+H]+.

Compound 12d (87 mg, 0.17 mmol) was dissolved in THF (2 mL) followed the addition of a solution of HCl in 1,4-dioxane (4.0 M, 10 drops). The reaction mixture was stirred at room temperature for 2 hours. The reaction was monitored by TLC for completion. It was filtered and the solid was washed with acetonitrile to afford compound 12 hydrochloride salt (49 mg, yield 62%) as an off-white solid. 1H NMR (500 MHz, DMSO-d6) δ 11.58 (s, 1H), 8.90 (d, J=3.3 Hz, 1H), 8.48 (d, J=5.8 Hz, 1H), 8.41 (s, 1H), 8.40 (d, J=9.0 Hz, 1H), 7.95 (d, J=11.4 Hz, 1H), 7.50 (dd, J=5.8, 1.6 Hz, 1H), 5.04-4.94 (m, 1H), 2.85 (s, 3H), 1.67 (d, J=6.9 Hz, 6H). MS m/z 440.4 [M+H]+.

Example 13. Preparation of 5-(4-(6-((5-fluoro-4-(4-fluoro-1-isopropyl-2-methyl-1H-benzo[d]imidazol-6-yl)pyrimidin-2-yl)amino)pyridin-3-yl)piperazin-1-yl)-N-hydroxypentanamide hydrochloride salt (Compound 13)

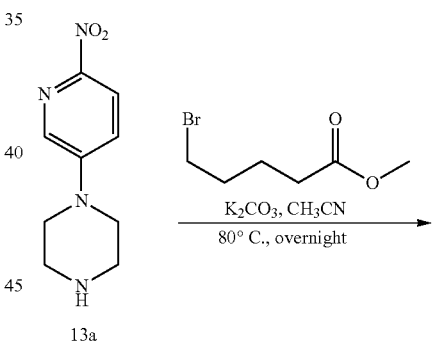

Compound 1d (200 mg, 0.62 mmol), 12a (94 mg, 0.62 mmol), cesium carbonate (606 mg, 1.86 mmol), Pd2(dba)3 (57 mg, 0.06 mmol), and xantphos (72 mg, 0.12 mmol) were dissolved in 1,4-dioxane (5 mL) under N2 atmosphere. The reaction mixture was stirred at 110° C. for 5 hour. The reaction was monitored by TLC for completion. After cooling to room temperature, it was diluted with methanol (15 mL), and filtered. The solid was washed with methanol to afford compound 12b (168 mg) as an off-white solid, which was used in next step. MS m z 439.4 [M+H]+.

Compound 12b (168 mg, 0.38 mmol) were dissolved in a mixture of methanol and water (10 mL/1 mL) followed by the addition of lithium hydroxide monohydrate (49 mg, 1.14 mmol). The reaction mixture was stirred at 60° C. for 1 hour. The reaction was monitored by TLC for completion. It was concentrated under reduced pressure to remove most of methanol. Water (5 mL) was added to the residue, acidified with aqueous HCl (2 M) to pH=4-5, and extracted with ethyl acetate (3×10 mL). The combined organic layers were washed with brine, dried over anhydrous sodium sulfate, and filtered. The filtrate was concentrated under reduced pressure to afford compound 12c (118 mg) as a white solid, which was used in next step. MS m/z 425.4 [M+H]+.

Compound 12c (118 mg, 0.28 mmol), o-(tetrahydro-2H-pyran-2-yl)hydroxylamine (40 mg, 0.34 mmol), o-(7-azabenzotriazol-1-yl)-N,N,N',N'-tetramethyluronium

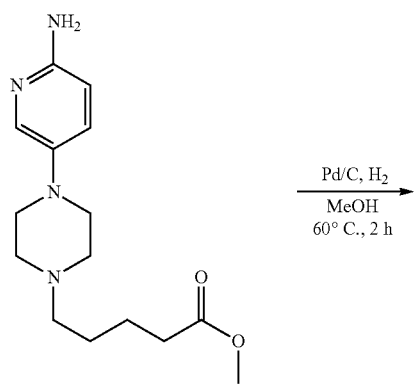

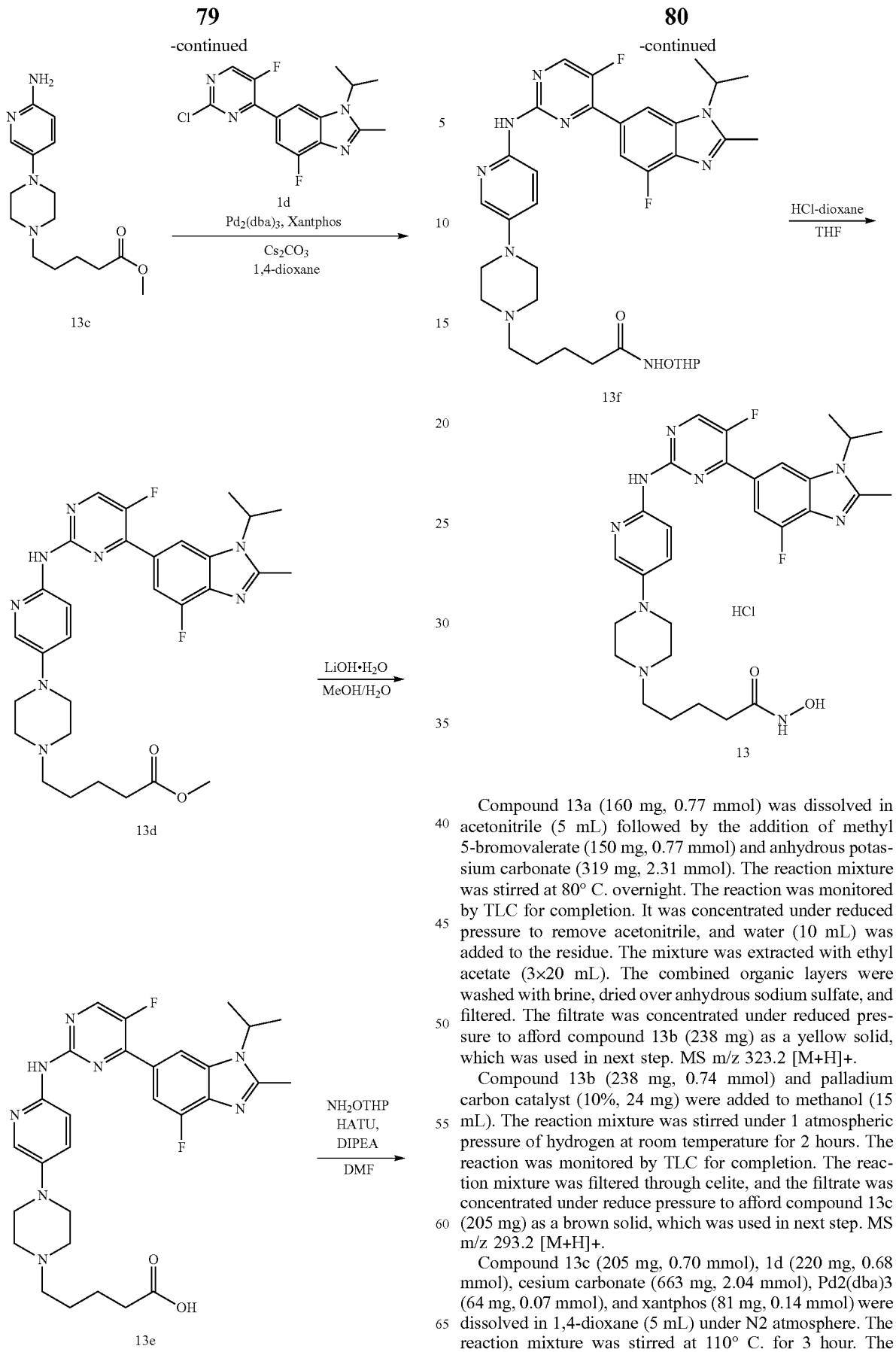

Compound 13a (160 mg, 0.77 mmol) was dissolved in acetonitrile (5 mL) followed by the addition of methyl 5-bromovalerate (150 mg, 0.77 mmol) and anhydrous potassium carbonate (319 mg, 2.31 mmol). The reaction mixture was stirred at 80° C. overnight. The reaction was monitored by TLC for completion. It was concentrated under reduced pressure to remove acetonitrile, and water (10 mL) was added to the residue. The mixture was extracted with ethyl acetate (3×20 mL). The combined organic layers were washed with brine, dried over anhydrous sodium sulfate, and filtered. The filtrate was concentrated under reduced pressure to afford compound 13b (238 mg) as a yellow solid, which was used in next step. MS m/z 323.2 [M+H]+.

Compound 13b (238 mg, 0.74 mmol) and palladium carbon catalyst (10%, 24 mg) were added to methanol (15 mL). The reaction mixture was stirred under 1 atmospheric pressure of hydrogen at room temperature for 2 hours. The reaction was monitored by TLC for completion. The reaction mixture was filtered through celite, and the filtrate was concentrated under reduce pressure to afford compound 13c (205 mg) as a brown solid, which was used in next step. MS m/z 293.2 [M+H]+.

Compound 13c (205 mg, 0.70 mmol), 1d (220 mg, 0.68 mmol), cesium carbonate (663 mg, 2.04 mmol), Pd2(dba)3 (64 mg, 0.07 mmol), and xantphos (81 mg, 0.14 mmol) were dissolved in 1,4-dioxane (5 mL) under N2 atmosphere. The reaction mixture was stirred at 110° C. for 3 hour. The reaction was monitored by TLC for completion. After cooling to room temperature, it was filtered through celite. The filtrate was concentrated under reduced pressure, and the residue was purified by SiO2 column chromatography (dichloromethane:methanol=10:1) to afford compound 13d (232 mg, yield 59%) as a yellow solid. MS m/z 579.3 [M+H]+.

Compound 13d (232 mg, 0.40 mmol) was dissolved in a mixture of methanol (10 mL) and water (1 mL) followed by the addition of lithium hydroxide monohydrate (51 mg, 1.20 mmol). The reaction mixture was stirred at 60° C. for 3 hours. The reaction was monitored by TLC for completion. It was concentrated under reduced pressure to remove most of methanol. Water (5 mL) was added, acidified with HCl (2 M) to pH=4-5, and extracted with ethyl acetate (3×10 mL). The combined organic layers were washed with brine, dried over anhydrous sodium sulfate, and filtered. The filtrate was concentrated under reduced pressure to afford compound 13e (175 mg) as a yellow solid, which was used in next step. MS m/z 565.3 [M+H]+.

Compound 13e (175 mg, 0.31 mmol), o-(tetrahydro-2H-pyran-2-yl)hydroxylamine (43 mg, 0.37 mmol), o-(7-azabenzotriazol-1-yl)-N,N,N',N'-tetramethyluronium hexafluorophosphate (211 mg, 0.56 mmol), and N,N-diisopropylethylamine (120 mg, 0.93 mmol) were added to N,N-dimethylformamide (3 mL). The reaction mixture was stirred at room temperature for 1 hour. The reaction was monitored by TLC for completion. It was poured into ice water, and extracted with dichloromethane (3×10 mL). The combined organic layers were washed with brine, dried over anhydrous sodium sulfate, and filtered. The filtrate was concentrated under reduced pressure, and the residue was purified by SiO2 column chromatography (dichloromethane:methanol=20:1) to afford compound 13f (93 mg, yield 45%) as a yellow solid. MS m/z 664.3 [M+H]+.

Compound 13f (93 mg, 0.14 mmol) was dissolved in THE (2 mL) followed by the addition of a solution of HCl in 1,4-dioxane (4.0 M, 10 drops). The reaction mixture was stirred at room temperature for 2 hours. The reaction was monitored by TLC for completion. It was filtered and the solid was washed with acetonitrile to afford compound 13 hydrochloride salt (59 mg, yield 68%) as a yellow solid. 1H NMR (500 MHz, CD3OD) δ 8.87 (d, J=3.2 Hz, 1H), 8.59 (s, 1H), 8.29 (dd, J=9.7, 2.6 Hz, 1H), 8.19 (d, J=11.0 Hz, 1H), 7.95 (d, J=2.7 Hz, 1H), 7.59 (d, J=9.6 Hz, 1H), 5.20-5.10 (m, 1H), 3.98-3.90 (m, 2H), 3.80-3.71 (m, 2H), 3.38-3.31 (m, 4H), 3.29-3.23 (m, 2H), 2.99 (s, 3H), 2.46-2.21 (m, 2H), 1.92-1.83 (m, 2H), 1.82 (d, J=6.9 Hz, 6H), 1.77-1.68 (m, 2H). MS m/z 580.7 [M+H]$^+$.

Example 14. Preparation of 3-(4-(6-((5-fluoro-4-(4-fluoro-1-isopropyl-2-methyl-1H-benzo[d]imidazol-6-yl)pyrimidin-2-yl)amino)pyridin-3-yl)piperazin-1-yl)-N-hydroxypropanamide hydrochloride salt (Compound 14)

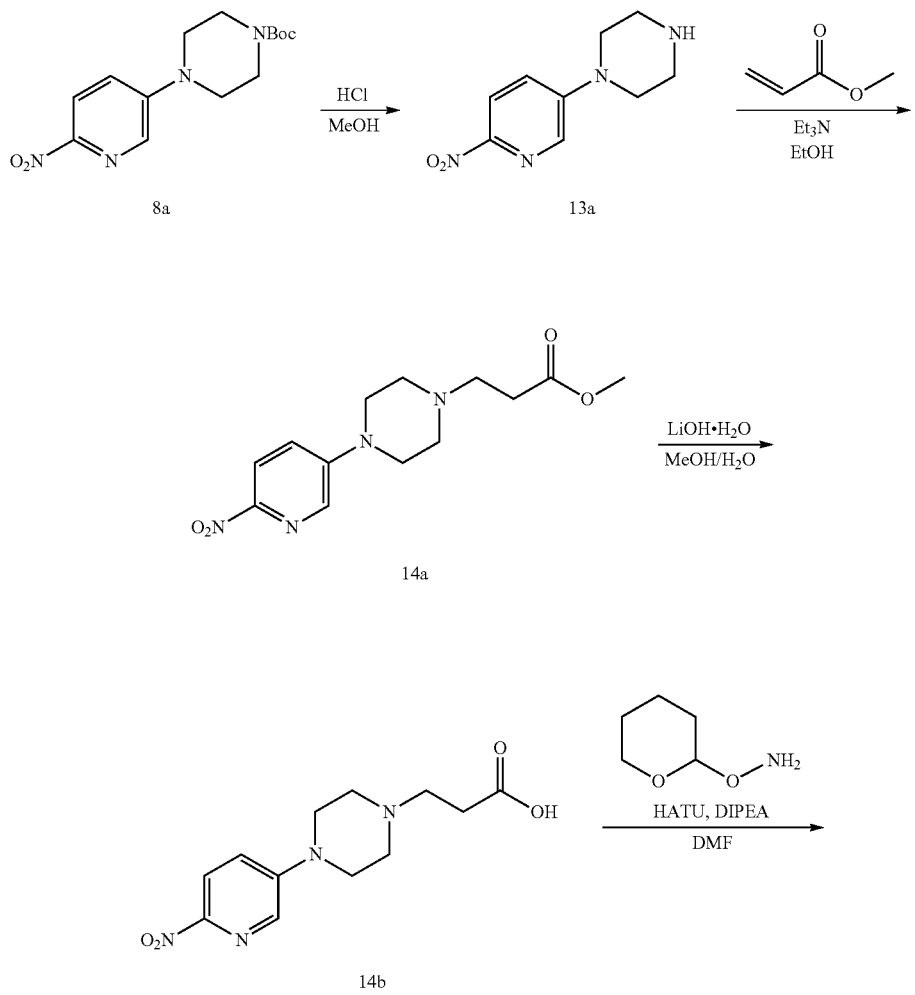

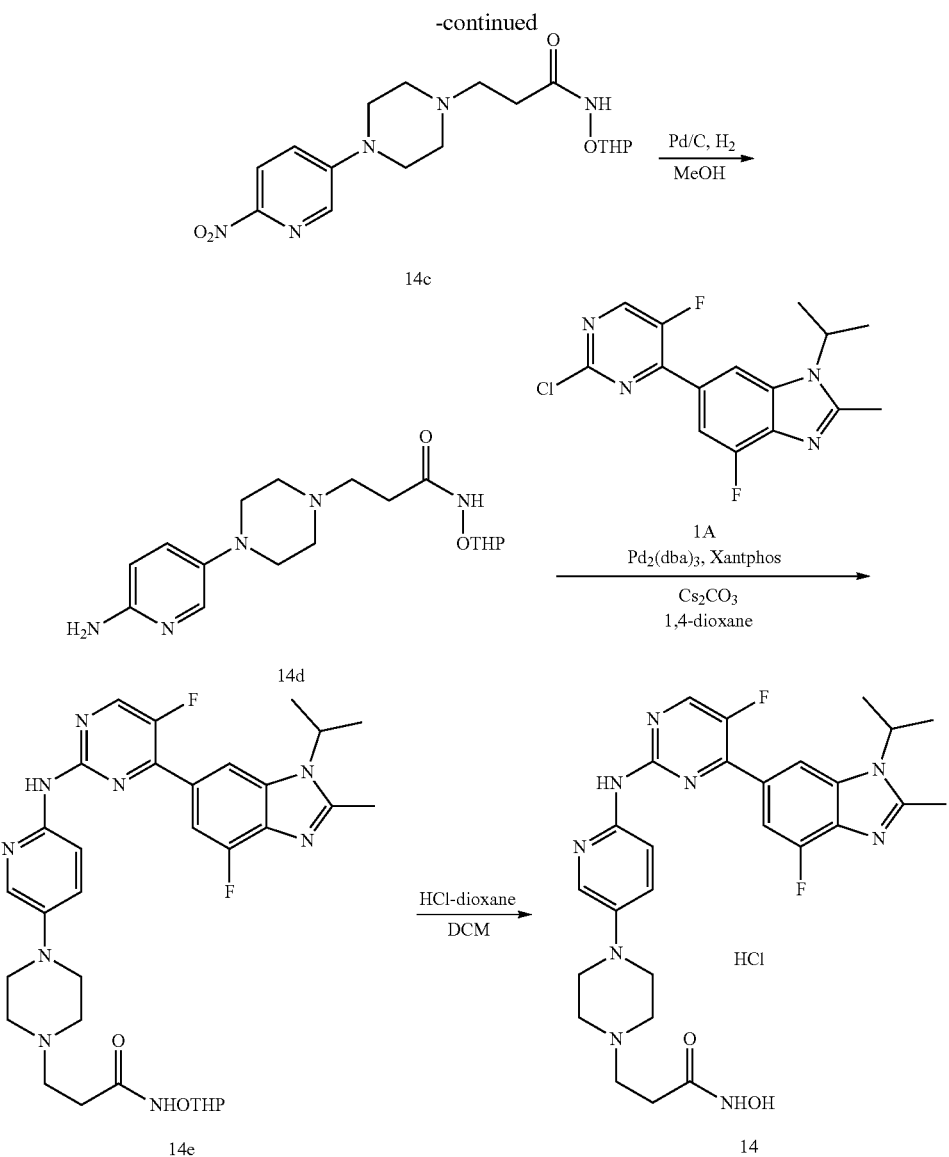

A solution of HCl in methanol (4.0 M, 1.82 mL) was added to a solution of compound 8a (1.5 g, 4.86 mmol) in methanol (40 mL). The reaction mixture was stirred at 65° C. for 2 hours. The reaction was monitored by TLC for completion. It was concentrated under reduced pressure and the residue was dissolved in dichloromethane. The mixture was neutralized with saturated aqueous sodium bicarbonate, and extracted with dichloromethane (3×30 mL). The combined organic layers were washed with brine, dried over anhydrous sodium sulfate and filtered. The filtrate was concentrated under reduced pressure, and the residue was purified by SiO2 column chromatography (dichloromethane:methanol=20:1, 2% triethylamine) to afford compound 13a (780 mg, yield 77%) as a yellow solid. MS m/z 209.3 [M+H]+.

Methyl acro-ylate (310 mg, 3.60 mmol) and triethylamine (730 mg, 7.20 mmol) were added to a solution of compound 13a (500 mg, 2.40 mmol) in ethanol under N2 atmosphere. The reaction mixture was stirred at 50° C. overnight. The reaction was monitored by TLC for completion. It was concentrated under reduced pressure, and the residue was purified by SiO2 column chromatography (dichloromethane:methanol=10:1) to afford compound 14a (730 mg, yield 100%) as a yellow solid. MS m/z 295.4 [M+H]+.

Compound 14a (620 mg, 2.11 mmol) was dissolved in a mixture of methanol and water (20 mL/3 mL) followed by the addition of lithium hydroxide monohydrate (884 mg, 21.07 mmol). The reaction mixture was stirred at 60° C. for 1 hour. The reaction was monitored by TLC for completion. After cooling to room temperature, it was acidified with a solution of HCl in methanol (4 M) to pH=3-4, and concentrated under reduced pressure to afford compound 14b (591 mg) as a yellow solid, which was used in next step. MS m/z 281.3 [M+H]+.

Compound 14b (591 mg, 2.11 mmol), o-(tetrahydro-2H-pyran-2-yl)hydroxylamine (297 mg, 2.53 mmol), o-(7-azabenzotriazol-1-yl)-N,N,N',N'-tetramethyluronium hexafluorophosphate (1.20 g, 3.16 mmol), and N,N-diisopropylethylamine (818 mg, 6.33 mmol) were dissolved in N,N-dimethylformamide (7 mL). The reaction mixture was stirred at room temperature for 3 hour. The reaction was monitored by TLC for completion. It was concentrated under reduced pressure, and the residue was purified by SiO2 column chromatography (dichloromethane:methanol=20:1) to afford compound 14c (280 mg, yield of two steps 35%) as a yellow solid. MS m/z 380.3 [M+H]+.

Compound 14c (280 mg, 0.74 mmol) and palladium carbon catalyst (10%, 150 mg) were added to methanol (15 mL) at room temperature. The reaction mixture was stirred under 1 atmospheric pressure of hydrogen at room temperature for 2 hours. The reaction was monitored by TLC for completion. It was filtered through celite, and the filtrate was concentrated under reduce pressure. The residue was purified by SiO2 column chromatography (dichloromethane:methanol=10:1) to afford compound 14d (209 mg, yield 81%) as a brown solid. MS m/z 350.5 [M+H]+.

Compound 14d (209 mg, 0.60 mmol), 1d (212 mg, 0.66 mmol), cesium carbonate (390 mg, 1.20 mmol), Pd2(dba)3 (55 mg, 0.06 mmol), and xantphos (35 mg, 0.06 mmol) were dissolved in 1,4-dioxane (5 mL) under nitrogen atmosphere. The reaction mixture was stirred at 110° C. for 3 hours. The reaction was monitored by TLC for completion. After cooling to room temperature, it was filtered through celite and the filtrate was concentrated under reduced pressure. The residue was purified by SiO2 column chromatography (dichloromethane:methanol=10:1) to afford compound 14e (134 mg, yield 35%) as a yellow solid. MS m/z 636.8 [M+H]+.

A solution of HCl in 1,4-dioxane (4.0 M, 40 drops) was added to a solution of compound 14e (134 mg, 0.21 mmol) in dichloromethane (5 mL). The reaction mixture was stirred at room temperature for 2 hours. The reaction was monitored by TLC for completion. It was filtered and the solid was washed with Et2O to afford compound 14 (95 mg, yield 77%) as a yellow solid. 1H NMR (500 MHz, CD3OD) δ 8.87 (d, J=3.2 Hz, 1H), 8.59 (s, 1H), 8.29 (dd, J=9.7, 2.8 Hz, 1H), 8.19 (d, J=11.1 Hz, 1H), 7.96 (d, J=2.8 Hz, 1H), 7.60 (d, J=9.6 Hz, 1H), 5.20-5.11 (m, 1H), 3.98-3.90 (m, 2H), 3.80-3.72 (m, 2H), 3.57 (t, J=7.0 Hz, 2H), 3.41-3.31 (m, 4H), 3.03-2.92 (m, 1H), 2.99 (s, 3H), 2.75 (t, J=7.0 Hz, 1H), 1.82 (d, J=6.9 Hz, 6H). MS m/z 552.6 [M+H]+.

Example 15. Preparation of 1-(6-((5-fluoro-4-(4-fluoro-1-isopropyl-2-methyl-1H-benzo[d]imidazol-6-yl)pyrimidin-2-yl)amino)pyridin-3-yl)-N-hydroxypiperidine-4-carboxamide hydrochloride salt (compound 15)

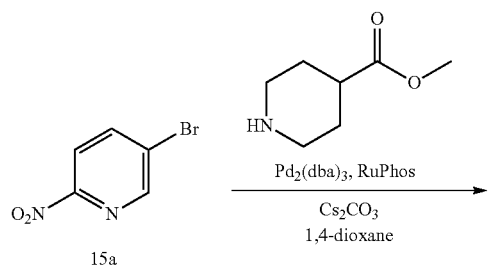

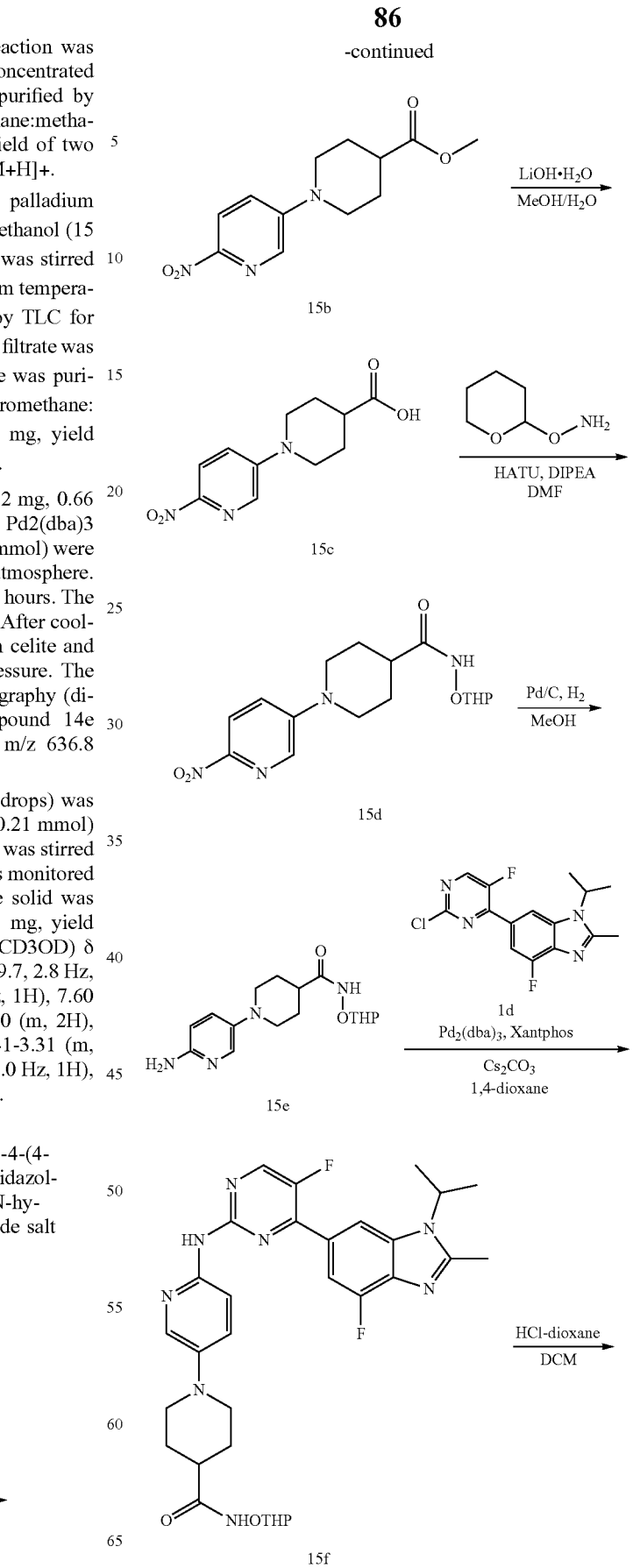

-continued

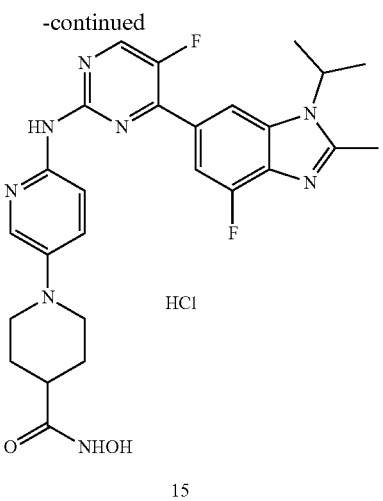

15

5-Bromo-2-nitropyridine 15a (1.5 g, 7.39 mmol), methyl piperidine-4-carboxylate (1.27 g, 8.87 mmol), cesium carbonate (4.82 g, 14.78 mmol), Pd2(dba)3 (338 mg, 0.37 mmol), and RuPhos (345 mg, 0.74 mmol) were dissolved in 1,4-dioxane (30 mL). The reaction mixture was stirred at 110° C. for 3 hours. The reaction was monitored by TLC for completion. After cooling to room temperature, it was filtered through celite and the filtrate was concentrated under reduced pressure. The residue was purified by SiO2 column chromatography (petroleum ether:ethyl acetate=2:1) to afford compound 15b (1.57 g, yield 80%) as a yellow solid. MS m/z 266.4 [M+H]+.

Compound 15b (1.0 g, 3.77 mmol) was dissolved in a mixture of methanol (30 mL) and water (8 mL) followed by the addition of lithium hydroxide monohydrate (1.58 g, 37.70 mmol). The reaction mixture was stirred at 60° C. for 2 hours. The reaction was monitored by TLC for completion. After cooling to room temperature, it was acidified with a solution of HCl in methanol (4 M) to pH=3-4, and concentrated under reduced pressure. The residue was purified by SiO2 column chromatography (dichloromethane:methanol=20:1) to afford compound 15c (920 mg, yield 97%) as a yellow solid. MS m/z 252.3 [M+H]+.

Compound 15c (400 mg, 1.59 mmol), o-(tetrahydro-2H-pyran-2-yl)hydroxylamine (224 mg, 1.91 mmol), o-(7-azabenzotriazol-1-yl)-N,N,N',N'-tetramethyluronium hexafluorophosphate (906 mg, 2.38 mmol), and N,N-diisopropylethylamine (617 mg, 4.78 mmol) were dissolved in N,N-dimethylformamide (5 mL). The reaction mixture was stirred at room temperature for 3 hours. The reaction was monitored by TLC for completion. It was concentrated under reduced pressure and the residue was purified by SiO2 column chromatography (dichloromethane:methanol=20:1) to afford compound 15d (676 mg) as a yellow solid, which was used in next step. MS m/z 351.4 [M+H]+.

Compound 15d (620 mg, 1.77 mmol) and palladium carbon catalyst (10%, 200 mg) were added to methanol (20 mL) at room temperature. The reaction mixture was stirred under 1 atmospheric pressure of hydrogen at room temperature for 1 hour. The reaction was monitored by TLC for completion. It was filtered through celite, and the filtrate was concentrated under reduce pressure. The residue was purified by SiO2 column chromatography (dichloromethane:methanol=10:1) to afford compound 15e (363 mg, yield of two steps 71%) as a brown oil. MS m/z 321.5 [M+H]+.

Compound 15e (363 mg, 1.13 mmol), 1d (402 mg, 1.25 mmol), cesium carbonate (738 mg, 2.27 mmol), Pd2(dba)3 (103 mg, 0.11 mmol), and xantphos (65 mg, 0.11 mmol) were dissolved in 1,4-dioxane (6 mL) under nitrogen atmosphere. The reaction mixture was stirred at 110° C. for 3 hours. The reaction was monitored by TLC for completion. After cooling to room temperature, it was filtered through celite, and the filtrate was concentrated under reduce pressure. The residue was purified by SiO2 column chromatography (dichloromethane:methanol=5:1) to afford compound 15f (112 mg, yield 16%) as a yellow solid. MS m/z 607.7 [M+H]$^+$.

Compound 15f (112 mg, 0.18 mmol) was dissolved in dichloromethane (10 mL) followed by the addition of a solution of HCl in 1,4-dioxane (4.0 M, 40 drops). The reaction mixture was stirred at room temperature for 2 hours. The reaction was monitored by TLC for completion. It was filtered and the solid was washed with Et2O to afford compound 15 hydrochloride salt (96 mg, yield 93%) as a yellow solid. $^1$H NMR (500 MHz, DMSO-d6) δ 11.79 (s, 1H), 10.58 (s, 1H), 8.89 (d, J=3.2 Hz, 1H), 8.37 (s, 1H), 8.25 (dd, J=9.6, 2.8 Hz, 1H), 8.01 (s, 1H), 7.92-7.79 (m, 2H), 5.01-4.91 (m, 1H), 3.73 (d, J=12.3 Hz, 2H), 3.05-2.85 (d, J=43.7 Hz, 2H), 2.82 (s, 3H), 2.33-2.25 (m, 1H), 1.87-1.71 (m, 4H), 1.66 (d, J=6.9 Hz, 6H). MS m/z 523.6 [M+H]+.

Example 16. Preparation of 6'-((5-fluoro-4-(4-fluoro-1-isopropyl-2-methyl-1H-benzo[d]imidazol-6-yl)pyrimidin-2-yl)amino)-N-hydroxy-[2,3'-bipyridine]-5-carboxamide hydrochloride salt (Compound 16)

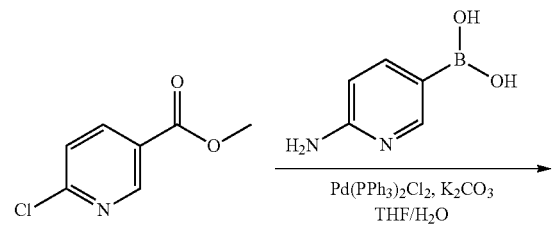

16a

-continued
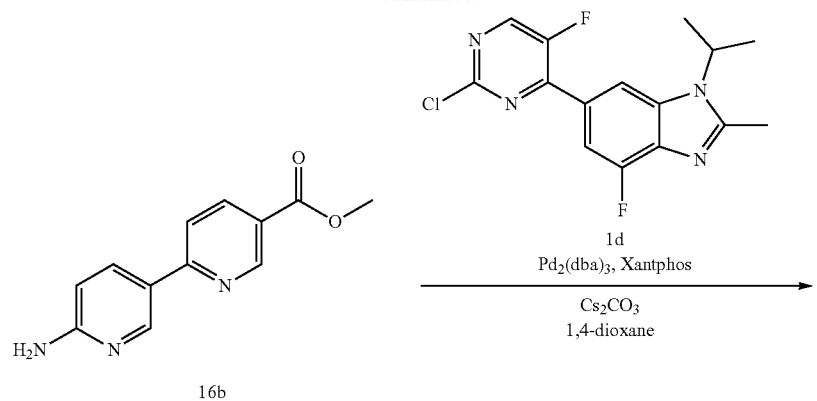
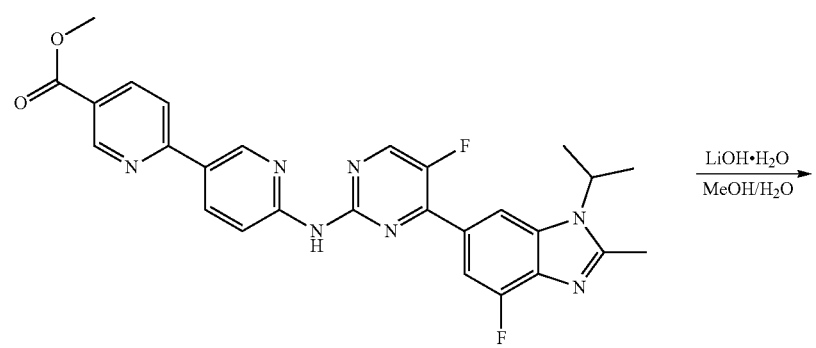
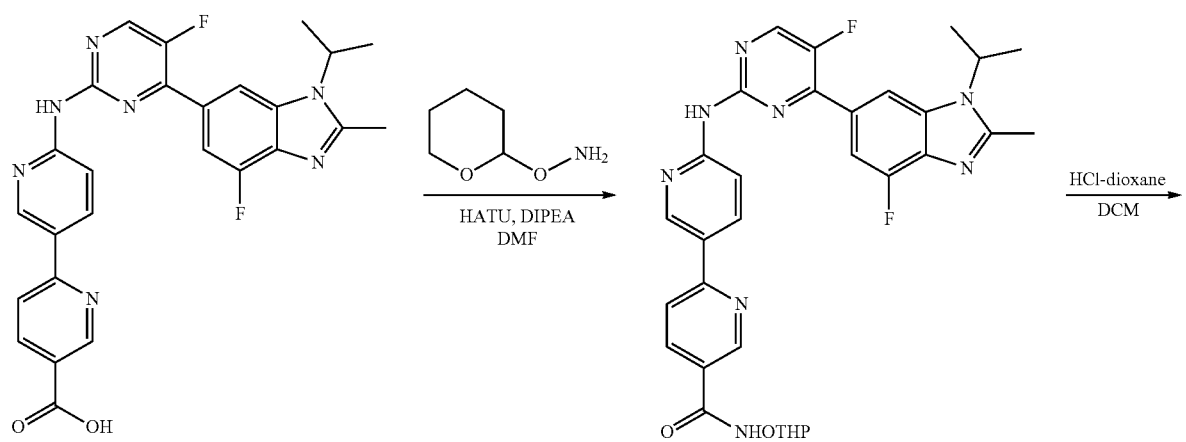

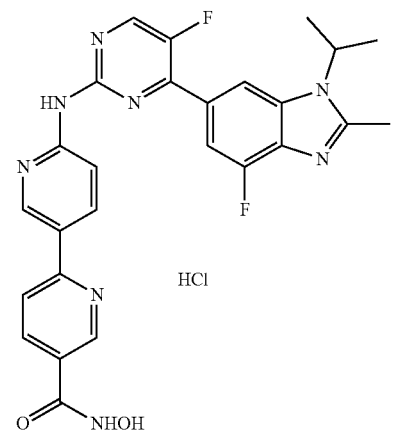

16

Methyl 6-chloropyridine-3-carboxylate 16a (1.0 g, 5.83 mmol), 6-aminopyridine-3-boronicacid (965 mg, 6.99 mmol), potassium carbonate (1.61 g, 11.66 mmol) and Pd(PPh3)2Cl2 (205 mg, 0.29 mmol) were dissolved in a mixture of tetrahydrofuran (16 mL) and water (4 mL) under nitrogen atmosphere. The reaction mixture was stirred at 70° C. for 3 hours. The reaction was monitored by TLC for completion. After cooling to room temperature, it was filtered through celite, and the filtrate was concentrated under reduce pressure. The residue was purified by SiO2 column chromatography (dichloromethane:methanol=15:1) to afford compound 16b (1.2 g, yield 90%) as a light yellow solid. MS m/z 230.4 [M+H]+.

Compound 16b (400 mg, 1.74 mmol), 1d (619 mg, 1.92 mmol), cesium carbonate (1.14 g, 3.49 mmol), Pd2(dba)3 (159 mg, 0.17 mmol), and xantphos (101 mg, 0.17 mmol) were dissolved in 1,4-dioxane (15 mL) under nitrogen atmosphere. The reaction mixture was stirred at 110° C. for 3 hours. The reaction was monitored by TLC for completion. After cooling to room temperature, it was filtered through celite, and the filtrate was concentrated under reduce pressure. The residue was purified by SiO2 column chromatography (dichloromethane:methanol=20:1) to afford compound 16c (324 mg, yield 36%) as a yellow solid. MS m/z 516.5 [M+H]+.

Compound 16c (324 mg, 0.63 mmol) was dissolved in a mixture of methanol (12 mL) and water (12 mL) followed by the addition of lithium hydroxide monohydrate (264 mg, 6.28 mmol). The reaction mixture was stirred at 60° C. for 1 hour. The reaction was monitored by TLC for completion. After cooling to room temperature, it was acidified with a solution of HCl in methanol (4 M) to pH=3-4, and concentrated under reduced pressure to afford compound 16d (320 mg) as a yellow solid, which was used in next step. MS m/z 502.5 [M+H]+.

Compound 16d (320 mg, 0.64 mmol), o-(tetrahydro-2H-pyran-2-yl)hydroxylamine (90 mg, 0.77 mmol), o-(7-azabenzotriazol-1-yl)-N,N,N',N'-tetramethyluronium hexafluorophosphate (364 mg, 0.96 mmol), and N,N-diisopropylethylamine (247 mg, 1.91 mmol) were dissolved in N,N-dimethylformamide (5 mL). The reaction mixture was stirred at room temperature for 2 hours. The reaction was monitored by TLC for completion. It was concentrated under reduce pressure. The residue was purified by SiO2 column chromatography (dichloromethane:methanol=20:1 to 10:1) to afford compound 16e (330 mg, yield of two steps 86%) as a light yellow solid. MS m/z 601.7 [M+H]+.

Compound 16e (320 mg, 0.53 mmol) was dissolved in dichloromethane (6 mL) followed by the addition of a solution of HCl in 1,4-dioxane (4.0 M, 5 mL). The mixture was stirred at room temperature for 1 hour. The reaction was monitored by TLC for completion. It was filtered and the solid was washed with Et2O to afford compound 16 hydrochloride salt (65 mg, yield 22%) as a yellow solid. 1H NMR (500 MHz, DMSO-d6) δ 11.80 (s, 1H), 9.15 (d, J=2.2 Hz, 1H), 9.04 (d, J=1.8 Hz, 1H), 8.93 (d, J=3.2 Hz, 1H), 8.81 (dd, J=9.1, 2.1 Hz, 1H), 8.44 (s, 1H), 8.30 (dd, J=8.3, 2.2 Hz, 1H), 8.18 (dd, J=8.7, 2.6 Hz, 2H), 7.94 (d, J=11.5 Hz, 1H), 5.03-4.94 (m, 1H), 2.85 (s, 3H), 1.69 (d, J=6.9 Hz, 6H). MS m/z 517.6 [M+H]+.

Example 17. Preparation of 3-(6-((5-fluoro-4-(4-fluoro-1-isopropyl-2-methyl-1H-benzo[d]imidazol-6-yl)pyrimidin-2-yl)amino)pyridin-3-yl)-N-hydroxy-propiolamide hydrochloride salt (Compound 17)

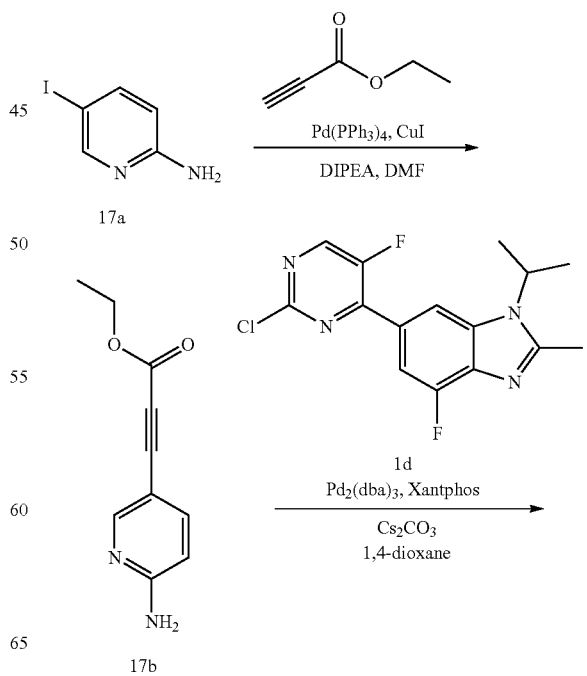

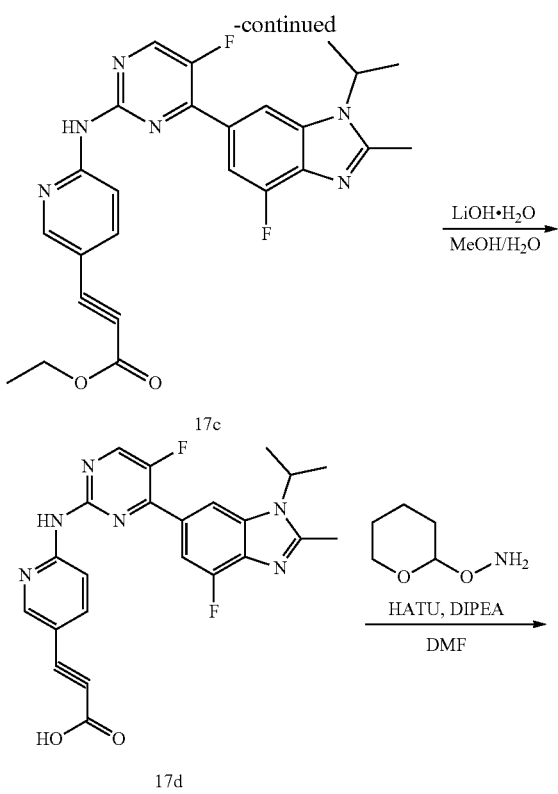

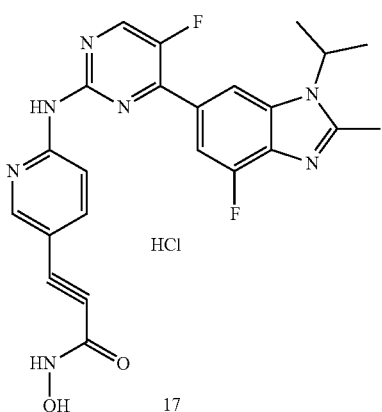

Compound 17a (500 mg, 2.27 mmol), ethyl propiolate (669 mg, 6.82 mmol), Pd(PPh3)4 (262 mg, 0.45 mmol), CuI (43 mg, 0.23 mmol), and DIPEA (2.93 g, 22.7 mmol) were dissolved in DMF (5 mL) under nitrogen atmosphere. The reaction mixture was stirred at 90° C. overnight. The reaction was monitored by TLC for completion. After cooling to room temperature, it was filtered through celite, and the filtrate was concentrated under reduce pressure. The residue was purified by SiO2 column chromatography (dichloromethane:methanol=20:1) to afford compound 17b (128 mg, yield 32%) as a brown solid. MS m/z 191.2 [M+H]+.

Compound 17b (128 mg, 0.73 mmol), 1d (235 mg, 0.73 mmol), cesium carbonate (712 mg, 2.19 mmol), Pd2(dba)3 (64 mg, 0.07 mmol), and xantphos (81 mg, 0.14 mmol) were dissolved in 1,4-dioxane (5 mL) under nitrogen atmosphere. The reaction mixture was stirred at 110° C. for 3 hours. The reaction was monitored by TLC for completion. After cooling to room temperature, it was filtered through celite, and the filtrate was concentrated under reduce pressure. The residue was purified by SiO2 column chromatography (dichloromethane:methanol=10:1) to afford compound 17c (21 mg, yield 6%) as a brown solid. MS m/z 463.2 [M+H]+.

Compound 17c (21 mg, 0.05 mmol) was dissolved in a mixture of methanol (10 mL) and water (1 mL) followed by the addition of lithium hydroxide monohydrate (11 mg, 0.25 mmol). The reaction mixture was stirred at 60° C. for 1 hour. The reaction was monitored by TLC for completion. It was concentrated under reduced pressure to remove methanol. Water (5 mL) was added to the residue, acidified with aqueous HCl (2 M) to pH=4-5, and extracted with ethyl acetate (3×10 mL). The combined organic layers were washed with brine, dried over anhydrous sodium sulfate and filtered. The filtrate was concentrated under reduced pressure to afford compound 17d (17 mg) as a yellow solid, which was used in next step. MS m/z 449.1 [M+H]+.

Compound 17d (17 mg, 0.04 mmol), o-(tetrahydro-2H-pyran-2-yl)hydroxylamine (7 mg, 0.06 mmol), o-(7-azabenzotriazol-1-yl)-N,N,N',N'-tetramethyluronium hexafluoro phosphate (23 mg, 0.06 mmol), and N,N-diisopropylethylamine (15 mg, 0.12 mmol) were dissolved in N,N-dimethylformamide (2 mL). The reaction mixture was stirred at room temperature for 1 hour. The reaction was monitored by TLC for completion. It was poured into ice water, and extracted with dichloromethane (3×10 mL). The combined organic layers were washed with brine, dried over anhydrous sodium sulfate and filtered. The filtrate was concentrated under reduced pressure. The residue was purified by prep-TLC (dichloromethane:methanol=20:1) to afford compound 17e (7 mg, yield 34%) as an off-white solid. MS m/z 548.2 [M+H]+.

Compound 17e (7 mg, 0.01 mmol) was dissolved in tetrahydrofuran (1 mL) followed by the addition of a solution of HCl in 1,4-dioxane (4.0 M, 5 drops). The reaction mixture was stirred at room temperature for 2 hours. The reaction was monitored by TLC for completion. It was filtered and the solid was washed with acetonitrile to afford compound 17 hydrochloride salt (2 mg, yield 31%) as a brown solid. 1H NMR (500 MHz, CD3OD) δ 8.86 (d, J=3.2 Hz, 1H), 8.63-8.56 (m, 2H), 8.27 (dd, J=9.1, 2.0 Hz, 1H), 8.18 (d, J=11.1 Hz, 1H), 7.81 (d, J=9.2 Hz, 1H), 5.17-5.10 (m, 1H), 2.96 (s, 3H), 1.81 (d, J=6.9 Hz, 6H). MS m/z 464.4 [M+H]+.

Example 18. Preparation of 6-((2-((6-((5-fluoro-4-(4-fluoro-1-isopropyl-2-methyl-1H-benzo[d]imidazol-6-yl)pyrimidin-2-yl)amino)pyridin-3-yl)oxy)ethyl)(methyl)amino)-N-hydroxynicotinamide hydrochloride salt (Compound 18)
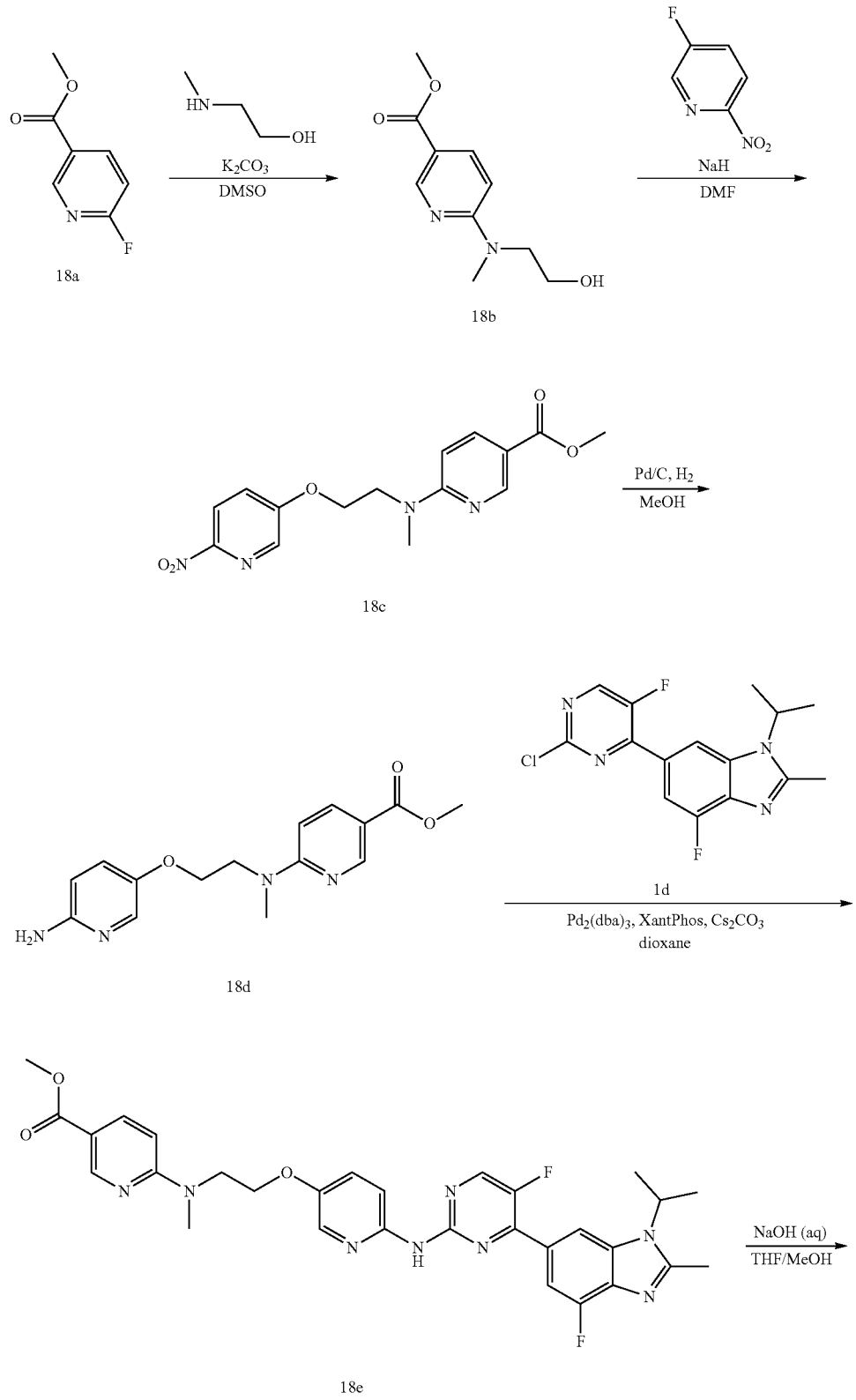

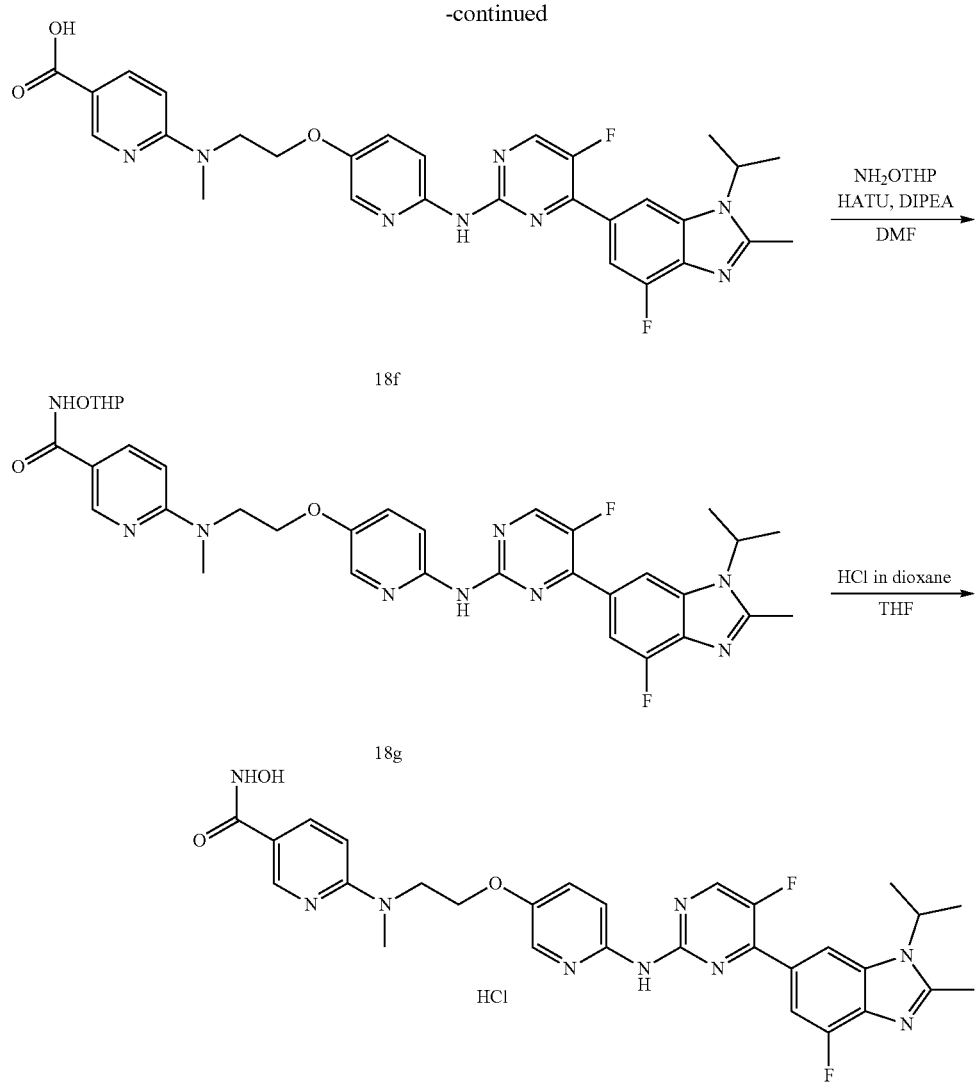

18f

18g

18

Compound 18a (1.0 g, 6.45 mmol) was dissolved in DMSO (15 mL) followed by the addition of N-methyl-2-hydroxyl ethylamine (0.60 mL, 7.74 mmol) and anhydrous potassium carbonate (1.78 g, 12.89 mmol). The reaction mixture was stirred at 120° C. for 18 hours. The reaction was monitored by TLC for completion. After cooling to room temperature, water (30 mL) was added, and extracted with ethyl acetate (3×30 mL). The combined organic layers were washed with brine, dried over anhydrous sodium sulfate, filtered and concentrated under reduced pressure. The residue was purified by SiO2 column chromatography (dichloromethane:ethyl acetate=3:1) to afford compound 18b (1.0 g, yield 74%) as a white solid. 1H NMR (500 MHz, DMSO-d6) δ 8.62 (d, J=2.0 Hz, 1H), 7.91 (dd, J=9.1, 2.4 Hz, 1H), 6.68 (d, J=9.1 Hz, 1H), 4.74 (s, 1H), 3.78 (s, 3H), 3.65 (t, J=5.8 Hz, 2H), 3.58 (t, J=5.8 Hz, 2H), 3.12 (s, 3H).

Compound 18b (450 mg, 2.14 mmol) was dissolved in DMF (8 mL) followed by the addition of 5-fluoro-2-nitro-pyridine (334 mg, 2.35 mmol) and NaH (77 mg, 3.21 mmol, 60%) under ice bath. The reaction mixture was stirred at 0° C. for 1 hour. The reaction was monitored by TLC for completion. Water (10 mL) was added and filtered to afford a solid. It was stirred in ethyl acetate and filtered to afford compound 18c (550 mg, yield 77%) as an off-white solid.

Compound 18c (300 mg, 0.90 mmol) and palladium carbon catalyst (10%, 50 mg) were added to methanol (15 mL) at room temperature. The reaction mixture was stirred under 1 atmospheric pressure of H2 at room temperature for 3 hours. The reaction was monitored by TLC for completion. It was filtered through celite, and the filtrate was concentrated under reduce pressure. The residue was purified by SiO2 column chromatography (dichloromethane:methanol=50:1) to afford compound 18d (260 mg, 95%) as a yellow oil.

Compound 18d (130 mg, 0.43 mmol), 1d (139 mg, 0.43 mmol), cesium carbonate (420 mg, 1.29 mmol), Pd2(dba)3 (12 mg, 0.01 mmol), and xantphos (15 mg, 0.03 mmol) were dissolved in 1,4-dioxane (6 mL) under nitrogen atmosphere. The reaction mixture was stirred at 100° C. overnight. The reaction was monitored by TLC for completion. After cooling to room temperature, it was filtered through celite, and the filtrate was concentrated under reduce pressure. The residue was purified by SiO2 column chromatography (dichloromethane:methanol=100:1 to 50:1) to afford compound 18e (180 mg, yield 71%) as a yellow solid. 1H NMR (500 MHz, CDCl3) δ 8.81 (d, J=2.2 Hz, 1H), 8.41 (d, J=3.7 Hz, 2H), 8.37 (d, J=9.1 Hz, 1H), 8.19 (d, J=1.0 Hz, 1H), 8.05 (dd, J=9.0, 2.3 Hz, 1H), 8.00 (d, J=2.9 Hz, 1H), 7.78 (d, J=11.4 Hz, 1H), 7.35 (dd, J=9.2, 2.8 Hz, 1H), 6.54 (d, J=9.0 Hz, 1H), 4.78-4.68 (m, 1H), 4.26 (t, J=5.5 Hz, 2H), 4.10 (t, J=5.4 Hz, 2H), 3.87 (s, 3H), 3.25 (s, 3H), 2.70 (s, 3H), 1.70 (d, J=7.0 Hz, 6H). MS m/z 589.6 [M+H]+.

Compound 18e (175 mg, 0.30 mmol) was dissolved in a mixture of THF (10 mL), water (2 mL), and methanol (2 mL) followed by the addition of NaOH (60 mg, 1.49 mmol). The reaction mixture was stirred at 60° C. for 4 hours. The reaction was monitored by TLC for completion. It was concentrated under reduced pressure, acidified with aqueous HCl (2 M) to pH=5-6, and extracted with a mixture of dichloromethane and methanol (v:v=10:1, 3×20 mL). The combined organic layers were washed with brine, dried over anhydrous sodium sulfate, filtered and concentrated under reduced pressure to afford compound 18f (130 mg) as a yellow solid, which was used in next step. MS m/z 575.5 [M+H]+.

Compound 18f (130 mg, 0.23 mmol), o-(tetrahydro-2H-pyran-2-yl)hydroxylamine (32 mg, 0.27 mmol), o-(7-azabenzotriazol-1-yl)-N,N,N',N'-tetramethyluronium hexafluorophosphate (129 mg, 0.34 mmol), and N,N-diisopropylethylamine (59 mg, 0.45 mmol) were dissolved in N,N-dimethylformamide (5 mL). The reaction mixture was stirred at 50° C. overnight. The reaction was monitored by TLC for completion. It was poured into ice water, and extracted with a mixture of dichloromethane and methanol (v:v=10:1, 3×20 mL). The combined organic layers were washed with brine, dried over anhydrous sodium sulfate, filtered and concentrated under reduced pressure. The residue product was purified by SiO2 column chromatography (dichloromethane:methanol=50:1) and preparative TLC to afford compound 18 g (100 mg, yield 66%) as a yellow solid. 1H NMR (500 MHz, CDCl3) δ 9.02 (s, 1H), 8.61 (d, J=2.1 Hz, 1H), 8.52 (s, 1H), 8.41 (d, J=3.7 Hz, 1H), 8.36 (d, J=9.1 Hz, 1H), 8.17 (d, J=1.1 Hz, 1H), 8.11 (s, 1H), 7.91 (dd, J=9.0, 2.3 Hz, 1H), 7.77 (d, J=11.6 Hz, 1H), 7.32 (dd, J=9.1, 2.9 Hz, 1H), 6.54 (d, J=9.0 Hz, 1H), 5.08 (s, 1H), 4.73 (m, 1H), 4.23 (t, J=5.6 Hz, 2H), 4.08-4.00 (m, 3H), 3.65 (m, 1H), 3.21 (s, 3H), 2.69 (s, 3H), 1.87 (m, 3H), 1.69 (d, J=7.0 Hz, 6H), 1.66-1.54 (m, 3H). MS m/z 674.7 [M+H]+.

Compound 18g (100 mg, 0.15 mmol) was dissolved in THF (5 mL) followed by the addition of a solution of HCl in 1,4-dioxane (4.0 M, 10 drops). The reaction mixture was stirred at room temperature for 2 hours, and monitored by TLC. It was filtered and the solid was washed with acetonitrile to afford compound 18 hydrochloride salt (90 mg, yield 88%) as a yellow solid. 1H NMR (500 MHz, CD3OD) δ 8.87 (d, J=3.2 Hz, 1H), 8.58 (d, J=0.8 Hz, 1H), 8.38 (s, 1H), 8.32 (d, J=9.7 Hz, 1H), 8.19 (d, J=11.3 Hz, 1H), 8.12-8.06 (m, 2H), 7.58 (d, J=9.4 Hz, 1H), 7.54 (d, J=9.2 Hz, 1H), 5.21-5.13 (m, 1H), 4.50 (t, J=4.9 Hz, 2H), 4.25 (t, J=4.8 Hz, 2H), 3.46 (s, 3H), 2.98 (s, 3H), 1.81 (d, J=6.9 Hz, 6H). MS m/z 590.7 [M+H]+.

Example 19. Preparation of 2-((2-((6-((5-fluoro-4-(4-fluoro-1-isopropyl-2-methyl-1H-benzo[d]imidazol-6-yl)pyrimidin-2-yl)amino)pyridin-3-yl)oxy)ethyl)(methyl)amino)-N-hydroxypyrimidine-5-carboxamide (Compound 19)

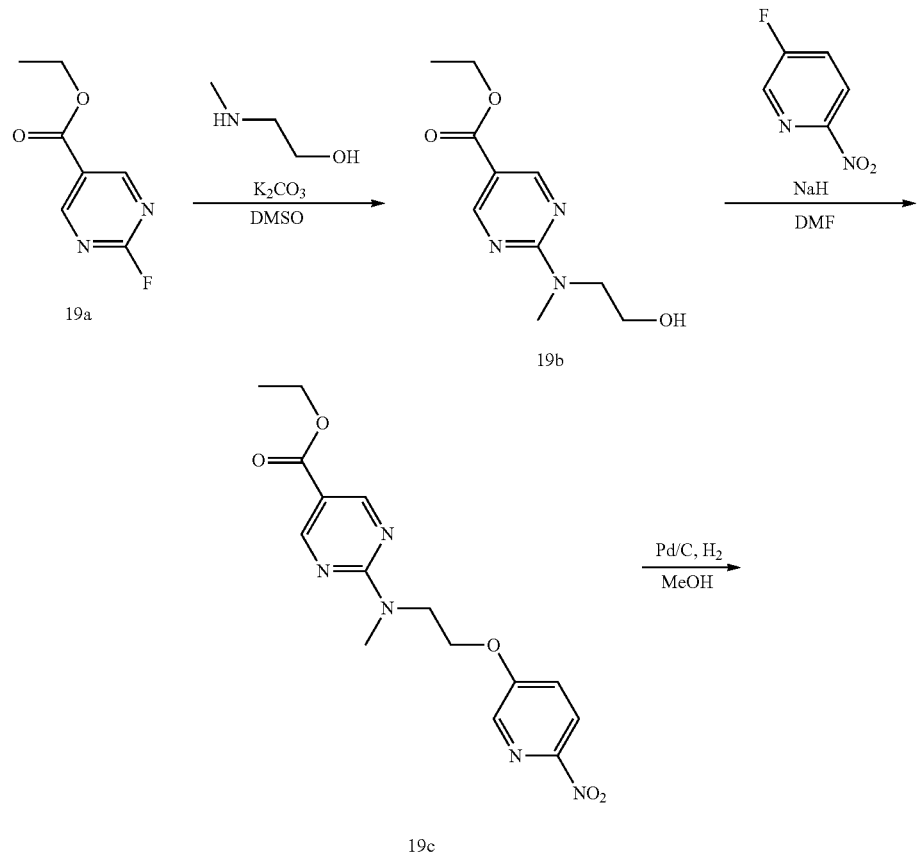

-continued
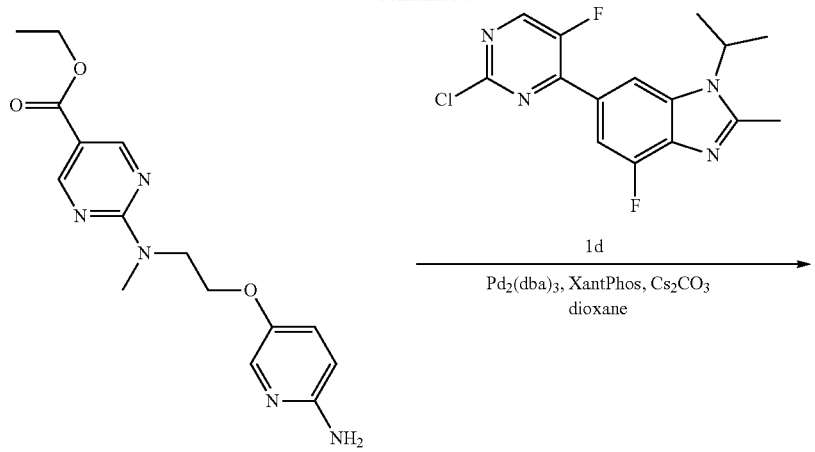
19d
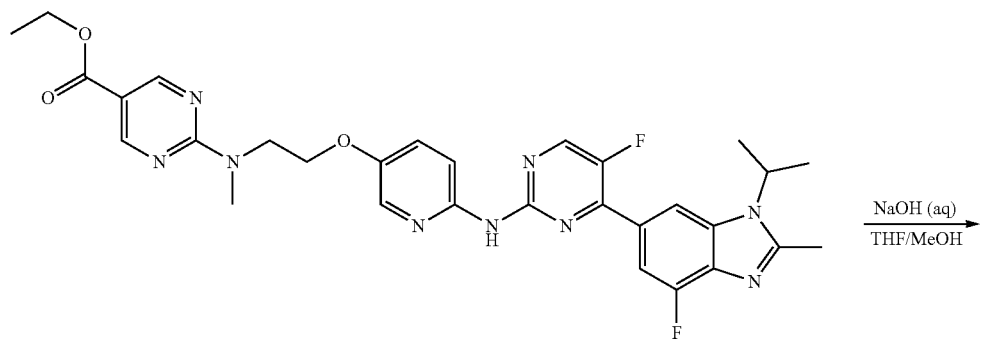
19e
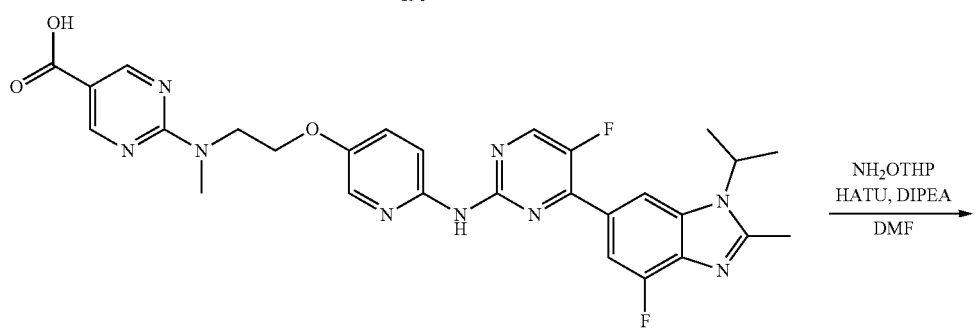
19f
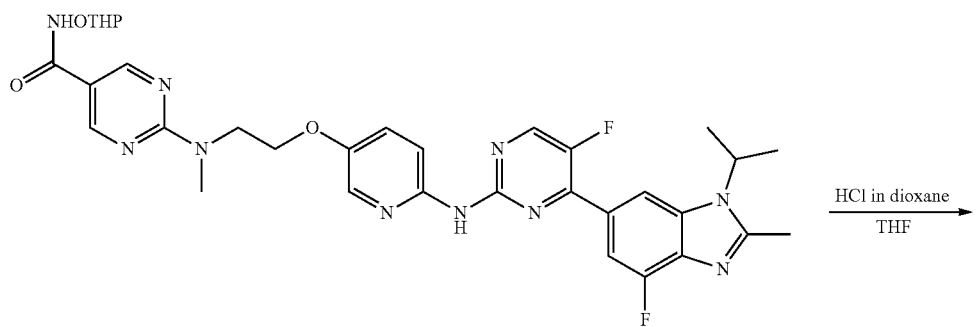
19g

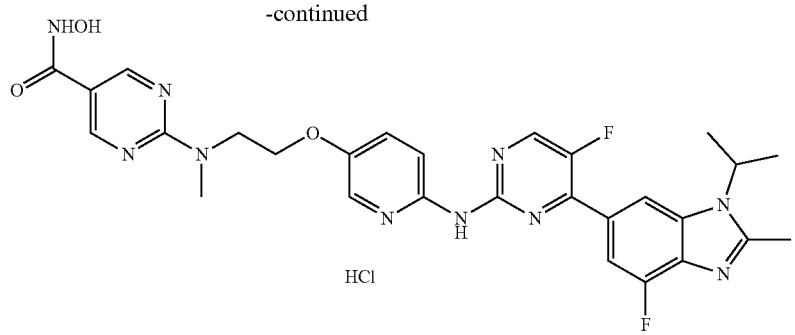

19

Compound 19a (1.0 g, 5.88 mmol), N-(2-methoxyethyl)methylamine (662 mg, 8.82 mmol), and potassium carbonate (1.62 g, 11.75 mmol) were dissolved in DMSO (10 mL). The reaction mixture was stirred at 120° C. for 18 hours. The reaction was monitored by TCL. Water (30 mL) was added and extracted with ethyl acetate (3×30 mL). The combined organic layers were washed with brine, dried over anhydrous sodium sulfate, filtered and concentrated under reduced pressure. The residue product was purified by SiO₂ column chromatography to afford compound 19b (1.0 g, yield 76%) as a white solid.

Compound 19b (1.0 g, 4.44 mmol) and 2-fluoro-5-nitropyridine (757 mg, 5.33 mmol) were dissolved in DMF (10 mL) followed by addition of NaH (266 mg, 6.66 mmol, 60%) under ice bath. Then the reaction mixture was stirred at room temperature until the reaction was completed. Water (10 mL) was added and a light yellow solid was collected via filtration. The solid was stirred in ethyl acetate and filtered to afford compound 19c (0.9 g, yield 58%) as a white solid. MS m/z 293.2 [M+H]+.

Compound 19c (300 mg, 0.86 mmol) and palladium carbon catalyst (10%, 50 mg) were added to methanol (15 mL) at room temperature. The reaction mixture was stirred under 1 atmospheric pressure of H2 at room temperature for 1 hour. The reaction was monitored by TLC for completion. It was filtered through celite, and the filtrate was concentrated under reduced pressure to afford compound 19d (260 mg, yield 96%) as a white solid, which was used in next step. MS m/z 318.3 [M+H]+.

Compound 19d (200 mg, 0.63 mmol), compound 1d (244 mg, 0.76 mmol), cesium carbonate (410 mg, 1.26 mmol), Pd2(dba)3 (57 mg, 0.06 mmol), and xantphos (73 mg, 0.12 mmol) were dissolved in 1,4-dioxane (5 mL) under nitrogen atmosphere. Then the reaction mixture was stirred at 110° C. for 18 hour. The reaction was monitored by TLC for completion. After cooling to room temperature, it was filtered through celite, and the filtrate was concentrated under reduced pressure. The residue was purified by SiO2 column chromatography (dichloromethane:methanol=10:1) to afford 19e (180 mg, yield 47%) as a yellow solid. MS m/z 604.7 [M+H]+.

Compound 19e (232 mg, 0.29 mmol) was dissolved in a mixture of THF (10 mL), water (2 mL) and methanol (2 mL) followed by the addition of NaOH (60 mg, 1.49 mmol). The reaction mixture was stirred at 70° C. for 4 hours. The reaction was monitored by TLC for completion. It was concentrated under reduced pressure, acidified with aqueous HCl (2 M) to pH=5-6, and extracted with a mixture of dichloromethane and methanol (v:v=10:1, 3×20 mL). The combined organic layers were washed with brine, dried over anhydrous sodium sulfate, filtered and concentrated under reduced pressure to afford compound 19f (150 mg, yield 87%) as a yellow solid, which was used in next step. MS m/z 576.5 [M+H]+.

Compound 19f (150 mg, 0.26 mmol), o-(tetrahydro-2H-pyran-2-yl)hydroxylamine (34 mg, 0.29 mmol), o-(7-azabenzotriazol-1-yl)-N,N,N',N'-tetramethyluronium hexafluorophosphate (180 mg, 0.29 mmol), and N,N-diisopropylethylamine (100 mg, 0.78 mmol) were dissolved in N,N-dimethylformamide (5 mL). The reaction mixture was stirred at 50° C. for 1 hour. The reaction was monitored by TLC for completion. It was poured into ice water, and extracted with dichloromethane (3×10 mL). The combined organic layers were washed with brine, dried over anhydrous sodium sulfate, filtered and concentrated under reduced pressure. The residue product was purified by SiO2 column chromatography (dichloromethane:methanol=20:1) to afford compound 19g (100 mg, yield 57%) as a yellow solid. 1H NMR (500 MHz, CDCl3) δ 9.26 (s, 1H), 8.73 (s, 3H), 8.42 (d, J=3.7 Hz, 1H), 8.36 (d, J=9.1 Hz, 1H), 8.17 (d, J=1.1 Hz, 1H), 8.09 (d, J=2.9 Hz, 1H), 7.78 (d, J=11.6 Hz, 1H), 7.33 (dd, J=9.2, 3.0 Hz, 1H), 5.08 (s, 1H), 4.73-4.70 (m, 1H), 4.21 (t, J=5.5 Hz, 2H), 4.06-4.01 (m, 3H), 3.66-3.64 (m, 1H), 3.35 (s, 3H), 2.69 (s, 3H), 1.88-1.83 (m, 3H), 1.68 (d, J=5.0 Hz, 1H), 1.66-1.58 (m, 3H).

Compound 19g (70 mg, 0.10 mmol) was dissolved in THE (2 mL) followed by the addition of a solution of HCl in 1,4-dioxane (4.0 M, 10 drops). The reaction mixture was stirred at room temperature for 2 hours. The reaction was monitored by TLC for completion. It was filtered and the solid was washed with acetonitrile to afford compound 19 hydrochloride salt (60 mg, yield 92%) as a yellow solid. 1H NMR (500 MHz, CD3OD) δ 8.86 (d, J=3.2 Hz, 1H), 8.78 (s, 2H), 8.58 (d, J=0.9 Hz, 1H), 8.19 (d, J=11.0 Hz, 1H), 8.11 (dd, J=9.6, 2.9 Hz, 1H), 8.06 (d, J=2.8 Hz, 1H), 7.57 (d, J=9.6 Hz, 1H), 5.20-5.11 (m, 1H), 4.45 (t, J=5.4 Hz, 2H), 4.23 (t, J=5.4 Hz, 2H), 3.40 (s, 3H), 2.98 (s, 3H), 7.57 (d, J=10.0 Hz, 1H). MS m/z 591.7 [M+H]+.

Example 20: Biology Assays

1. CDK2, CDK4 and CDK6 Kinase Assays:

In vitro enzymatic activity of the CDK isoforms CDK2/CycA2, CDK4/CycD3 and CDK6/cycD3 were measured using Mobility Shift Assay that monitors phosphorylation ratio of FAM labelled peptide (Peptide 18 for CDK2/CycA2, Peptide 8 for CDK4/CycD3). CDK2/CycA2 and CDK6/CycD3 were assayed under buffer conditions in the presence of 50 mM HEPES (pH 7.5), 10 mM MgCl2, 0.0015% Brij-35 and 2 mM dithiothreitol; CDK4/CycD3 with buffer condition of 20 mM HEPES (pH 7.5), 10 mM MgCl2, 0.01% Triton X-100 and 2 mM dithiothreitol. Prepare compounds to 50× of the final desired highest inhibitor concentration by 100% DMSO and serial dilution in 3-fold for total of 10 concentrations. For each isoform, dosage of enzyme and substrate are CDK2/CycA2 12 nM, ATP Km 39 μM; CDK4/CycD3 10 nM, ATP Km 221p M; CDK6/cycD3 15 nM, ATP Km 800 μM. After assay for 60 min, 180 min, 60 min respectively at 28° C., reactions were terminated with stop solution (50 mM EDTA, 0.015% Brij-35, 0.2% Coating Reagent #3 and 100 mM HEPES (pH 7.5)). Collect conversion on Caliper EZ Reader. IC50 values were calculated by fitting the dose-response curves with Xlfit excel add-in version 4.3.1.

The testing results of the representative compounds are listed in Table 1 below. The enzyme inhibitory activity is represented by letters A, B, C, D and E, in which A represents IC50 less than 10 nM, B represents IC50 greater than or equal to 10 nM but less than 100 nM, C represents IC50 greater than or equal to 100 nM but less than 500 nM, D represents IC50 greater than or equal to 500 nM but less than 1000 nM, and E represents IC50 greater than or equal to 1000 nM.

TABLE 1

CDK2, CDK4 and CDK6 assays

| compou | CDK4 (IC$_{50}$, nM) | CDK6 (IC$_{50}$, nM) | CDK2 |
|---|---|---|---|
| 1 | A | B | B |
| 2 | A | B | C |
| 3 | A | B | B |
| 4 | A | C | C |
| 5 | A | C | B |
| 6 | A | B | A |
| 7 | B | D | C |
| 8 | A | B | B |
| 9 | A | B | B |
| 10 | A | A | B |
| 11 | A | B | A |
| 12 | B | E | B |
| 13 | A | A | B |
| 14 | A | B | B |
| 15 | A | B | B |
| 16 | A | B | A |
| 17 | A | | |

2. HDAC-1, HDAC-2 and HDAC-6 Assays:

The inhibitory effect of compounds on HDAC-1 and HDAC-6 function was determined in vitro using an optimized homogenous assay performed in 384-well plate format. In this assay, the recombinant, full-length HDAC-1, HDAC-2 or HDAC-6 protein (BPS Biosciences) was incubated with Ac-peptide-AMC with concentrations in the Km plot. Reactions were performed in Tris-based assay buffer and were followed for fluorogenic release of 7-amino-4-methylcoumarin from substrate upon deacetylase and trypsin enzymatic activity. Fluorescence measurements were obtained using a multilabel plate reader (Synergy MX with excitation at 355 nm and emission at 460 nm). Data were analyzed on a plate-by-plate basis for the linear range of fluorescence over time. Fit the data in GraphPad Prism V5.0 software to obtain IC50 values using equation (Y=Bottom+(Top-Bottom)/(1+10^((Log IC50−X)*Hill Slope), Y is % inhibition and X is compound concentration).

The testing results of the representative compounds are listed in Table 2 below. The enzyme inhibitory activity is presented using letters A, B, C, D and E, in which A represents IC50 less than 10 nM, B represents IC50 greater than or equal to 10 nM but less than 100 nM, C represents IC50 greater than or equal to 100 nM but less than 500 nM, D represents IC50 greater than or equal to 500 nM but less than 1000 nM, and E represents IC50 greater than or equal to 1000 nM.

TABLE 2

HDAC-1 and HDAC-6 assays

| compound | HDAC1 (IC$_{50}$, nM) | HDAC6 (IC$_5$, nM) |
|---|---|---|
| 1 | C | B |
| 2 | A | B |
| 3 | B | B |
| 4 | C | A |
| 5 | E | B |
| 6 | C | B |
| 7 | C | B |
| 8 | B | A |
| 9 | E | A |
| 10 | C | A |
| 11 | E | E |
| 12 | C | B |
| 13 | E | B |
| 14 | E | D |
| 15 | E | C |
| 16 | E | C |

OTHER EMBODIMENTS OF THE INVENTION

The present invention has been described above with reference to specific examples and embodiments, but is not constructed in any way to limit the scope of the present invention. It should be understood that various modifications and additions can be made to the disclosed specific examples and embodiments without departing from the spirit of the present invention, and such modifications and additions are considered part of the present invention.

The invention claimed is:

1. A compound of the following formula (I), or a deuterated derivative, a diastereomers, or an enantiomers thereof:

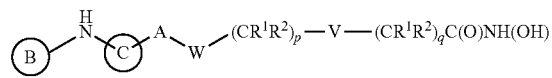

(I)

or a pharmaceutically acceptable salt, prodrug, hydrate, or a solvate thereof, wherein:

Ⓑ is formula (II):

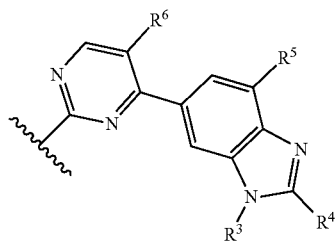

(II)

Ⓒ is phenyl ring, or 5- to 6-membered monocyclic heteroaromatic ring, wherein the mono-heteroaromatic ring comprises 1 to 3 heteroatoms independently selected from N, O and S;
"ww" represents the attaching site of Ⓒ in the formula (I); wherein the
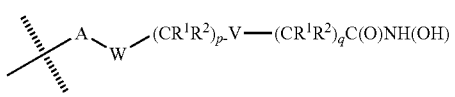
is selected from the following groups:
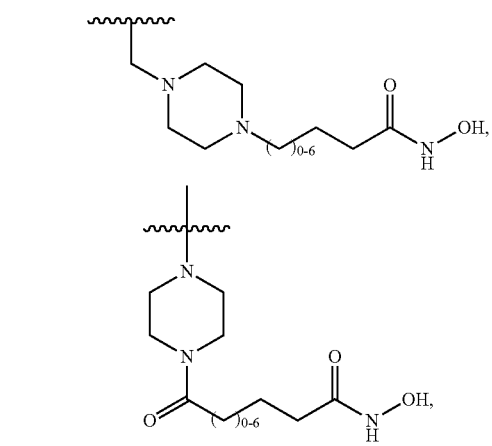
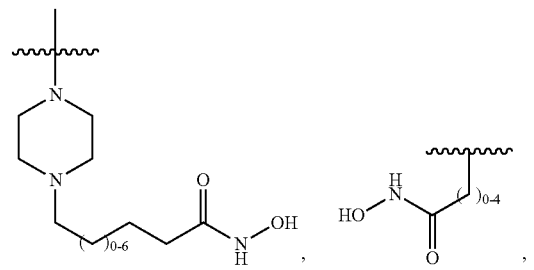
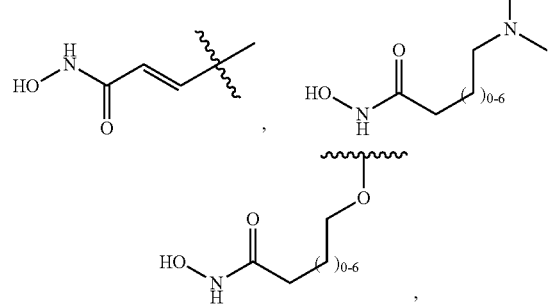
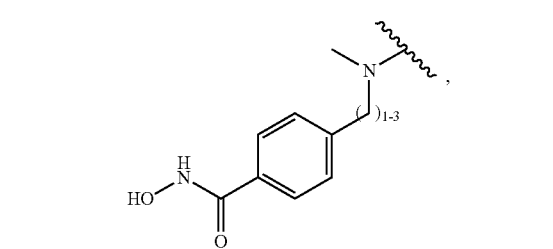
-continued
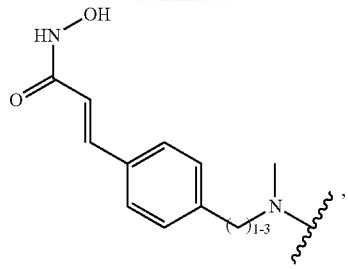
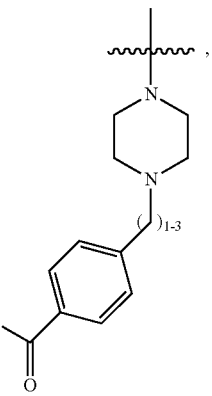
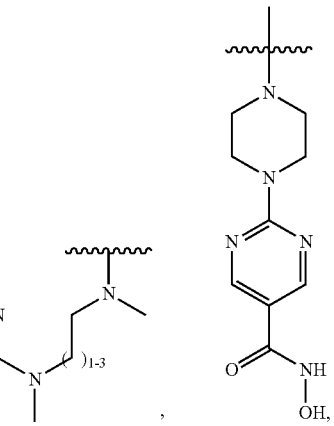
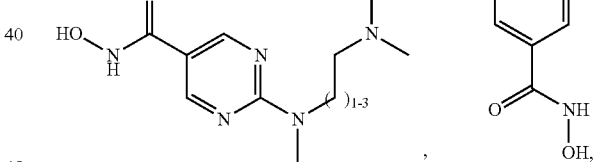
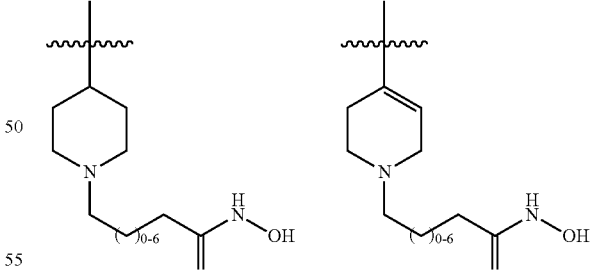
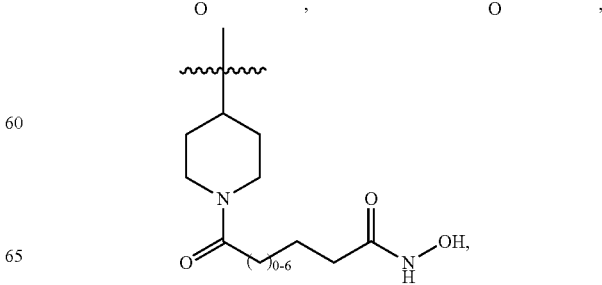

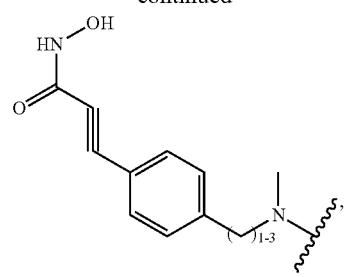
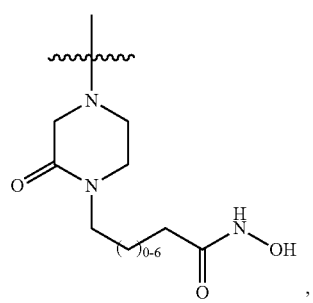
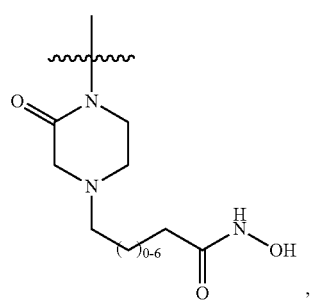
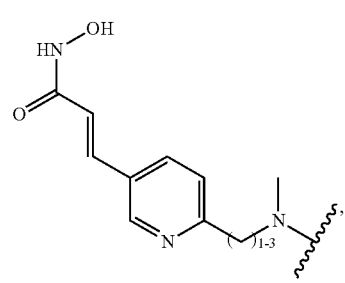
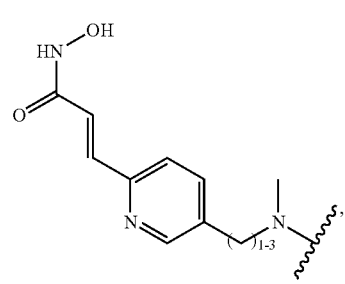
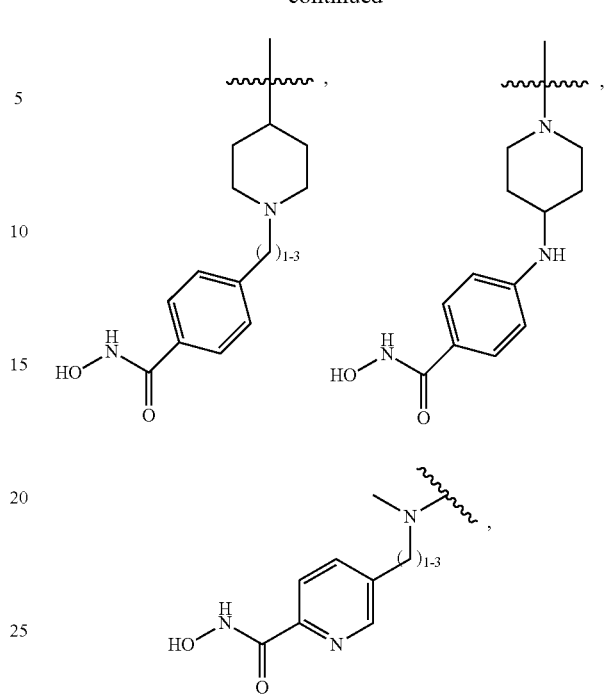
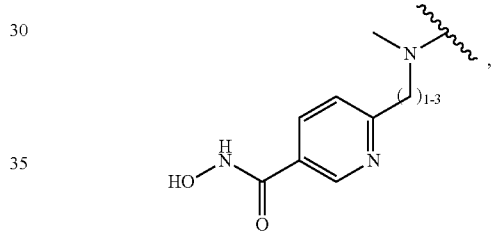
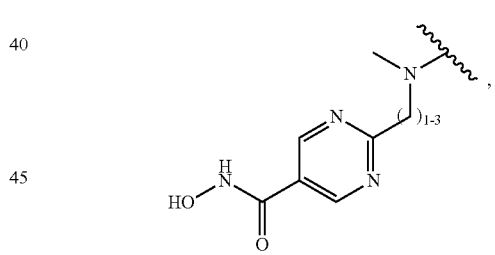
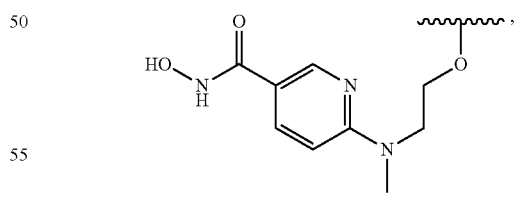
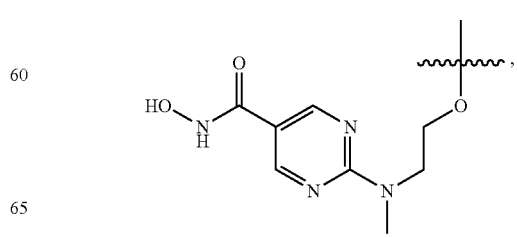

-continued

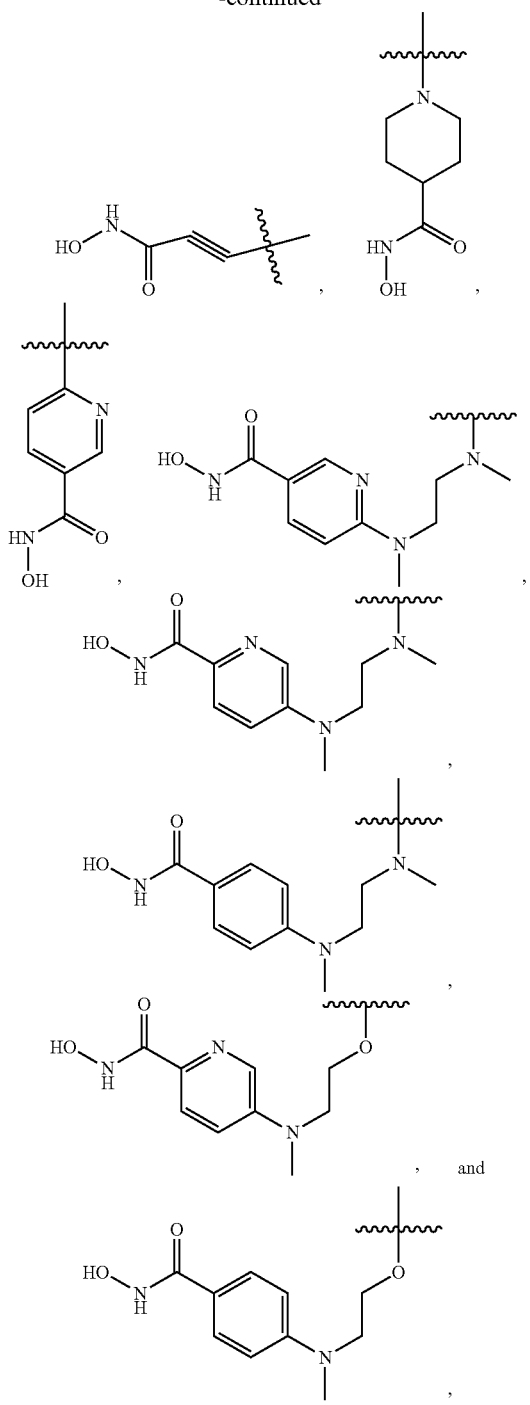

and wherein I is the connecting point to Ⓒ wherein the groups in formula (II) are defined as follows: $R^3$ is $C_{1-8}$ alkyl, $C_{3-8}$ cycloalkyl, or $C_{3-8}$ cycloalkylmethyl; $R^4$ is hydrogen, $C_{1-8}$ alkyl, $C_{2-8}$ alkenyl, $C_{2-8}$ alkynyl, $C_{3-8}$ cycloalkyl; $R^5$ and $R^6$ are each independently hydrogen, halogen, $C_{1-8}$ alkyl, $C_{2-8}$ alkenyl, $C_{2-8}$ alkynyl, or $C_{3-8}$ cycloalkyl; wherein at least one of $R^5$ or $R^6$ is fluorine.

2. The compound of claim 1, wherein in formula (II), $R^3$ is isopropyl, $R^4$ is methyl, $R^5$ is fluorine, and $R^6$ is fluorine.

3. The compound of claim 1, wherein Ⓒ is selected from the group consisting of benzene ring and pyridine ring.

4. A compound selected from the group consisting of:

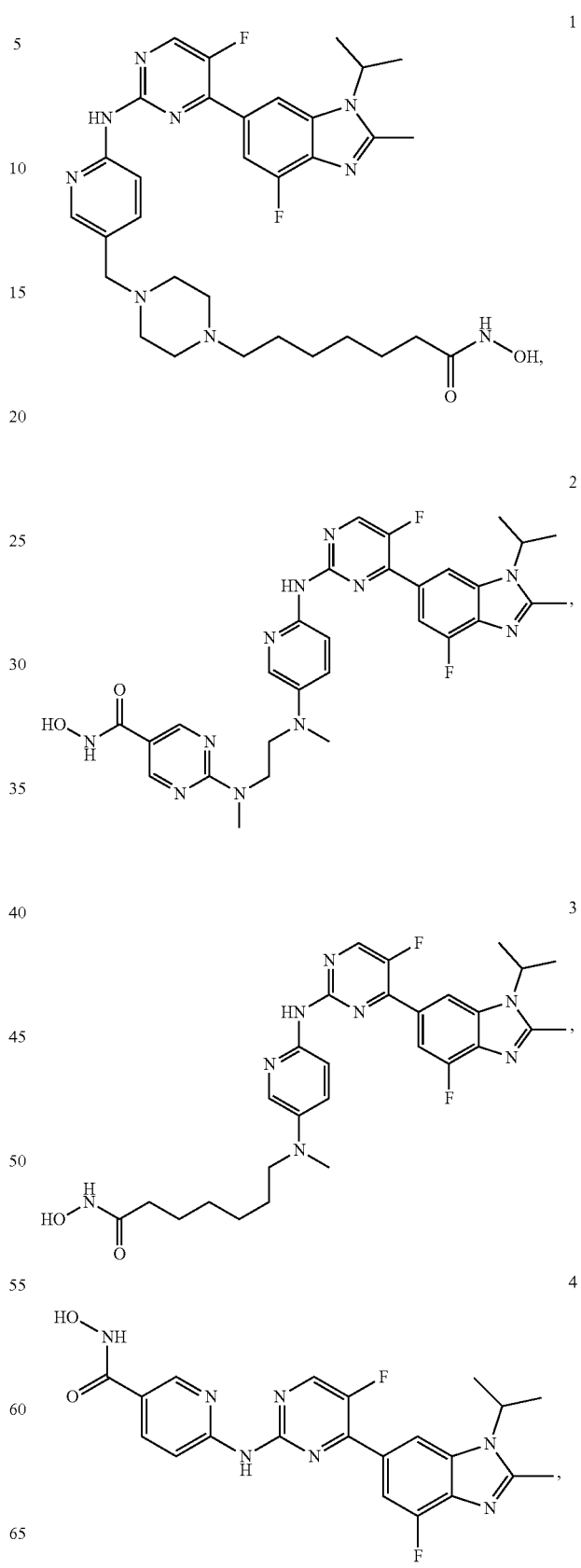

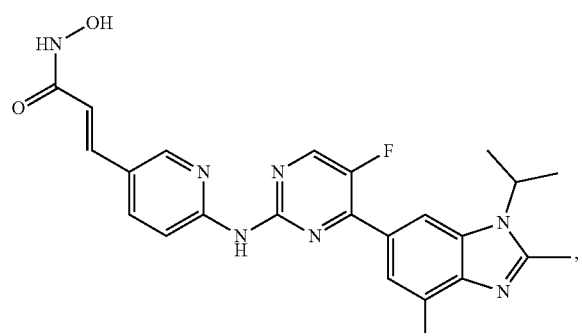
5
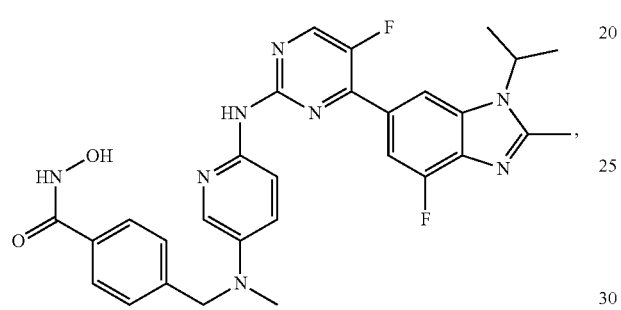
6
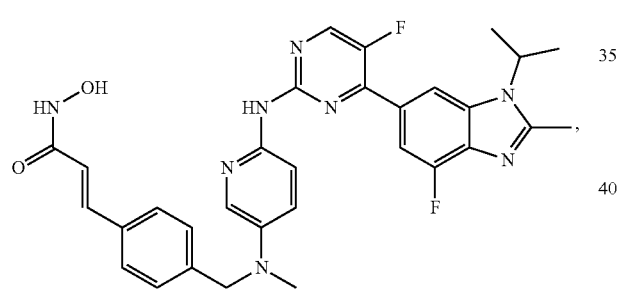
7
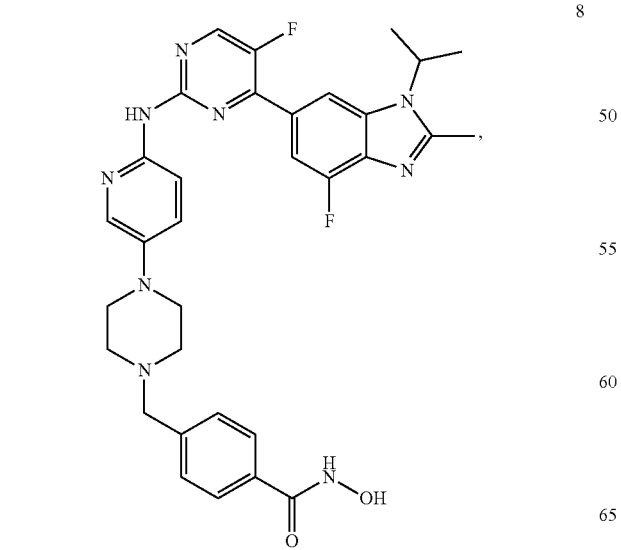
8
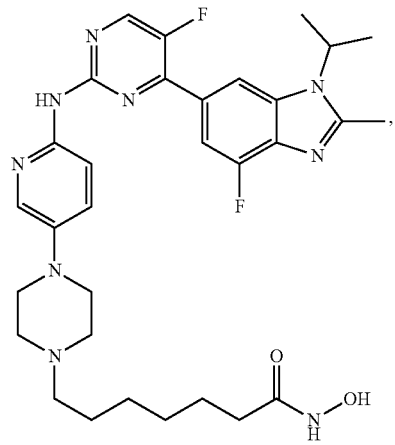
9
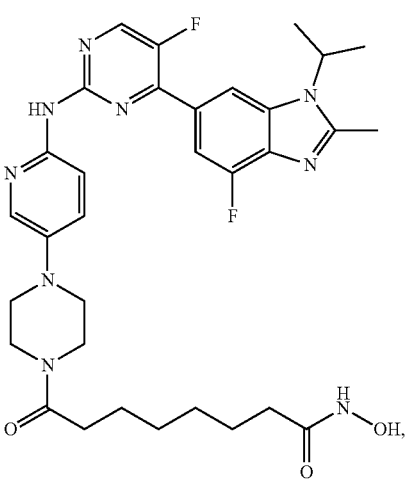
10
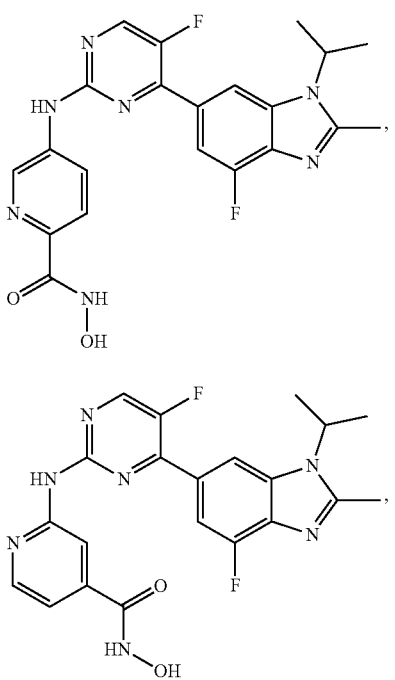
11
12

13
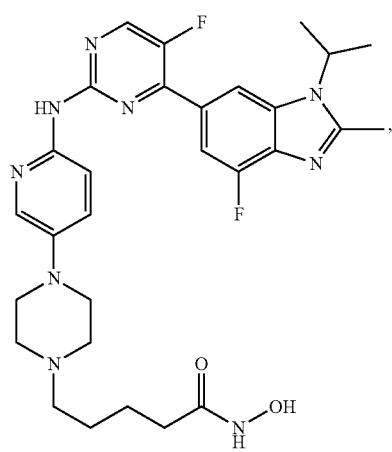
14
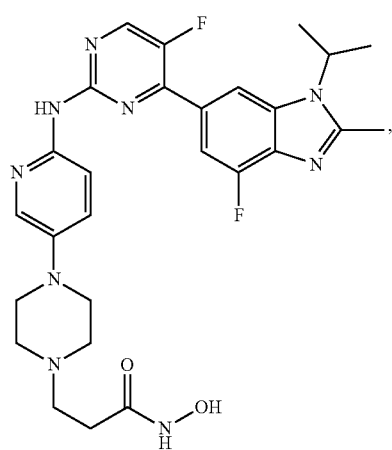
15
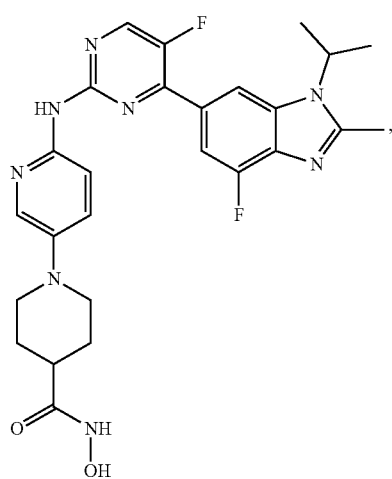
16
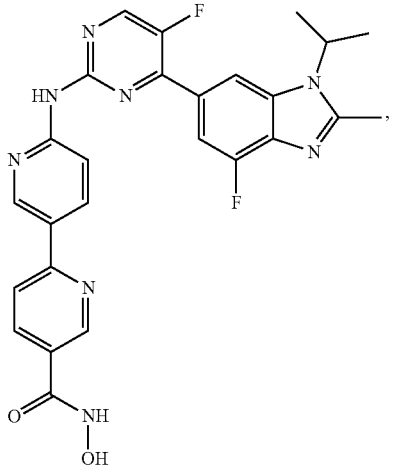
17
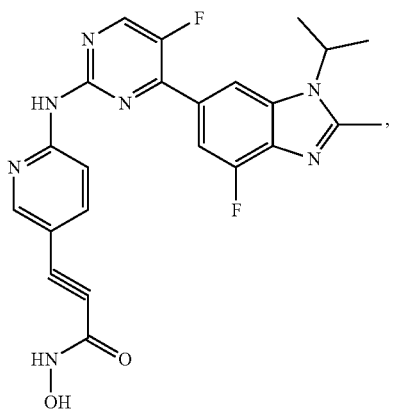
18
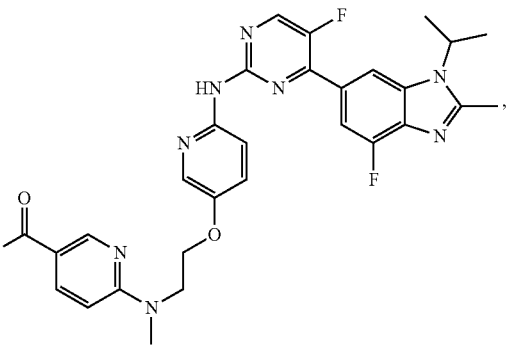

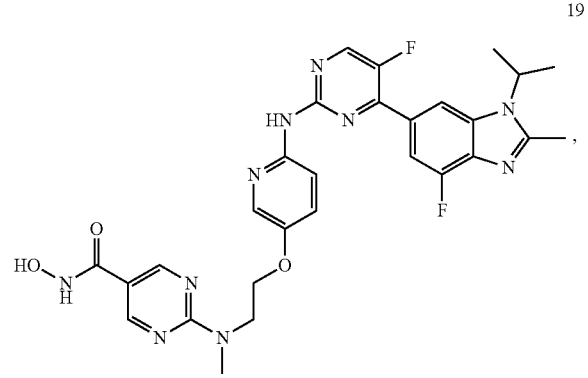
19
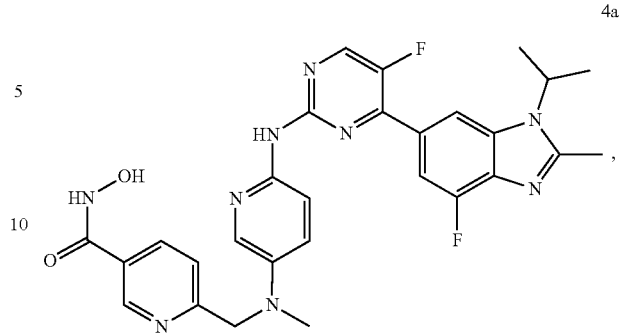
4a
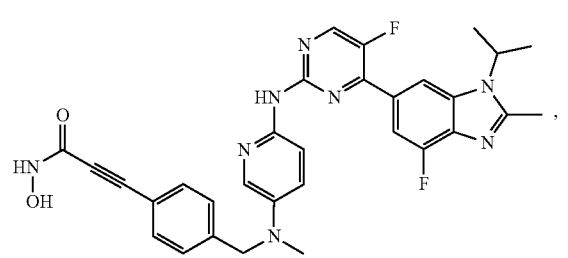
1a
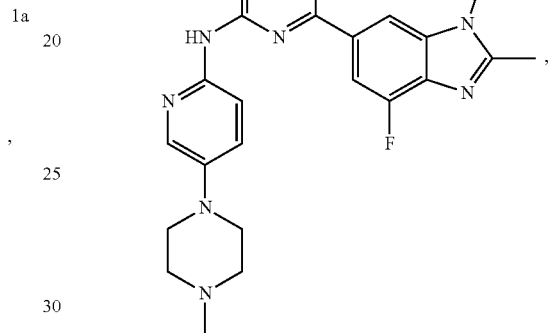
5a
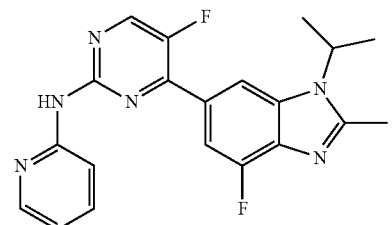
2a
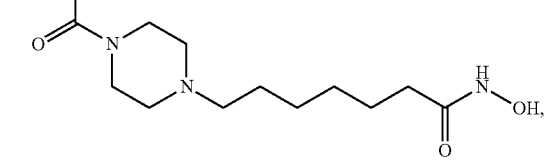
3a
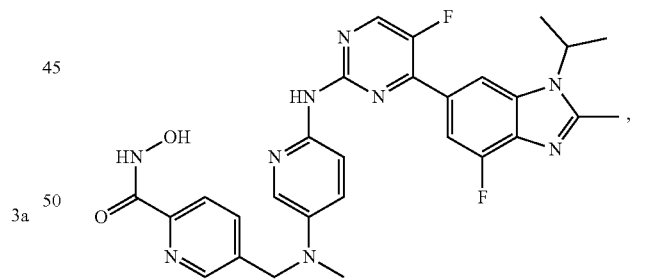
6a
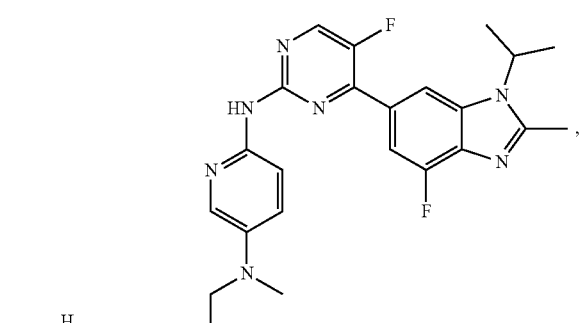
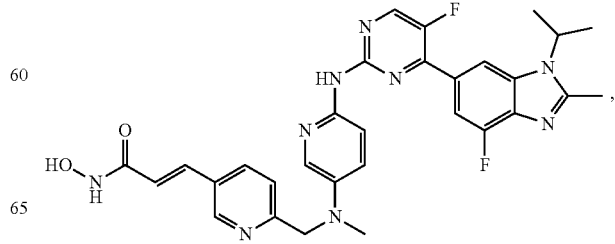
7a -continued
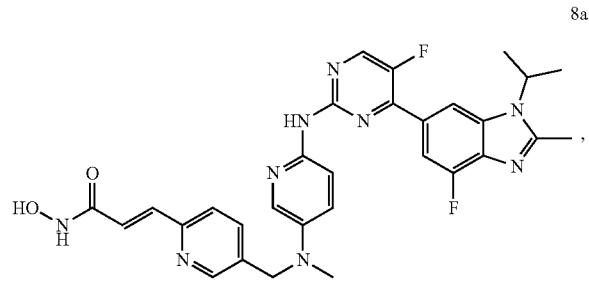
8a
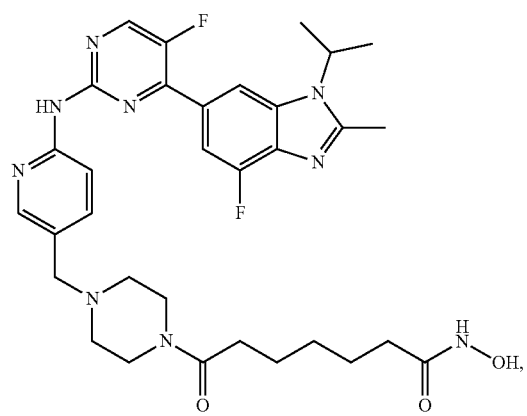
9a
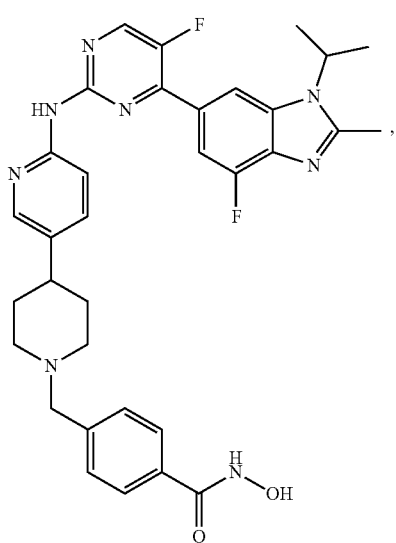
10a
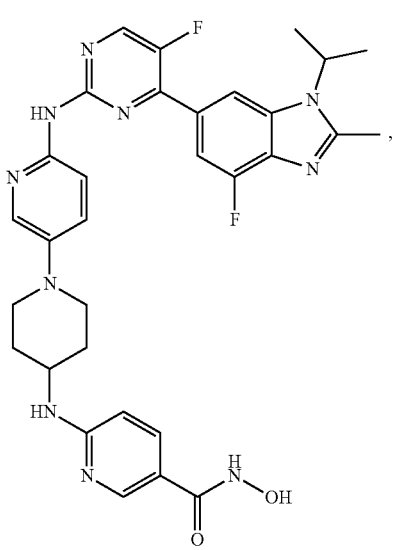
11a
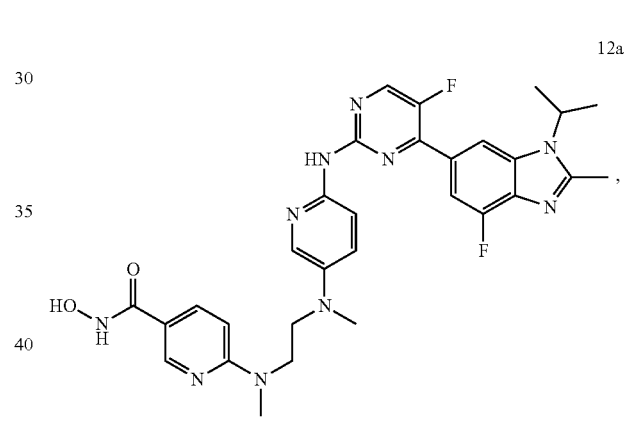
12a
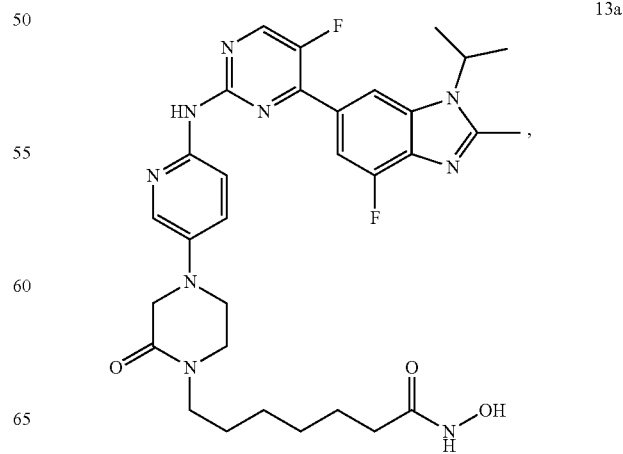
13a 121
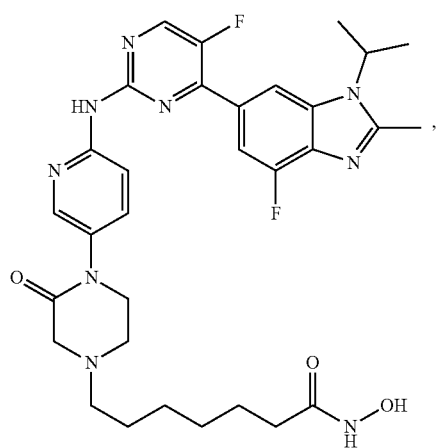
14a
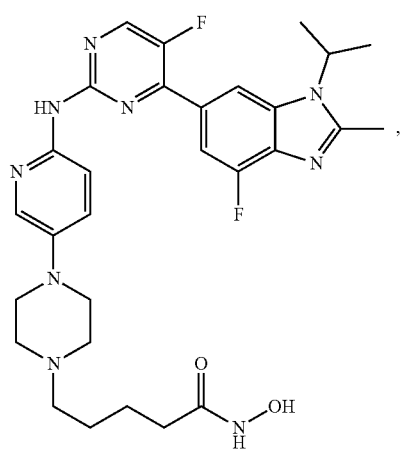
15a
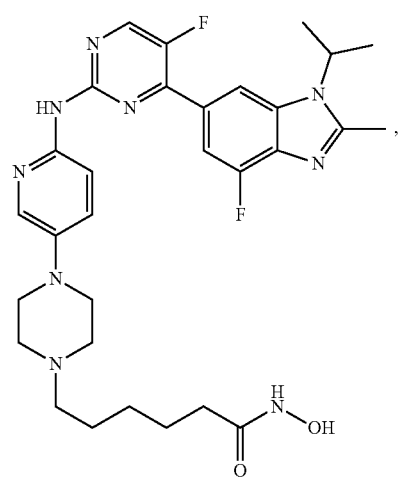
16a
122
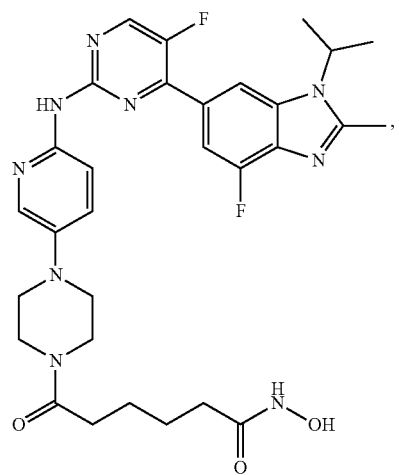
17a
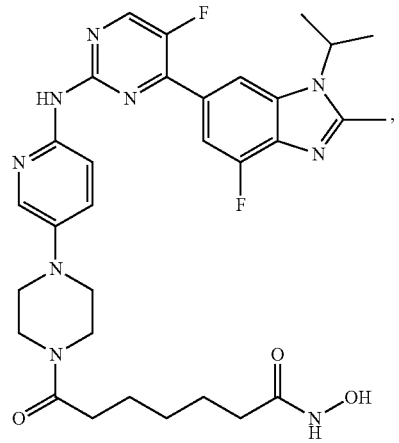
18a
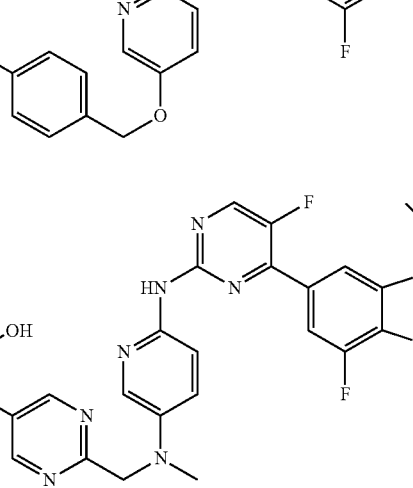
19a, 20a

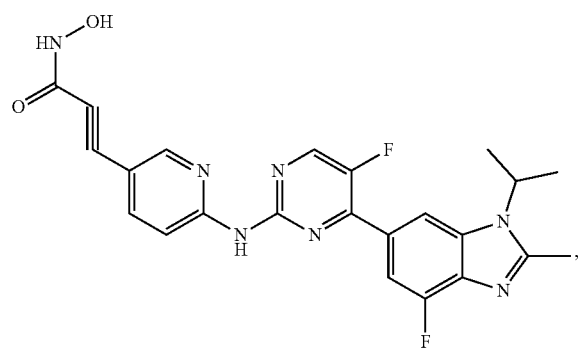
21a
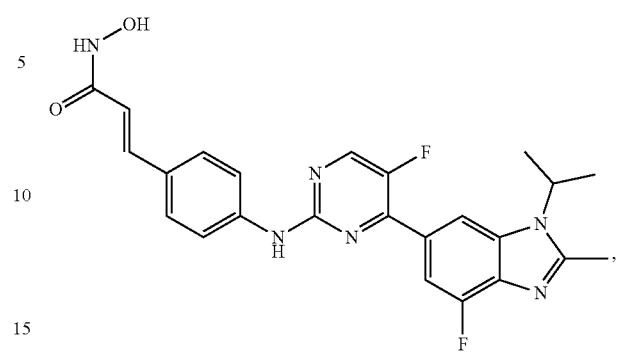
25a
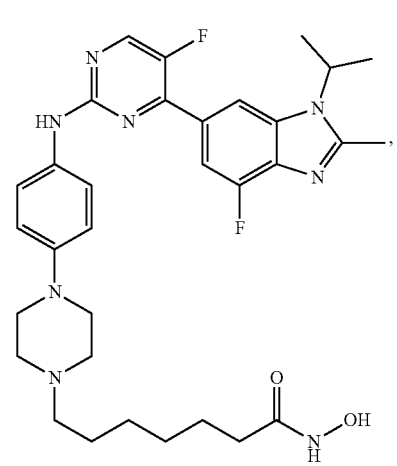
22a
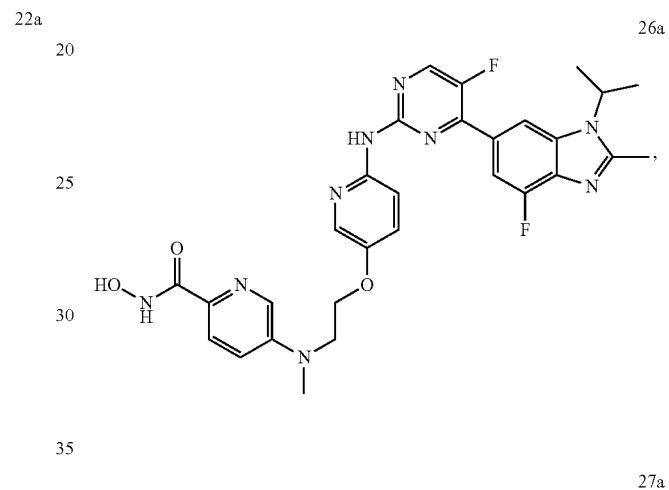
26a
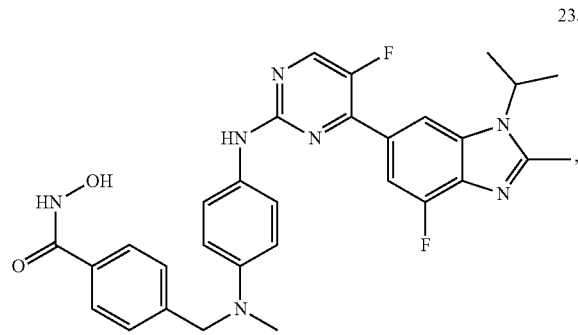
23a
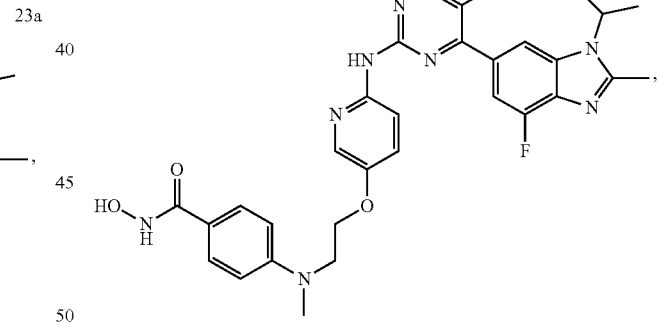
27a
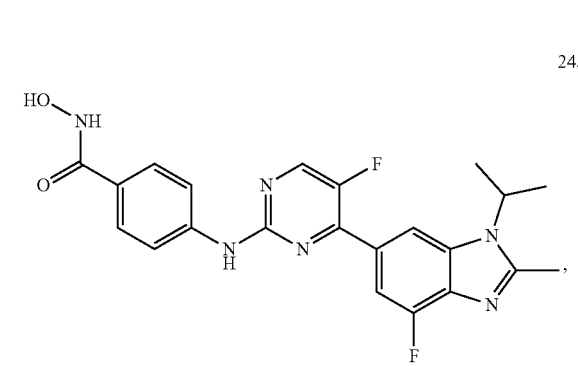
24a
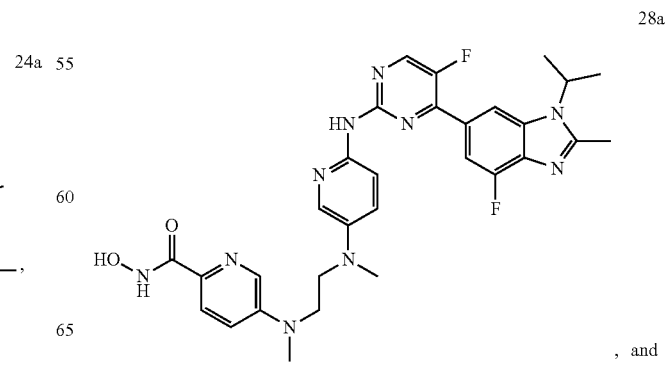
28a
, and -continued

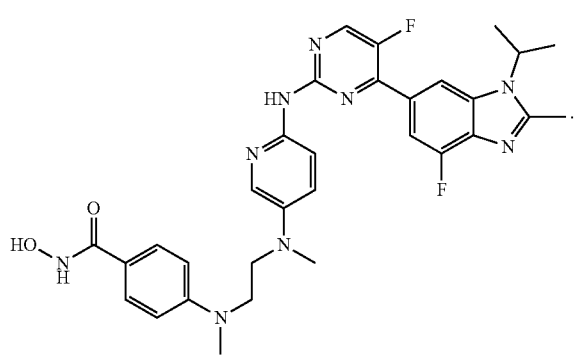

29a

5. A pharmaceutical composition that comprises the compound of claim 1, and pharmaceutically acceptable carrier or excipient.

6. A method for treating or preventing a disease or disorder mediated by cyclin-dependent kinases or histone deacetylases in a subject in need thereof comprising administering to the subject the pharmaceutical composition according to claim 5.

7. The method according to claim 6, wherein the disease or disorder is selected from the group consisting of breast cancer, lymphoma, leukemia, lung cancer, ovarian cancer, liver cancer, melanoma, colon cancer, rectal cancer, kidney cells cancer, small bowel cancer, esophageal cancer, bladder cancer, prostate cancer, and pharyngeal cancer.

8. A pharmaceutical composition that comprises the compound of claim 4, and pharmaceutically acceptable carrier or excipient.

9. A method for treating or preventing a disease or disorder mediated by cyclin-dependent kinases or histone deacetylases in a subject in need thereof comprising administering to the subject the pharmaceutical composition according to claim 8.

10. The method according to claim 9, wherein the disease or disorder is selected from the group consisting of breast cancer, lymphoma, leukemia, lung cancer, ovarian cancer, liver cancer, melanoma, colon cancer, rectal cancer, kidney cells cancer, small bowel cancer, esophageal cancer, bladder cancer, prostate cancer, and pharyngeal cancer.

* * * * *